US009295730B2

(12) United States Patent
Baleux et al.

(10) Patent No.: US 9,295,730 B2
(45) Date of Patent: Mar. 29, 2016

(54) CONJUGATED MOLECULES COMPRISING A PEPTIDE DERIVED FROM THE CD4 RECEPTOR COUPLED TO A POLYANION FOR THE TREATMENT OF AIDS

(75) Inventors: Françoise Baleux, Paris (FR); David Bonnaffe, Paris (FR); Hugues Lortat-Jacob, Saint Ismier (FR); Latino Loureiro-Morais, Cachan (FR)

(73) Assignees: Institut Pasteur, Paris (FR); Commissariat A L'Energie Atomique Et Aux Eneergies Alternatives, Paris (FR); Centre National De La Recherche Scientifique (CNRS), Paris (FR)

( * ) Notice: Subject to any disclaimer, the term of this patent is extended or adjusted under 35 U.S.C. 154(b) by 1128 days.

(21) Appl. No.: 12/866,158

(22) PCT Filed: Jan. 27, 2009

(86) PCT No.: PCT/EP2009/050892
§ 371 (c)(1),
(2), (4) Date: Jan. 19, 2011

(87) PCT Pub. No.: WO2009/098147
PCT Pub. Date: Aug. 13, 2009

(65) Prior Publication Data
US 2011/0105412 A1    May 5, 2011

(30) Foreign Application Priority Data
Feb. 6, 2008    (EP) .................................. 08300074

(51) Int. Cl.
*A61K 38/14* (2006.01)
*A61K 38/16* (2006.01)
*A01N 43/04* (2006.01)
*A61K 31/70* (2006.01)
*A61K 31/727* (2006.01)
*A01N 37/18* (2006.01)
*A61K 38/00* (2006.01)
*A61P 31/18* (2006.01)
*A61P 31/10* (2006.01)
*C07K 9/00* (2006.01)
*C07K 5/00* (2006.01)
*C07K 7/00* (2006.01)
*C07K 16/00* (2006.01)
*C07K 17/00* (2006.01)
*A61K 47/48* (2006.01)
*A61K 38/17* (2006.01)
*C07K 14/73* (2006.01)

(52) U.S. Cl.
CPC ........... *A61K 47/48276* (2013.01); *A61K 38/00* (2013.01); *A61K 38/14* (2013.01); *A61K 38/16* (2013.01); *A61K 38/1761* (2013.01); *A61K 47/4823* (2013.01); *C07K 14/70514* (2013.01)

(58) Field of Classification Search
None
See application file for complete search history.

(56) References Cited

U.S. PATENT DOCUMENTS

| | | | | |
|---|---|---|---|---|
| 2005/0260651 A1* | 11/2005 | Calias et al. | ....................... | 435/6 |
| 2006/0084593 A1* | 4/2006 | Vives et al. | ....................... | 514/8 |
| 2006/0121538 A1* | 6/2006 | Vita et al. | ..................... | 435/7.23 |
| 2006/0166927 A1* | 7/2006 | Bonnaffe et al. | ................ | 514/54 |
| 2011/0015368 A1* | 1/2011 | Baleux et al. | ................. | 530/324 |

FOREIGN PATENT DOCUMENTS

| | | | |
|---|---|---|---|
| JP | 2007-537141 | 12/2007 | |
| WO | WO-03/089000 A2 | 10/2003 | |
| WO | WO 03/089000 A2 | 10/2003 | |
| WO | WO 04/000887 | 12/2003 | |
| WO | WO 2005/058954 | 6/2005 | |
| WO | WO-2007/144685 A1 | 12/2007 | |
| WO | WO 2007/144685 A1 | 12/2007 | |
| WO | WO 2007144685 A1 * | 12/2007 | .......... C07K 14/705 |
| WO | WO-2008/015273 A1 | 2/2008 | |
| WO | WO 2008/015273 A1 | 2/2008 | |

OTHER PUBLICATIONS

Betts et al., "Chap. 14: Amino Acid Properties and Consequences of Substitutions," Bioinformatics for Geneticists, Ed., Barnes et al., John Wiley & Sons, pp. 289-316 (2003).*
Downs et al., "Chlorine, Bromine, Iodine and Astatine," Comprehensive Inorganic Chemistry, ed. Bailar et al., vol. 2, Pergamon Press, Ltd., pp. 1107-1116 (1973).*
Heslop et al., "The Halogens," Inorganic Chemistry, 3rd Ed., Elsevier Publishing Co., pp. 515-520 (1967).*
Politzer, et al., "An overview of halogen bonding," J. Mol. Model. 13:305-311 (2007).*
Stricher, et al., Biochem. J. 390:29-39 (2005).*
P.D. White et al., "Fmoc Solid Phase Peptide Synthesis, a Practical Approach: Basic Principles", Oxford University Press (2000), pp. 9-51.
H.W. Pinnick et al., "Protection for the Hydroxyl Group Including 1,2- and 1,3-Diols" Organic Synthesis, John Wiley & Sons, New York (1981), pp. 10, 52-71, and 194-217.
Barré-Sinoussi, F. et al., "Isolation of a T-Lymphotropic Retrovirus from a Patient at Risk for Acquired Immune Deficiency Syndrome (AIDS)," Science, vol. 220, 868-71, (1983).
Crublet, E. et al., "The HIV-1 Envelope Glycoprotein gp120 Features Four Heparan Sulfate Binding Domains, Includig the Co-receptor Binding Site," J. Biol. Chem., vol. 283, 15193-200, (2008).

(Continued)

*Primary Examiner* — James H Alstrum Acevedo
*Assistant Examiner* — Thea D' Ambrosio
(74) *Attorney, Agent, or Firm* — Finnegan, Henderson, Farabow, Garrett & Dunner, LLP

(57) ABSTRACT

This invention relates to a conjugated molecule comprising a peptide derived from the CD4 receptor coupled to an organic molecule by means of a linker as well as a process for its preparation. Such a conjugated molecule can be used in antiviral treatment, namely in the treatment of AIDS.

11 Claims, 13 Drawing Sheets

(56) References Cited

OTHER PUBLICATIONS

Figure 2:
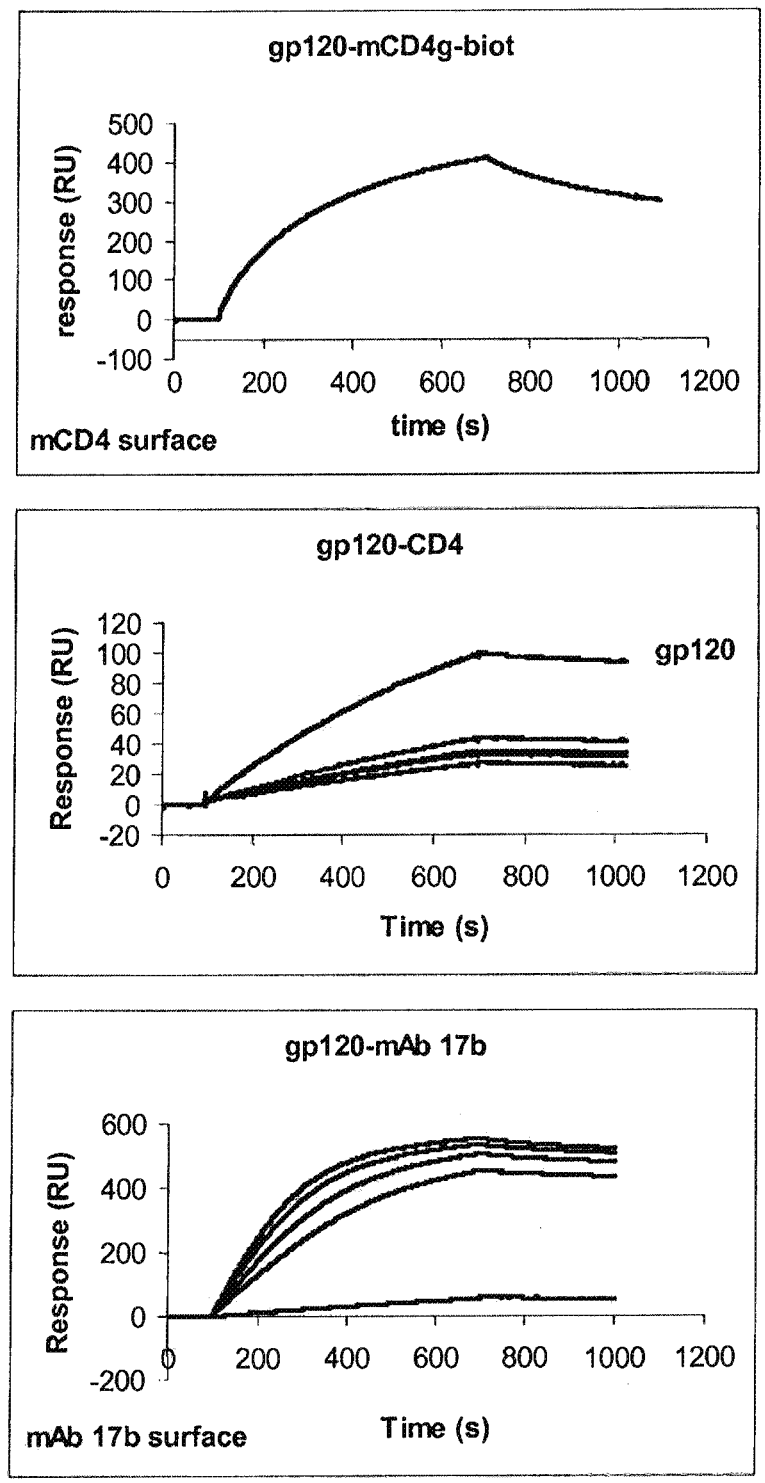

Esté, J., et al. "Development of Resistance of Human Immunodeficiency Virus Type 1 to Dextran Sulfate Associated with the Emergence of Specific Mutations in the Envelope gp120 Glycoprotein," *Mole. Pharma.* vol. 52, 98-104, (1997).

Flexner, C., et al., "Pharmacokinetics, Toxicity, and Activity of Intravenous Dextran Sulfate in Human Immunodeficiency Virus Infection," *Antimicro. Agents & Chemo.*, vol. 35, 2544-50, (1991).

Gartner, S., et al., "The Role of Mononuclear Phagocytes in HTLV-III/LAV Infection," *Science*, vol. 233, 215-19, (1986).

Huang, C. et al., "Scorpion-Toxin Mimics of CD4 in Complex with Human Immunodeficiency virus gp120: Crystal Structures, Molecular Mimicry, and Neutralization Breadth," *Structure*, vol. 13, 755-68, (2005).

Jinno-Oue, A., et al., "The Synthetic Peptide Derived From the NH2-terminal Extracellular Region of an Orphan G Protein-coupled Receptor, GPR1, Preferentially Inhibits Infection of X4 HIV-1," *J. Biol. Chem.*, vol. 280, 30924-34, (2005).

Lubineau, A., et al., "Synthesis of Tailor-Made Glycoconjugate Mimetics of Heparan Sulfate that Bind IFN-γ in the Nanomolar Range," *Chem. Eur. J.* vol. 10, 4265-82, (2004).

Moulard, M., et al., "Selective Interactions of Polyanions with Basic Surfaces on Human Immunodeficiency Virus Type 1 gp120," *J Virol.*, vol. 74, 1948-60, (2000).

Najjam, S., et al., "Characterization of Human Recombinant Interleukin 2 Binding to Heparin and Heparan Sulfate Using an Elisa Approach," *Cytokine*, vol. 9, 1013-22, (1997).

Noti, C., et al., "Preparation and Use of Microarrays Containing Synthetic Heparin Oligosaccharides for the Rapid Analysis of Heparin-Protein Interactions," *Chem. Eur. J.*, vol. 12, 8664-86, (2006).

Schenten, D., et al., "Effects of Soluble CD4 on Simian Immunodeficiency Virus Infection of CD4-Positive and CD4-Negative Cells," *J. Virol.* vol. 73, 5373-80, (1999).

Tamalet, C. et al., "Resistance of HIV-1 to Multiple Antiretroviral Drugs in France: A 6-year Survey (1997-2002) Based on an Analysis of Over 7000 Genotypes," *AIDS*, vol. 17, 2383-88, (2003).

Vivès, R. et al., "A Novel Strategy for Defining Critical Amino Acid Residues Involved in Protein/Glycosaminoglycan Interactions," *J. Biol. Chem.*, vol. 279, 54327-33, (2004).

Vivès, R. et al., "Heparan Sulfate Targets the HIV-1 Envelope Glycoprotein gp120 Coreceptor Binding Site," *J. Biol. Chem.*, vol. 280, 21353-57, (2005).

von Kärber, G. "Beitrag zur kollektiven Behandlung pharmakologischer Reihenversuche," Eingegangen am 1. VIII (1931).

International Search Report dated Nov. 23, 2009 for PCT/EP2009/050892.

International Search Report from the European Patent Office for International Application No. PCT/EP2009/050892 (Mail date: Nov. 30, 2009).

Huang et al.; "Scorpion-Toxin Mimics of CD4 in Complex With Human Immunodeficiency Virus gp120: Cryatal Structures, Molecular Mimicry, and Neutralization Breadth," Structure, vol. 13, pp. 755-768, (2005).

\* cited by examiner

Binding site to CD4
← V3 loop

CD4 gp120 binding site to the co-receptor (not accessible)

CD4i site (binding site to the co-receptor) exposed by binding of CD4 to gp120

Hybrid molecule: mCD4-HS

+ gp120 → gp120 whose interaction site with CD4, V3 loop and interaction site with the co-receptor are blocked

Figure 1

CONJUGATED MOLECULES COMPRISING A PEPTIDE DERIVED FROM THE CD4 RECEPTOR COUPLED TO A POLYANION FOR THE TREATMENT OF AIDS

CROSS REFERENCE TO RELATED APPLICATIONS

This is a national stage application under 35 U.S.C. §371 of International Application No. PCT/EP2009/050892, filed on Jan. 27, 2009, which claims the benefit of priority of European Patent Application EP 08300074.5, filed on Feb. 6, 2008.

SEQUENCE LISTING

The instant application contains a Sequence Listing which has been submitted electronically in ASCII format and is hereby incorporated by reference in its entirety. Said ASCII copy, created on Mar. 4, 2014, is named 03715.0180_SL.txt and is 5,868 bytes in size.

This invention relates to a conjugated molecule comprising a peptide derived from the CD4 receptor and an organic molecule, such as a polyanionic polysaccharide. Such a conjugated molecule can be used in antiviral treatment, namely in the treatment of AIDS. This invention further relates to processes for the preparation of the conjugated molecule.

Triple therapies combining nucleoside (NRTI), non-nucleoside (NNRTI) and/or protease inhibitors (PI) result in a reduction in viral charge beneath levels of detection in a large number of seropositive HIV patients. This efficacy has led to a substantial decrease in the number of deaths resulting from HIV infection. Unfortunately, genotypes with antiviral resistance have been found in 80% of patients and, more worryingly, 45.5% of viral populations are resistant to NRTI/PI combinations while 26% are resistant to a combination of three anti-HIV classes (Tamalet et al., AIDS. 2003 Nov. 7; 17(16):2383-8). This observation is particularly disturbing since the adverse effects of long-term triple therapy treatment (lipoatrophy, lipodystrophy, hypertriglyceridaemia, hypercholesterolaemia, neuropathy, etc.) found in 70% of patients receiving the treatment result in poor compliance and "sudden" discontinuation of treatment which often leads to resistance. The development of less severe forms of treatment with fewer adverse effects and without cross-resistance is therefore a priority despite the large number of currently available medications on the market. With this in mind, it is essential to target HIV replication steps other than reverse transcription and proteolysis.

Entry of a virus into a cell is a crucial step in the viral infection cycle. This process is divided into two phases, the first of which is interaction of the virus with the cell surface at the level of specific host receptors, followed by penetration of the virus' genetic material into the target cell. With HIV, the molecular partners involved in the mechanisms of adhesion and entry are well established. From the viral side, the gp120 envelope glycoprotein is what essentially determines the virus/cell interaction complex. This protein initially binds to a transmembrane glycoprotein of the host cell, CD4. This interaction leads to a conformational change in gp120 which exposes a particular epitope, called CD4-induced (CD4i), thus creating a binding site for chemokine receptors (essentially CCR5 and CXCR4). CCR5 and CXCR4 therefore act as gp120 co-receptors at the cell surface. This second interaction leads to re-organization of the gp120/gp41 protein complex and initiation of cell/virus membrane fusion.

The cellular tropism of the HIV virus is defined by the type of co-receptor used. So-called X4 or <<T-tropic>> viruses tend more specifically to infect cell lines expressing CXCR4 at their surface, such as the T lymphocytes. So-called R5 or <<M-tropic>> viruses use co-receptor CCR5 and mainly infect macrophages and monocytes. The presence of type R5 or X4 viruses is generally associated with quite distinct stages of AIDS development (asymptomatic phase for R5, appearance of X4 virus often linked to unfavourable evolution outcome of the disease, suggesting that use of co-receptor CXCR4 is an important factor in the pathogenesis of AIDS). As the structural determinants for recognition of CCR5 and CXCR4 are carried by gp120, the R5 and X4 viruses represent two separate targets.

In addition to the receptors described above, HIV is capable of binding to other molecules found at the cell surface, particularly heparan sulphates (HSs). HSs are polysaccharides belonging to the glycosaminoglycan family (GAGs). They are found in large quantities at the cell surface and in the interstitial matrices, anchored to the extracellular area of specific glycoproteins. Chemically related to heparin (another GAG used for its anticoagulant properties), HSs differ from other biological macromolecules through the diversity of their structure and functions. As a result of their ability to bind to many different proteins, whose structure, stability and/or reactivity are modified by the interaction, they are involved in a very large number of phenomena. In particular, they recognize numerous pathogens, one of which is HIV and thus act as binding receptors. In HIV, it is also gp120 which carries HS recognition sites.

The Inventors' previous work found that HIV's ability to attach to heparin (or HS) was specific to X4 type strains, as the R5 type virus interacts only very slightly with the polysaccharide (Moulard et al., J. Virol. 74, 1948-1960, 2000). These results suggest that HS could be involved in some of the specific properties associated with cell tropism, such as the nature of target cells, the greater pathogenecity of X4 strains and the building up of reservoirs of latent X4 virus during the asymptomatic stage of the infection.

HIV-HS interaction takes place at the level of gp120 which, as seen by the Inventors, is involved in all the initial stages of viral attachment and entry. The interaction site is located on a region of the gp120 called variable loop 3 (V3). The V3 loops of X4 isolates are enriched with basic amino acids compared to the V3 loops of R5 isolates, resulting in better interaction with heparin-like oligosaccharides.

The invention described herein is based on the observation that the gp120-heparin interaction is highly potentialised in the presence of CD4. However, this effect is dependent on the viral isolate used and essentially occurs at concentrations at which gp120 alone interacts only weakly with HSs.

The Inventors' previous work has shown that the site induced by CD4 constitutes a supplementary interaction site with heparin or HSs (Vivès et al. J. Biol. Chem. 279, 54327-54333, 2005). The inhibitor (mCD4-HS), whose biological effects are described below, therefore includes a peptide (mCD4) which binds to gp120 at the CD4 recognition site. It is capable of triggering conformational changes in gp120 which result in exposure of the CD4i epitope. The covalently bound oligosaccharide (HS) is then capable of recognizing the CD4i site, according to FIG. 1.

It has been known for many years that certain polyanions such as heparin (HP) and dextran sulphate (DS) but not chondroitin sulphate (CS) are capable of inhibiting the infection of cells by HIV (Esté J A et al., Mol Pharmacol. 1997 July; 52(1):98-104). They are nonetheless not used clinically, particularly as a result of their anticoagulant effects (Flexner C et al., Antimicrob Agents Chemother. 1991 December; 35(12): 2544-50). It has recently been shown that the molecular mechanism of this inhibition is linked to interaction of the polyanion with the V3 loop (Moulard M et al., J Virol. 2000 February; 74(4):1948-60).

Moreover, various studies have explored the use of soluble CD4 to inhibit interaction of the virus with CD4 expressed at the surface of HIV target cells. This solution was found to be ineffective since soluble CD4, by binding to the virus, exposes the epitope CD4i and thus encourages interaction of the virus with the CCR5 or CXCR4 co-receptor which, in some cases, increases infection (Schenten D. et al., 1999. J Virol. 73:5373-80).

It is known from international patent WO 03/089000 that a peptide derived from the CD4 receptor, when contacted with a polyanion, has an anti-HIV activity. In particular, it is recommended that compounds in which the peptide and polyanion are bound can be prepared according to the description given in the article by Najjam S. et al. (Cytokine 1997, 9 (12):1013-1022) (refer to point I.1 in the EXAMPLES section).

In this invention, the inventors have obtained activated peptides derived from the CD4 receptor, which are likely to bind directly and covalently to the organic molecule such as a polyanionic polysaccharide. This activation requires the insertion of specific amino acid residues into the native peptide. In particular, the inventors have discovered that the presence of one and only one residue of the amino acid lysine in the sequence of the peptide derived from the CD4 receptor is vital to obtaining an activated peptide according to the invention. Moreover, this sole amino acid lysine residue has to be in a well-defined position in the sequence of the peptide derived from the CD4 receptor. Devising a miniCD4 peptide containing a single amino acid lysine residue in a defined position allows the introduction of the desired function selectively and directly onto miniCD4.

The idea to design a miniCD4 bearing a single derivatisation/coupling site was developed in order to simplify the synthesis of the mCD4-based conjugates. Our strategy allows the coupling of numerous organic compounds via a large panel of linkers and chemistries after the miniCD4 has been properly synthesized, folded, purified and characterized. This strategy enables us to generate perfectly defined conjugates.

The person skilled in the art could argue that methods for specific labeling/derivatisation of selected aminoacids within a peptide sequence exist. However, the presence of multiple cystein residues within miniCD4 sequences limits the use of some of the classical methods generally used in solid-phase peptide synthesis to selectively modify/derivatise the selected amino acid (see FIG. 10).

In that line, introduction of a maleimide group on a selected Lysine side chain is not possible.

Indeed, use of thiolated scavengers during the final TFA clivage and gluthation based conditions required for proper synthesis and folding of miniCD4 peptides preclude the opportunity to introduce the maleimide function (or other thiolated sensitive derivatising molecules) on the selected Lysine while the peptide still attached on the support. As a matter of fact, this precludes for example, the use of the robust maleimide/SH strategy for the mCD4-polyanion conjugation step.

Moreover, our post-mCD4 synthesis derivatisation strategy enable the rapid screening of different linkers, without the need to perform multiple on-peptide resin derivatisation, clivage and folding of the mCD4 peptide.

Figure 11:
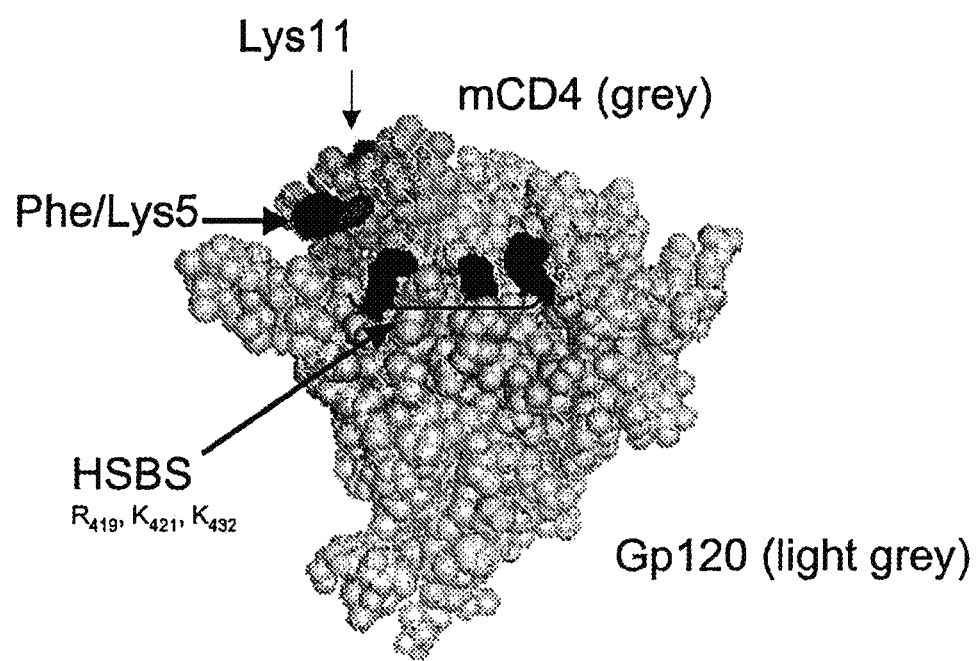

More importantly, the judicious location of the derivatisation site (Lysine) within the miniCD4 sequence (e.g. position 5) affords an optimized orientation of the polyanionic compounds that target the CD4i's HSBS and co-receptor binding site (see FIG. 11).

This invention therefore offers activated peptides which make it possible to produce numerous potential antiviral derivatives. These derivatives consist of conjugated molecules comprising a CD4 peptide specifically coupled to an organic molecule such as a polyanionic polysaccharide by means of a linker.

This approach is therapeutically advantageous to inhibit viral attachment to cells as it directly targets the virus and not the cells themselves. It is therefore, at first sight, devoid of the cellular effects observed with medication which binds to co-receptors. In addition, in view of the preservation of the sites involved as a function of various viral tropisms, the compounds according to the invention should interact with the gp120 of different viral isolates. Also, while it might be misleading to think that resistance will not occur, this new type of compound should not lead to easy emergence of resistance. Indeed, the CD4 site of gp120 has to remain intact in order to continue to bind to CD4, as do the basic residues involved in binding to the polyanionic polysaccharide for interaction with the co-receptors. Mutation in one of these two sites should result in a virus with reduced infectivity. Finally, within the framework of the invention, a wholly synthetic version of the compounds can be developed, thus guaranteeing a preparation available in large quantities and one that is homogeneous and perfectly defined. The coupling method is simple, rapid and quantitative.

Therefore, according to a first aspect, the invention covers a conjugated molecule comprising a peptide derived from the CD4 receptor, said peptide being coupled to an organic molecule by means of a linker, wherein:

the peptide derived from the CD4 receptor comprises the following general sequence (I):

```
                                              (SEQ ID NO: 5)
Xaaf-P1-Lys-Cys-P2-Cys-P3-Cys-Xaag-Xaah-Xaai- Xaaj-Cys-Xaak-Cys-Xaal-Xaam, (I)
``` in which:
P1 represents 3 to 6 amino acid residues,
P2 represents 2 to 4 amino acid residues,
P3 represents 6 to 10 amino acid residues,
Xaa$^f$ represents N-acetylcysteine (Ac-Cys) or thiopropionic acid (TPA),
Xaa$^g$ represents Ala or Gln,
Xaa$^h$ represents Gly or (D) Asp or Ser,
Xaa$^i$ represents Ser or His or Asn,
Xaa$^j$ represents biphenylalanine (Bip), phenylalanine or [beta]-naphthylalanine,
Xaa$^k$ represents Thr or Ala,
Xaa$^l$ represents Gly, Val or Leu, and
Xaa$^m$ represents —NH$_2$ or —OH,
the amino acid residues in P1, P2 and P3 being natural or non-natural, identical or different, said residues of P1, P2 and P3 being all different from the Lys residue and P1, P2 and P3 having a sequence in common or not, and
the organic molecule has the following general structure (II):

$$\text{(II)}$$

[Chemical structure diagram of formula (II) showing a polysaccharide structure with OR³, R¹O, R⁴R⁵N, OR¹, ⁻OOC, R²O, OR³ groups, with repeating unit mX and subscript n, terminating in A—Z]

in which:
- n represents an integer comprised between 0 and 10, in particular n is 0, 1, 2, 3, 4, 5, 6, 7, 8, 9 or 10 and advantageously, n is 0, 1, 2, 3, 4 or 5,
- X represents an inorganic couterion, such as Na⁻, K⁺, Li⁺, or $Mg^{2+}$, or an organic counterion, such as $R_3NH^+$, $R_4N^+$, with R representing, independently from each other, an alkyl group, and advantageously is Na⁺,
- m represents the number of negative charges of the molecule,
- $R^1$ are identical or different radicals and represent an hydrogen atom or a O-Protecting group GP,
- $R^2$ represents an hydrogen atom or a O-Protecting group GP', wherein GP and GP' are identical or different,
- $R^3$ are identical or different radicals and represent an hydrogen atom, a sulphate, a phosphate or any anionic group,
- $R^4$ are identical or different radicals and represent an hydrogen atom, a sulfate, an alkyl or an acyl group,
- $R^5$ are identical or different radicals and represent an hydrogen atom, an alkyl or an acyl group,
- A represents a group chosen among those of formula: —(CH₂)ₚ—NH—CO—(CH₂)_q—, —(CH₂—CH₂)—(O—CH₂—CH₂)ₚ—NH—CO—(CH₂)_q—, —(CH₂)ₚ—NH—CO—(CH₂—CH₂—O)_q—(CH₂—CH₂)— or —(CH₂—CH₂)—(O—CH₂—CH₂)ₚ—NH—CO—(CH₂—CH₂—O)_q—(CH₂—CH₂)—,
  wherein p represents an integer comprised between 1 and 10 and q represents an integer comprised between 1 and 10, and advantageously A represents a group of formula —(CH₂)₅—NH—CO—(CH₂)₂—, and
- Z represents an halogen atom, a thiol or a maleimide group, the linker being covalently bound at one of its extremity to the free amino group (—NH₂) of the amino acid residue Lys present in general sequence (I) of the peptide derived from the CD4 receptor, and being covalently bound at its other extremity to the Z group of the organic molecule.

Preferably, P3 comprises at least one basic amino acid, said basic amino acid being even more preferably arginine. The presence of basic residues in this portion of the CD4 receptor fragment contributes to its binding to the gp120 protein. The inventors therefore prefer to introduce at least one basic amino acid into P3, preferably arginine. This maintains thus a basic moiety which is not reactive at derivation at pH 7-8 but which has been found to be useful for the binding of miniCD4 peptide to the gp120 protein.

In this application, the terms "miniCD4 peptide", "CD4 peptide" and "miniCD4" are used interchangeably to designate the peptide derived from the CD4 receptor comprising or consisting of general sequence (I) defined above.

This invention needs the peptide derived from the CD4 receptor to include in its general sequence (I) one and only one residue of the amino acid lysine (Lys) in the position defined in general sequence (I).

The Cys residues in general sequence (I) allow the formation of three disulphide bridges needed for folding back of miniCD4.

Thiopropionic acid (TPA), when it is in the N-terminus position of the peptide of general sequence (I), makes it possible to reduce hindrance in N-ter and overcome the presence of an amine group.

Thus, according to a preferred embodiment, $Xaa^f$ represents TPA in general sequence (I).

In general sequence (I), $Xaa^j$ represents Bip, Phe or [beta]-naphthylalanine. Biphenylalanine increases contact with glycoprotein gp120 in the cavity where the Phe 43 of CD4 receptor is lodged. Nevertheless, a miniCD4 peptide according to the invention with a Phe may mimic CD4 better when the structure of the miniCD4/gp120 complex is analyzed (Huang C C et al., Structure. 2005 May; 13(5):755-68).

Thus according to another preferred embodiment, $Xaa^j$ represents Phe.

The peptide of general sequence (I) derived from the CD4 receptor has an alpha helix structure followed by a beta sheet. The amino acids $Xaa^g$-$Xaa^h$-$Xaa^i$-$Xaa^j$-Cys-$Xaa^k$-Cys-$Xaa^l$ participate in a major way to the binding to gp120. These peptides have $IC_{50}$ (affinity for gp120) similar to those of sCD4 (soluble CD4).

The peptide of general sequence (I) derived from the CD4 receptor can be prepared by conventional solid phase chemical synthesis techniques, for example according to the Fmoc solid phase peptide synthesis method ("Fmoc solid phase peptide synthesis, a practical approach", edited by W. C. Chan and P. D. White, Oxford University Press, 2000) and/or by genetic recombination.

Preferably, the sequence of the peptide derived from the CD4 receptor of general sequence (I) is chosen from the group consisting of sequences SEQ ID No. 1 and SEQ ID No. 2, advantageously SEQ ID No. 1.

The term "linker" refers in the present invention to a linker obtained by the coupling of a bifunctional compound, as defined below, with a peptide derived from the CD4 receptor and the organic molecule.

Thus, the length of the linker varies as a function of the bifunctional compounds used.

In particular, the linker will be advantageously chosen among:

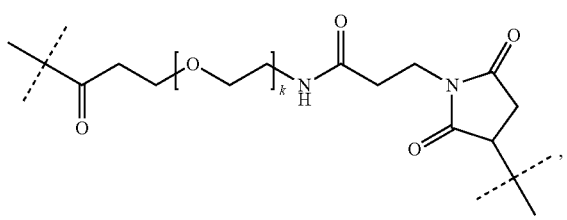

with k representing an integer comprised between 2 and 24, and being advantageously 2, 4, 8 or 12,

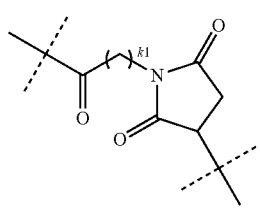

with k1 representing an integer comprised between 1 and 10, thus equal to 1, 2, 3, 4, 5, 6, 7, 8, 9 or 10, and advantageously equal to 1, 2, 3, 5 or 10,

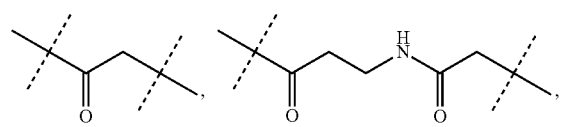

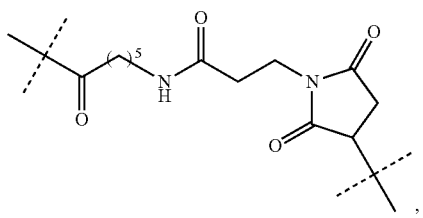

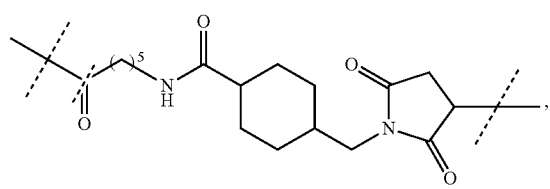

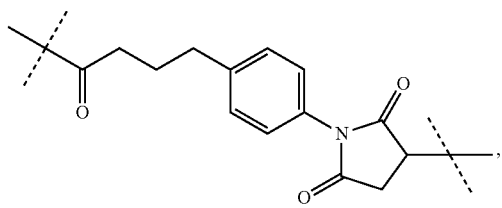

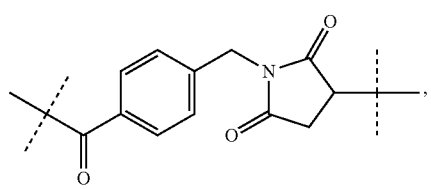

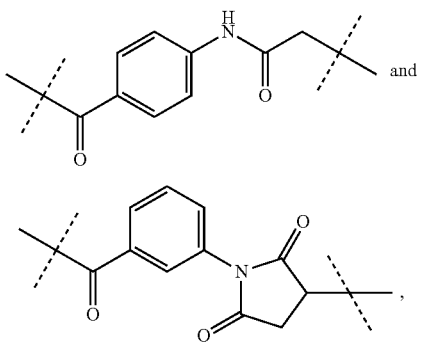

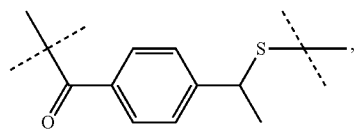

when Z represents a thiol group, and among:

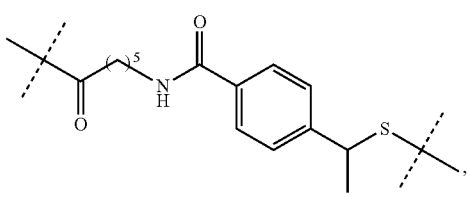

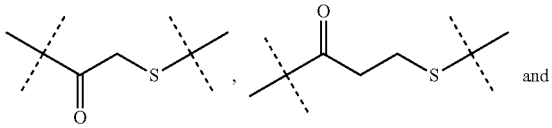

when Z represents a maleimide group or a halogen atom.

In a preferred embodiment, the linker will be chosen among:

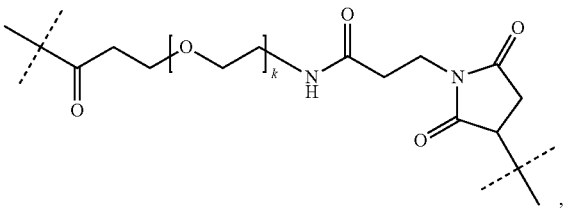

with k representing an integer comprised between 2 and 24, and being advantageously 2, 4, 8 or 12, and

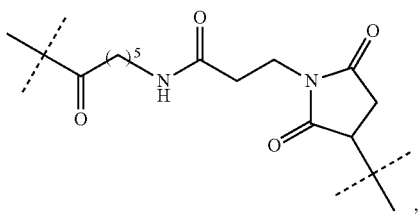

when Z represents a thiol group, and among:

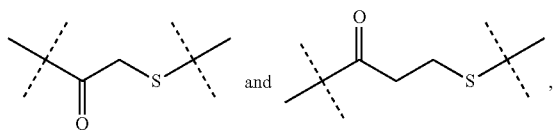

when Z represents a maleimide group or a halogen atom.

Such linkers correspond thus to the use of succinimidyl-6-[beta-maleimidopropionamido]hexanoate (SMPH), NHS-PEO$_n$-maleimide, with n representing an integer comprised between 2 and 24, and being advantageously 2, 4, 8 or 12, SATA (N-succinimidyl-S-acetylthioacetate) and SATP (N-succinimidyl-S-acetylthiopropionate), as bifunctional compound.

In another preferred embodiment, the linker is

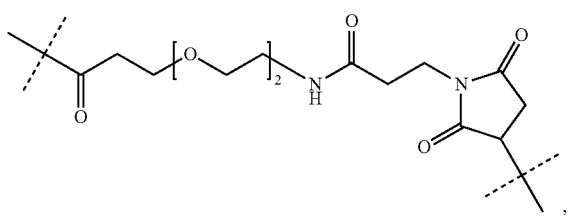

which derived from the bifunctional compound NHS—PEO$_2$-maleimide.

The organic molecule of formula (II) represents a particular form of heparin, with a low degree of polymerisation, modified in order to introduce a functional group Z on this molecule.

The term "O-Protecting group" as used in the present invention refers to a substituent which protects hydroxyl groups against undesirable reactions during synthetic procedures such as those O-protecting groups disclosed in Greene, "Protective Groups In Organic synthesis", (John Wiley & Sons, New York (1981)). O-protecting groups comprise methyl or alkyl ethers substituted or not, for example, methoxymethyl (MOM), benzyloxymethyl, 2-methoxyethoxymethyl, 2-(trimethylsilyl)ethoxymethyl, t-butyl, benzyl and triphenylmethyl, benzyl ethers substituted or not, such as p-methoxybenzyl, tetrahydropyranyl ethers, substituted ethyl ethers, for example, 2,2,2-trichloroethyl, silyl ethers, for example, trimethylsilyl (TMS), t-butyldimethylsilyl (TBS) and t-butyldiphenylsilyl; and esters prepared by reacting the hydroxyl group with a carboxylic acid for example, acetate, propionate, benzoate and the like. In particular an allyl or an acetyl group are a "O-Protecting group" according to the present invention.

Advantageously, it is a methyl, benzyl or p-methoxybenzyl group.

The term "alkyl" as used in the present invention refers to straight or branched chain substituted or unsubstituted alkyl radicals containing from 1 to 6 carbon atoms including, but not limited to, methyl, ethyl, n-propyl, iso-propyl, n-butyl, iso-butyl, sec-butyl, t-butyl, n-pentyl, n-hexyl and the like.

The term "acyl" as used in the present invention refers to an alkyl-CO group with alkyl being as defined above.

The term "halogen" refers to fluorine, chlorine, bromine or iodine.

In a preferred embodiment, Z represents a thiol group.

In a particular embodiment, radicals $R^1$ are all identical.

In another particular embodiment, radicals R1 are chosen from the group consisting of a hydrogen atom, a methyl and a benzyl group.

Advantageously, $R^2$ is a hydrogen atom, a methyl or a p-methoxybenzyl (pMBn) group.

Advantageously, $R^3$ are a sulphate or phosphate moiety.

More advantageously, $R^3$ are all identical, and in particular are a phosphate moiety.

Advantageously, $R^4$ are all identical, and in particular are a sulphate moiety.

Advantageously, $R^5$ are all identical, and in particular are a hydrogen atom.

In a preferred embodiment, the organic molecule will be chosen among:

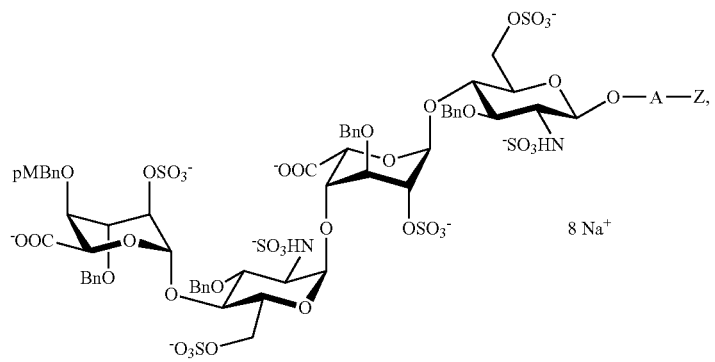

-continued
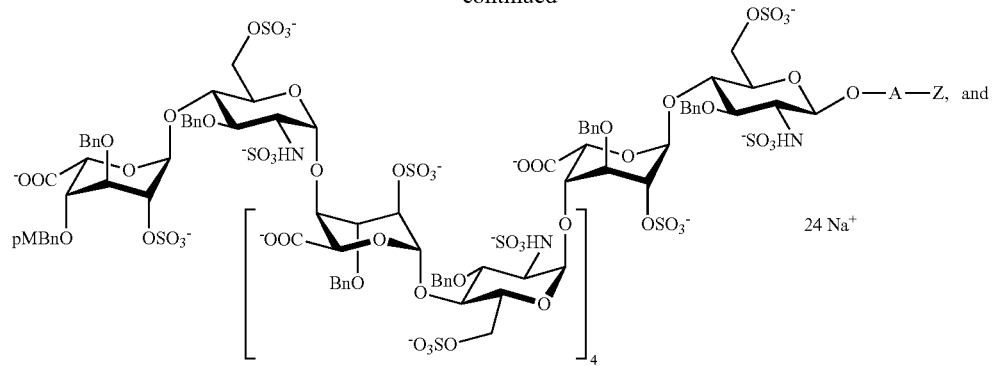
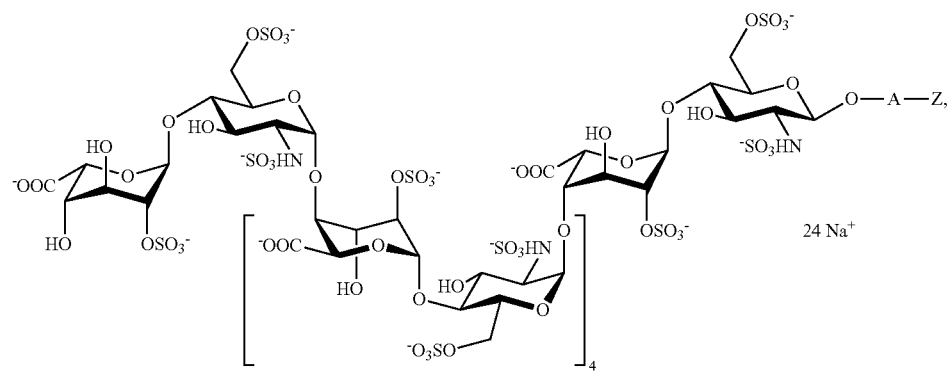
with A and Z as defined above.
Advantageously, A represents a group of formula —(CH$_2$)$_5$—NH—CO—(CH$_2$)$_2$—.
Advantageously Z represents a thiol group.
In a preferred embodiment, the organic molecule will be chosen among:
(compound 20)
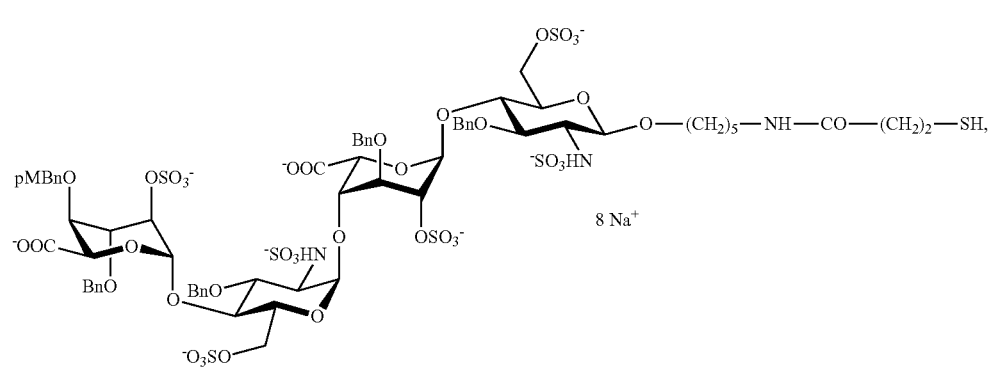
(compound 21)
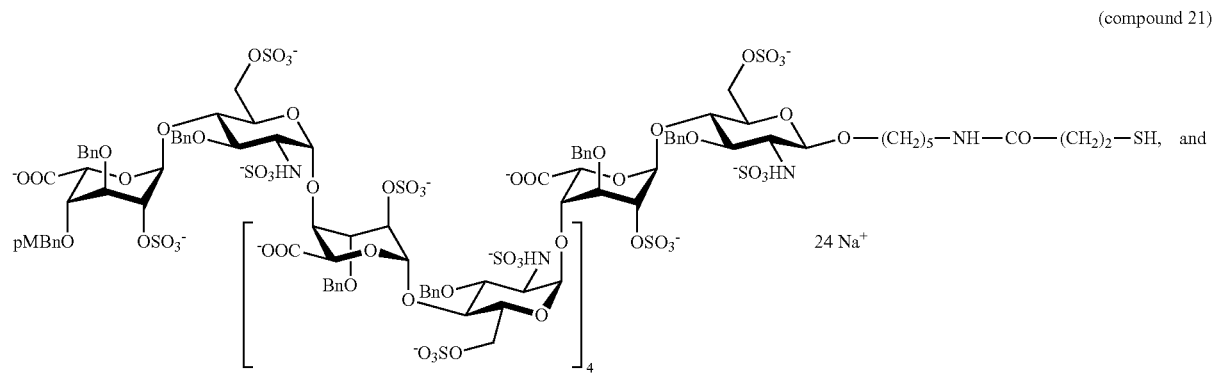

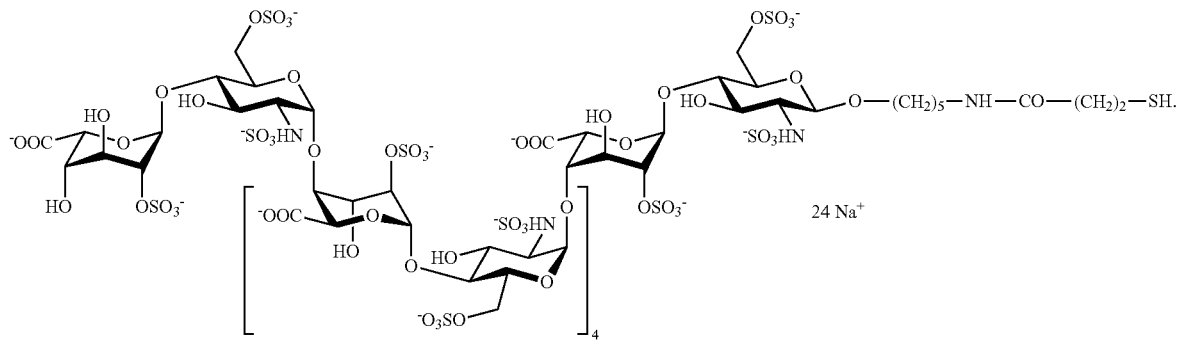
(compound 22)
In particular, a conjugated molecule according to the invention can be one of the following molecules:
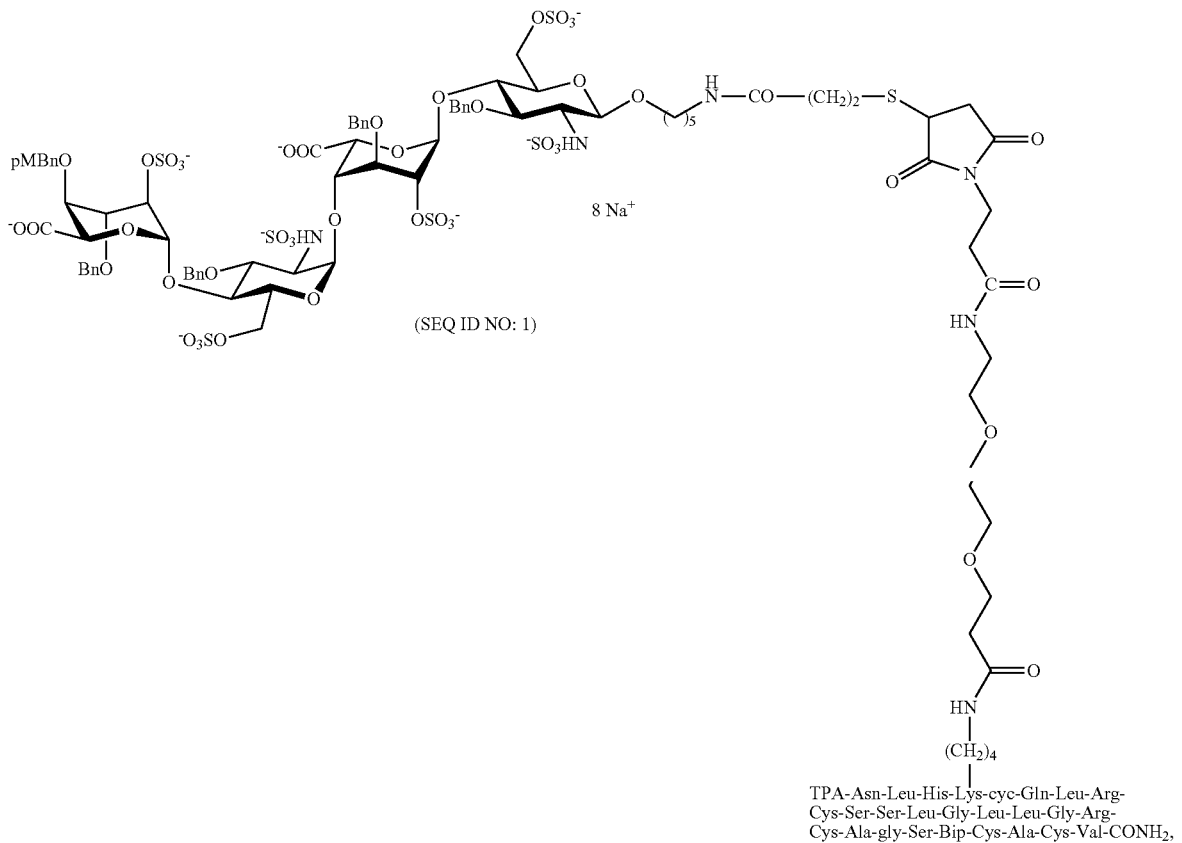
(compound 23)
(SEQ ID NO: 1)
TPA-Asn-Leu-His-Lys-cyc-Gln-Leu-Arg-
Cys-Ser-Ser-Leu-Gly-Leu-Leu-Gly-Arg-
Cys-Ala-gly-Ser-Bip-Cys-Ala-Cys-Val-CONH$_2$, -continued
(compound 24)
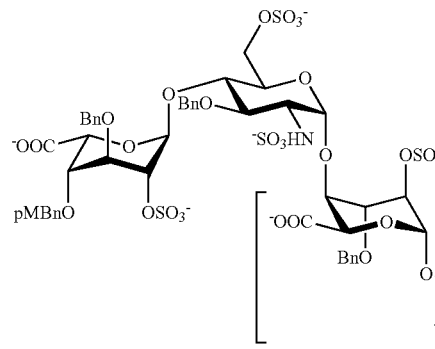
(SEQ ID NO: 1)
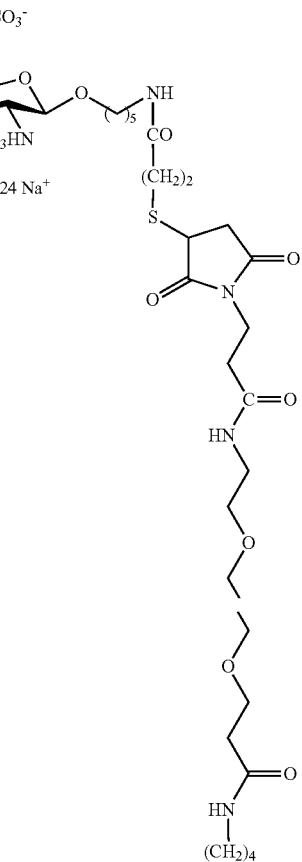
TPA-Asn-Leu-His-Lys-cys-Gln-
Leu-Arg-Cys-Ser-Ser-Leu-Gly-
Leu-Leu-Gly-Arg-Cys-Ala-gly-
Ser-Bip-Cys-Ala-Cys-Val-CONH2, and
(compound 25)
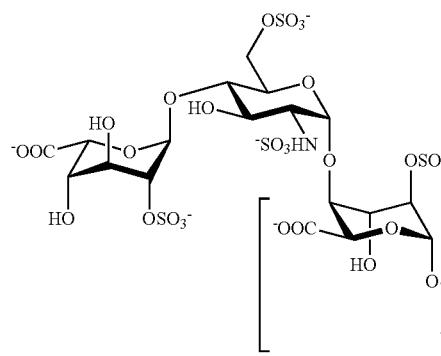
(SEQ ID NO: 1)
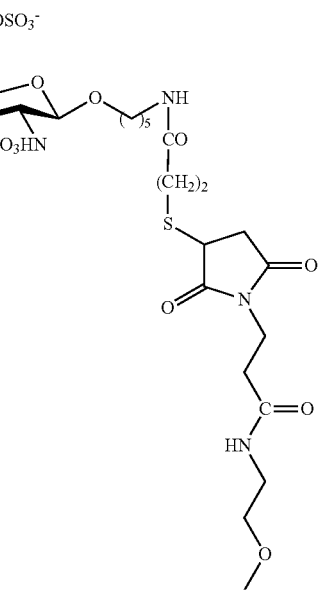

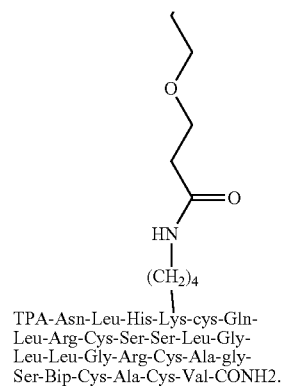

TPA-Asn-Leu-His-Lys-cys-Gln-
Leu-Arg-Cys-Ser-Ser-Leu-Gly-
Leu-Leu-Gly-Arg-Cys-Ala-gly-
Ser-Bip-Cys-Ala-Cys-Val-CONH2.

Moreover, according to a second aspect, the invention covers a conjugated molecule comprising a peptide derived from the CD4 receptor coupled to an organic molecule by means of a linker, wherein:

the peptide derived from the CD4 receptor comprises the general sequence (I) as defined above, and the organic molecule represents a polyanion chosen among heparin and heparan sulphate, in which the uronic acid moiety can be either a glucuronic or an iduronic acid, with a degree of polymerisation dp of 2 to 24, wherein essentially all the free hydroxy groups of the polyanion are substituted by a O-Protecting group GP", these GP" groups being identical or different, and wherein the polyanion is modified so that it carries a functional group chosen among a halogen atom, a thiol or a maleimide group, the linker being covalently bound at one of its extremity to the free amino group (—NH$_2$) of the amino acid residue Lys present in general sequence (I) of the peptide derived from the CD4 receptor, and being covalently bound at its other extremity to the functional group of the organic molecule.

The term "essentially" means in the present invention that all or almost all the free hydroxy groups of the polyanion are substituted by a O-Protecting group, preferably 70%, more preferably 80%, even more preferably 90% of the free hydroxy groups are substituted.

The characteristics of the peptide derived from CD4 receptor are the same as defined above.

In particular, P3 comprises preferably at least one basic amino acid, said basic amino acid being even more preferably arginine.

According to a preferred embodiment, Xaa$^f$ represents TPA in general sequence (I).

According to another preferred embodiment, Xaa$^j$ represents Phe.

Preferably, the sequence of the peptide derived from the CD4 receptor of general sequence (I) is chosen from the group consisting of sequences SEQ ID No. 1 and SEQ ID No. 2, advantageously SEQ ID No. 1.

The linker is as defined above and advantageously, is chosen among:

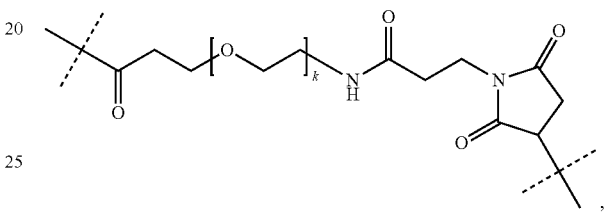

with k representing an integer comprised between 2 and 24, and being advantageously 2, 4, 8 or 12,

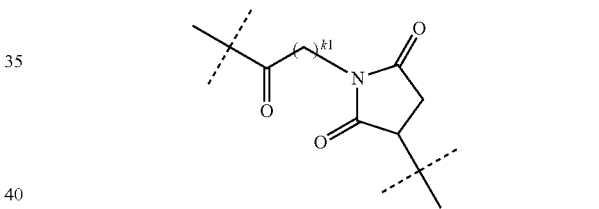

with k1 representing an integer comprised between 1 and 10, thus equal to 1, 2, 3, 4, 5, 6, 7, 8, 9 or 10, and advantageously equal to 1, 2, 3, 5 or 10,

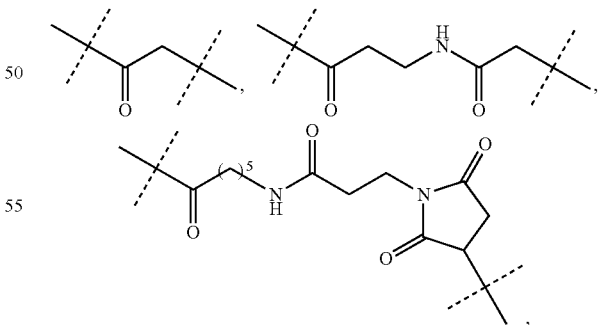

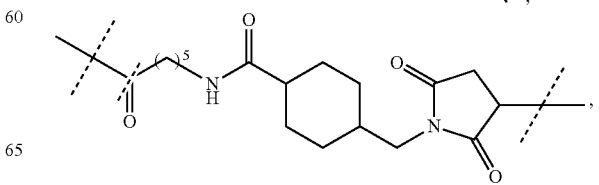

-continued

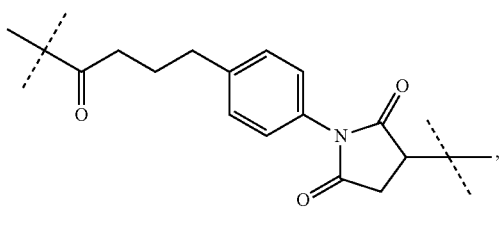

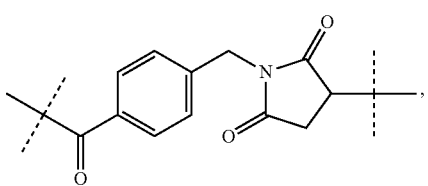
and

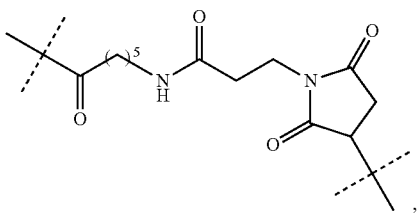

when the functional group represents a thiol group,
and among:

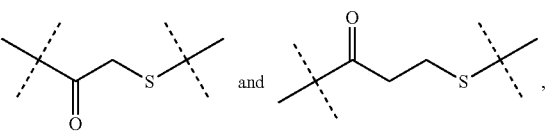

when the functional group represents a maleimide group or a halogen atom.

In another preferred embodiment, the linker is

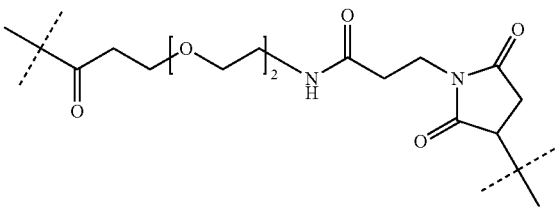

In a preferred embodiment, the linker will be chosen among:

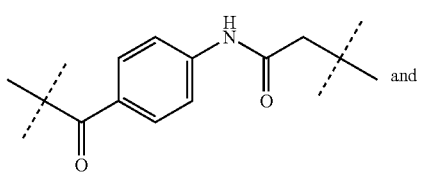

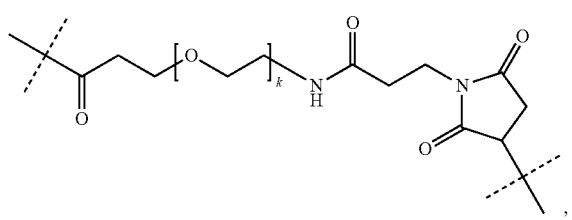

with k representing an integer comprised between 2 and 24, and being advantageously 2, 4, 8 or 12, and The term "O-protecting group" has the same meaning as defined above. Advantageously it is a methyl, benzyl or p-methoxybenzyl group.

It is preferable that the polyanion is not too long, nor bears 3-O-sulfate groups on the uronic moieties, as it would have anticoagulant activity, not desirable in this invention, and would form aspecific bonds with various proteins, namely thrombin and antithrombin III. The polyanion has preferably a degree of polymerisation dp of 2 to 24, advantageously 4 to 18, preferably 4 to 14. The polyanion has preferably at least two anionic groups per disaccharide.

Heparin dodecasaccharide ($HP_{12}$) and tetrasaccharide ($HP_4$) can be cited as examples, and in particular $HP_{12}$.

Advantageously, the functional group is a thiol group.

In a particular embodiment, the GP''' groups are identical.

Advantageously, these GP''' groups are methyl or benzyl groups.

In a preferred embodiment, the polyanion carrying the functional group is chosen among:

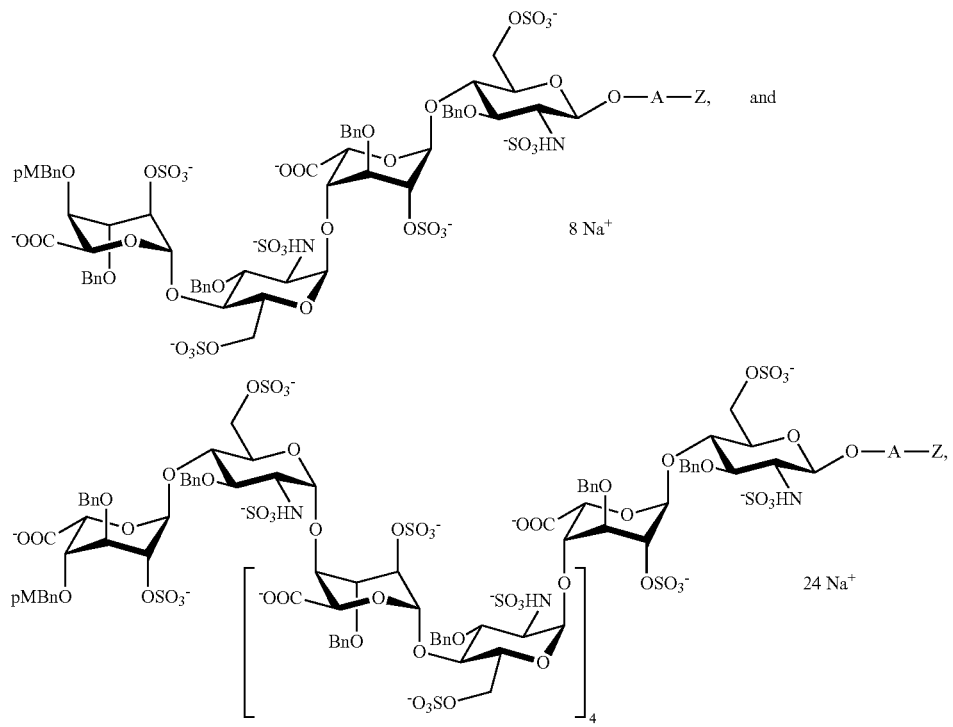

with:

A representing a group chosen among those of formula:
—(CH$_2$)$_p$—NH—CO—(CH$_2$)$_q$—, —(CH$_2$—CH$_2$)—(O—CH$_2$—CH$_2$)$_p$—NH—CO—(CH$_2$)$_q$—, —(CH$_2$)$_p$—NH—CO—(CH$_2$—CH$_2$—O)$_q$—(CH$_2$—CH$_2$)— or —(CH$_2$—CH$_2$)—(O—CH$_2$—CH$_2$)$_p$—NH—CO—(CH$_2$—CH$_2$—O)$_q$—(CH$_2$—CH$_2$)—, wherein p represents an integer comprised between 1 and 10 and q represents an integer comprised between 1 and 10, and Z representing a halogen atom, a thiol or a maleimide group.

Advantageously, A represents a group of formula —(CH$_2$)$_5$—NH—CO—(CH$_2$)$_2$—.

Advantageously, Z represents a thiol group.

In a preferred embodiment, the organic molecule will be chosen among:

(compound 20)

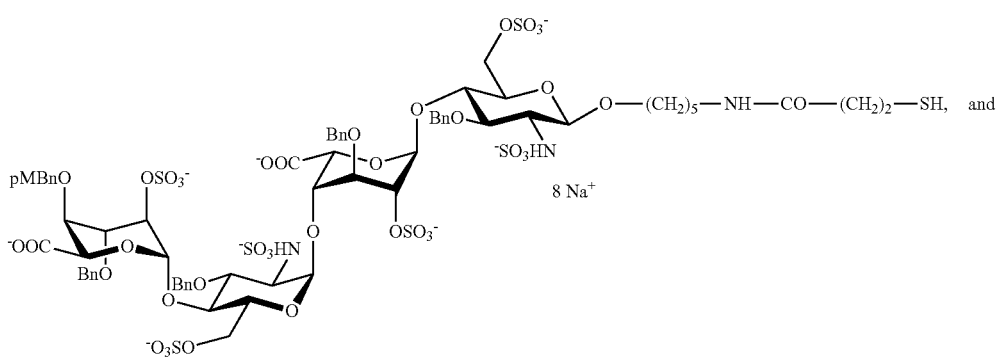

(compound 21)

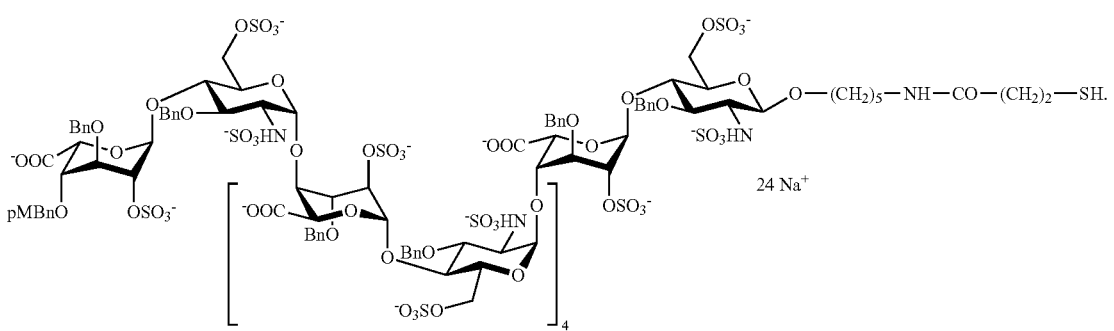

In another particular embodiment, the conjugated molecule of the invention is chosen among the following molecules:
(compound 23)
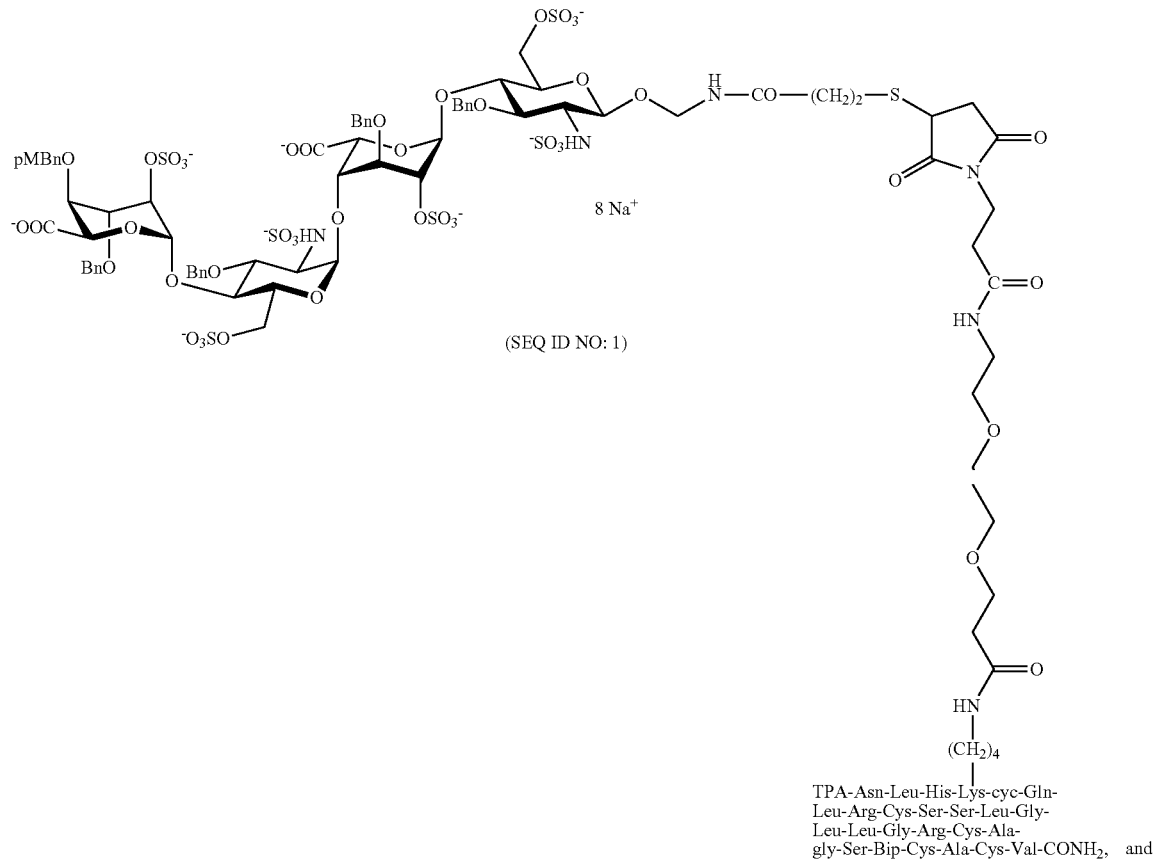
(SEQ ID NO: 1)
TPA-Asn-Leu-His-Lys-cyc-Gln-
Leu-Arg-Cys-Ser-Ser-Leu-Gly-
Leu-Leu-Gly-Arg-Cys-Ala-
gly-Ser-Bip-Cys-Ala-Cys-Val-CONH$_2$, and
(compound 24)
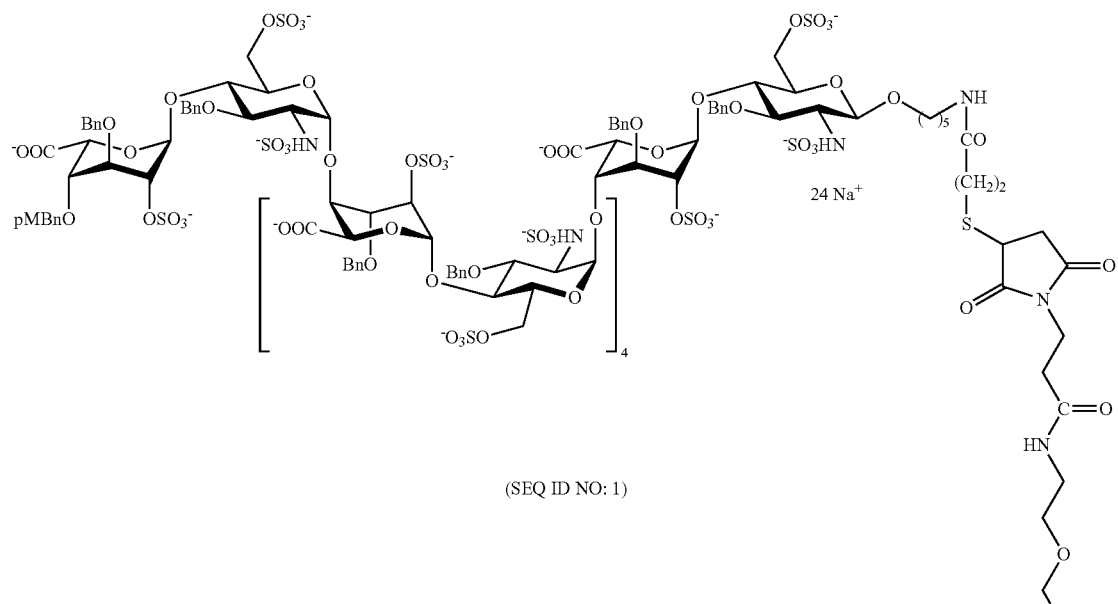
(SEQ ID NO: 1)

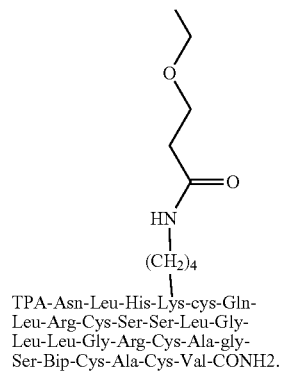

TPA-Asn-Leu-His-Lys-cys-Gln-
Leu-Arg-Cys-Ser-Ser-Leu-Gly-
Leu-Leu-Gly-Arg-Cys-Ala-gly-
Ser-Bip-Cys-Ala-Cys-Val-CONH2.

According to a third aspect, the invention covers a conjugated molecule as defined above for its use as medicament, and in particular, for the treatment of AIDS.

The use of a conjugated molecule as defined above for the manufacture of a medicament for an antiviral treatment, and in particular for the treatment of AIDS, is also an object of the present invention.

The invention also concerns an antiviral treatment method, preferably an anti-AIDS treatment method, comprising the administration to a patient in need thereof of a conjugated molecule according to the invention.

According to a fourth aspect, the invention covers a pharmaceutical composition comprising a conjugated molecule as defined above and a pharmaceutically acceptable vehicle.

In the pharmaceutical compositions of the present invention for oral, intranasal, sublingual, subcutaneous, intramuscular, intravenous, transdermal, local or rectal administration, the active ingredient can be administered in unit forms for administration, mixed with conventional pharmaceutical carriers, to animals or to humans. Suitable unit forms for administration comprise the forms for oral administration, such as tablets, gelatin capsules, powders, granules and oral solutions or suspensions, the forms for sublingual and buccal administration, the forms for subcutaneous, intramuscular, intravenous, intranasal or intraoccular administration and the forms for rectal administration.

According to a fifth aspect, the invention covers a process for the preparation of a conjugated molecule as defined above, characterized in that the process comprises the following steps:
  a. contacting the peptide derived from the CD4 receptor of general sequence (I) as defined above with a bifunctional compound carrying two active groups, so that one of the two active groups forms a covalent bond with the free amino group (—NH$_2$) of the residue of the amino acid Lys present in general sequence (I), in order to obtain an activated peptide carrying the second active group of the bifunctional group, and
  b. contacting the activated peptide obtained at step (a) with an organic molecule carrying a functional group as defined above or with an organic molecule corresponding to the organic molecule defined above carrying a thiol group for which the thiol group (SH) has been protected by a protective thiol group, so that the active group of the activated peptide forms a covalent bond with the functional group, protected or not, of the organic molecule, in order to obtain the conjugated molecule.

Thus, the functional group refers to a halogen atom, a maleimide, a thiol or a protective thiol group.

The compound obtained at step (a) will be called indifferently, in the present application, "activated peptide", "activated miniCD4", "activated CD4 peptide" or "activated miniCD4 peptide".

The term "protective thiol group", as used in the present invention refers to a sulfur atom substituted by a S-protecting group in order to protect a thiol group against undesirable reactions during synthetic procedures. Commonly used S-protecting groups are disclosed in Greene, "Protective Groups In Organic Synthesis," (John Wiley & Sons, New York (1981)). S-protecting groups comprise benzyl ethers, substituted or not, such as p-methoxybenzyl or p-nitrobenzyl, trityl ethers, thioethers, thioacetate or thioacetal.

Advantageously, the protected thiol group is a thioacetyl.

When the organic compound carries a protective thiol group, said protective group will be deprotected before or during step (b), in order to recover a free thiol group and to allow the coupling of this thiol with the active group of the activated peptide.

The characteristics of the peptide derived from CD4 receptor are the same as defined above.

In particular, P3 comprises preferably at least one basic amino acid, said basic amino acid being even more preferably arginine.

According to a preferred embodiment, Xaa$^f$ represents TPA in general sequence (I).

According to another preferred embodiment, Xaa$^1$ represents Phe.

Preferably, the sequence of the peptide derived from the CD4 receptor of general sequence (I) is chosen from the group consisting of sequences SEQ ID No. 1 and SEQ ID No. 2, advantageously SEQ ID No. 1.

The term "bifunctional compound" in this patent application refers to any compound incorporating two active groups wherein one of the two active groups is capable of forming a covalent bond with the free amino group (—NH2) of the residue of the amino acid Lys present in general sequence (I) and the other active group is capable of forming a covalent bond with the organic molecule.

The person skilled in the art knows well the bifunctional compounds which can be used within the framework of this invention. Namely, the bifunctional compound according to this invention can be chosen from the following non-limiting list: NHS-PEO$_n$-Maleimide where n is comprised between 2 and 24, advantageously n=2, 4, 8 or 12, Sulfo-KMUS (N-[k-maleimidoundecanoyloxy]sulfosuccinimide ester), LC-SMCC (succinimidyl-4-[N-maleimidomethyl]cyclohexane-1-carboxy-[6-amidocaproate]), KMUA (N-k-maleimidoundecanoic acid), SMPB (succinimidyl 4-[p-maleimidophenyl]butyrate), Sulfo-SMPB (sulfosuccinimidyl 4-[p-maleimidophenyl]butyrate), Sulfo-SIAB (N-sulfosuccinimidyl[4-iodoacetyl]aminobenzoate), SIAB (N-succinimidyl[4-iodoacetyl]aminobenzoate), Sulfo-EMCS ([N-e-maleimidocaproyloxy]sulfosuccinimide ester), EMCA (N-e-maleimidocaproic acid), ([N-e-maleimidocaproyloxy]succinimide ester), SMCC (succinimidyl 4-[N-maleimidomethyl]cyclohexane-1-carboxylate), Sulfo-SMCC (sulfosuccinimidyl 4-[N-maleimidomethyl]cyclohexane-1-carboxylate), MBS (m-maleimidobenzoyl-N-hydroxy succinimide ester), Sulfo-MBS (m-maleimidobenzoyl-N-hydroxysulfosuccinimide ester), GMBS (N-[g-maleimidobutyryloxy]succinimide ester), Sulfo-GMBS (N-[g-maleimidobutyryloxy]sulfosuccinimide ester), SPDP (N-succinimidyl-3-(2-pyridyldithio)propionate), SBAP (succinimidyl 3-[bromoacetamido]propionate), BMPS (N-[[beta]-maleimidopropyloxy]succinimide ester), BMPA (N-[beta]-maleimidopropionic acid), N-(a-maleimidoacetoxy) succinimide ester), SIA (N-succinimidyl iodoacetate), SMPH (succinimidyl-6-[betamaleimidopropionamido]hexanoate), SATA (N-succinimidyl-S-acetylthioacetate) and SATP (N-succinimidyl-S-acetylthiopropionate).

According to the invention, NHS-PEO$_n$-Maleimide wherein n=2 is also called succinimidyl-[(N-maleimidoproprionamido)-diethyleneglycol]ester, NHS-PEO$_n$-Maleimide wherein n=4 is also called succinimidyl-[(N-maleimidoproprionamido)-tetraethyleneglycol]ester, NHS-PEO$_n$-Maleimide wherein n=8 is also called succinimidyl-[(N-maleimidoproprionamido)-octaethyleneglycol]ester, NHS-PEO$_n$-Maleimide wherein n=12 is also called succinimidyl-[(N-maleimidoproprionamido)-dodecaethyleneglycol]ester.

The active group capable of forming a covalent bond with the free amine group (—NH$_2$) of the residue of amino acid Lys present in general sequence (I) can be any active ester group.

Preferably, the active group capable of forming a covalent bond with the free amine group (—NH$_2$) of the residue of amino acid Lys present in general sequence (I) is the active group N-hydroxysuccinimide ester (NHS) or N-hydroxy-4-sulfo-succinimide ester, and advantageously is the NHS active group.

Even more preferably, the two active groups of the bifunctional compound are different (heterobifunctional group) and one of the two groups is the NHS active group or a N-hydroxy-4-sulfo-succinimide ester, and advantageously is the NHS active group.

Advantageously, the active group of the bifunctional compound, capable of forming a covalent group with the functional group of the organic molecule, is a halogen atom or a maleimide group when the functional group of the organic molecule is a thiol or a protective thiol group and is a thiol or a protective thiol group, as defined above, when the functional group of the organic molecule is a halogen atom or a malimide group.

According to a preferred embodiment, when the functional group of the organic molecule is a thiol group or a protective thiol group, the bifunctional compound is chosen from the group consisting of succinimidyl-6-[beta-maleimidopropionamido]hexanoate (SMPH) and NHS-PEO$_n$-maleimide, n being comprised between 2 and 24, and advantageously is 2, 4, 8 or 12.

According to a particularly preferred embodiment, the bifunctional compound is SMPH.

The molecular structure of SMPH is as follows:

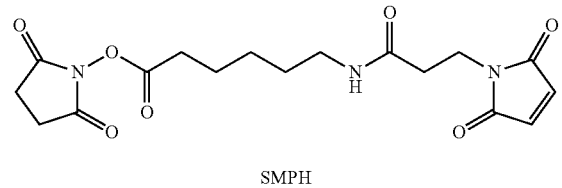 [SMILES: O=C(CCN1C(=O)C=CC1=O)NCCCCCC(=O)ON1C(=O)CCC1=O]

SMPH

According to yet another particularly preferred embodiment, the bifunctional compound is succinimidyl-[(N-maleimidopropionamido)-diethyleneglycol]ester, also called NHS—PEO$_2$-maleimide, succinimidyl-[(N-maleimidopropionamido)-tetraethyleneglycol]ester, also called NHS—PEO$_4$-maleimide, succinimidyl-[(N-maleimidopropionamido)-octaethyleneglycol]ester, also called NHS—PEO$_8$-maleimide, succinimidyl-[(N-maleimidopropionamido)-dodecaethyleneglycol]ester, also called NHS—PEO$_{12}$-maleimide, still more preferably the bifunctional compound is NHS—PEO$_2$-maleimide.

The molecular structure of NHS—PEO$_2$-maleimide is as follows:

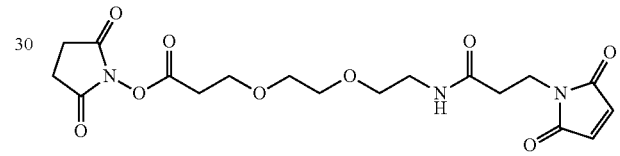

According to another particularly preferred embodiment, when the functional group of the organic molecule is a halogen atom or a maleimide group, the bifunctional compound is chosen from the group consisting of N-succinimidyl-S-acetylthioacetate (SATA) and N-succinimidyl-S-acetylthiopropionate (SATP).

The molecular structure of SATA is as follows:

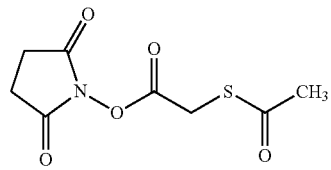

The molecular structure of SATP is as follows:

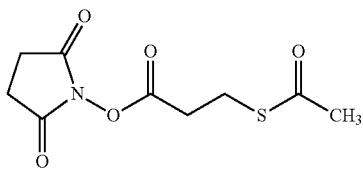 [SMILES: CC(=O)SCCC(=O)ON1C(=O)CCC1=O]

The bifunctional compounds can be obtained from PIERCE (Rockford, Ill.).

Preferably again, the process according to the invention includes a preliminary stage for the preparation of the peptide derived from the CD4 receptor of general sequence (I), when Xaa$^f$ represents TPA, wherein the process comprises, when Xaa$^f$ represents TPA in the sequence (I) of the peptide derived from the CD4 receptor, a preliminary step for the preparation of the said peptide consisting of contacting the peptide derived from the CD4 receptor of the following general sequence (III):

```
                                            (SEQ ID NO: 5)
P1-Lys-Cys-P2-Cys-P3-Cys-Xaaᵍ-Xaaʰ-Xaaⁱ-Xaaʲ-

Cys-Xaaᵏ-Cys-Xaaˡ-Xaaᵐ,   (III)
``` where P1 to P3 and Xaa$^g$ to Xaa$^m$ are as defined in general sequence (I), with N-succinimidyl-3-(2-pyridyldithio)propionate (SPDP) in order to incorporate TPA at the N-terminus of said peptide derived from the CD4 receptor of general sequence (III).

The molecular structure of SPDP is as follows:

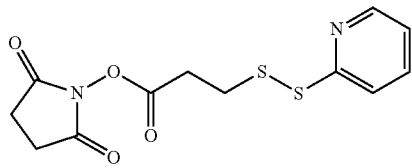 [SMILES: O=C(CCSSc1ccccn1)ON1C(=O)CCC1=O]

Moreover, as examples of active groups capable of coupling to an organic molecule by means of a covalent bond, the following groups can be cited: maleimide or bromoacetyl, S—S-pyridinium of thioacetyl.

When miniCD4 is activated by a protected thiol group (e.g. thioacetyl), it is possible to carry out coupling to an organic molecule which carries a maleimide group for example. This is possible when the functionalisation of the polyanionic polysaccharide by a thiol group or protected thiol group, such as thioacetyl, poses a problem. This then called "reverse coupling".

Preferably, the active group is the maleimide group.

The molecular structure of the activated peptide according to the invention whose active group is maleimide is the following when SMPH is the bifunctional compound used:

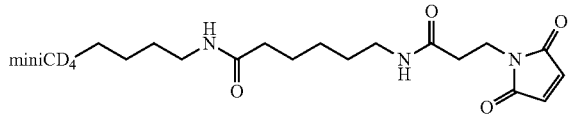

In this application, the term "SMPH activated miniCD4 peptide" refers to an activated peptide according to the invention whose amino acid Lys residue is covalently bound, advantageously by an amine bond, to a maleimide active group via a linker derived from SMPH.

According to another advantageous embodiment, the molecular structure of the activated peptide according to the invention whose active group is the maleimide group is the following when NHS—PEO$_2$-maleimide is the bifunctional compound used:

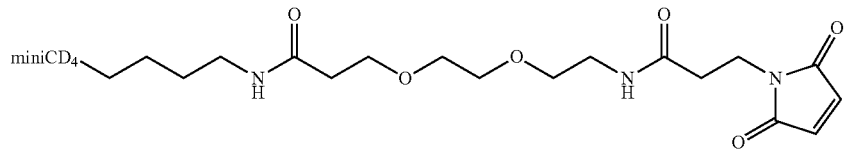

In this application, the term "maleimide activated miniCD4 peptide via a PEO$_2$ linker" refers to an activated peptide according to the invention whose amino acid Lys residue is covalently bound, advantageously by an amine bond, to a maleimide active group via a PEO$_2$ linker.

According to another preference, the active group is the thioacetyl group.

For example, the molecular structure of the activated peptide according to this invention whose active group is the thioacetyl group is the following when SATA is the bifunctional compound used:

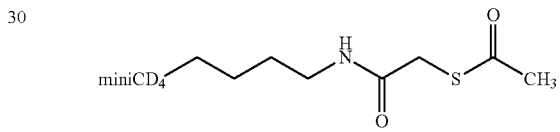

Similarly, the molecular structure of the activated peptide according to this invention whose active group is the thioacetyl group is the following when SATP is the bifunctional compound used:

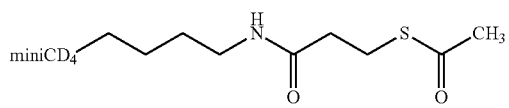

The thioacetyl group is a protected form of the thiol group. To deprotect the thiol group, we use hydroxylamine for example. This step is carried out simultaneously to coupling to the maleimide group carried by the organic molecule.

In this application, the terms "SATA activated miniCD4 peptide" and "SATP activated miniCD4 peptide" refer to an activated peptide according to the invention whose amino acid Lys residue is covalently bound, advantageously by an amine bond, to a protected thiol group (e.g. thioacetyl) via a linker derived from SATA or SATP.

Thus, according to a particular embodiment, the active group of the activated peptide is the maleimide group and the organic molecule carries a thiol or thioacetyl group.

The molecular structure of a conjugated molecule according to the invention, including a peptide derived from the CD4 receptor of general sequence (I) coupled to a modified polyanion carrying a thiol or protected thiol group, such as a thioacetyl group, is as follows when SMPH was used as bifunctional compound for the coupling:

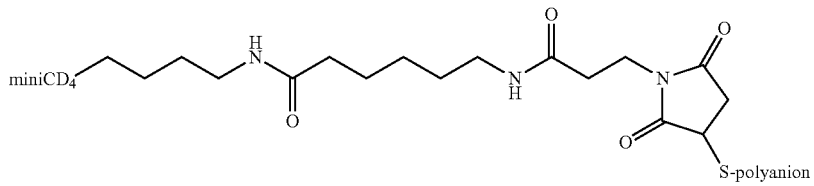

It can also be the following conjugated molecule when NHS—PEO$_2$-maleimide is the bifunctional compound used:

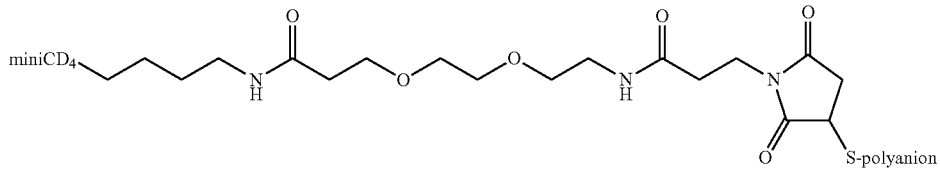

According to another embodiment, the conjugated molecule according to the invention comprises a peptide derived from the CD4 receptor comprising or consisting of general sequence (I), preferably sequence SEQ ID No. 1, and an organic molecule carrying a maleimide or halogen group.

According to another particular embodiment, the active group of the activated peptide is the thioacetyl group and the organic molecule carries a maleimide or halogen group.

For example, the molecular structure of such a conjugated molecule including a peptide derived from the CD4 receptor of general sequence (I) coupled to an organic molecule carrying a maleimide group is as follows when SATA is used for the coupling:

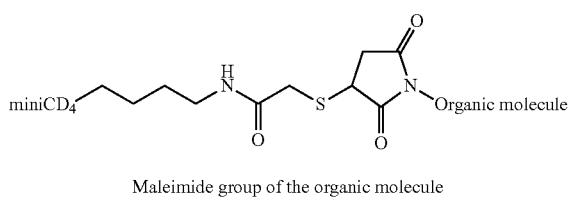

Maleimide group of the organic molecule

According to the invention, the polyanionic saccharide (the organic molecule of the present invention) can be prepared by partial depolymerisation of heparin (HP) or heparane sulphate using an enzyme method, for example by means of heparinase, or chemical method, for example by means of nitrous acid. When they are obtained chemically, the heparans can be defined by the presence of N-sulphated or N-acetylated glucosamine or nonsubstituted in position N bound to uronic acid (glucuronic acid or iduronic acid) with a varying proportion of sulphate. Structural analogues of these oligosaccharides can be obtained by chemical synthesis.

There are many advantages of such a synthetic approach compared to conjugation of recombinant compounds or those from natural sources. Within the framework of therapeutic usage, synthetic compounds are always preferable as, in addition to a fully defined structure, contamination by pathogens can be avoided, especially prion proteins in the case of HP fragments. Moreover, synthetic HP fragments are much more homogeneous than their natural equivalents. For example, synthetic HP$_{12}$ is totally devoid of 3-O-sulphate groups which are responsible for heparin's antithrombin activity.

In particular, the organic molecule of formula (II) can be synthesised according to a method analogue to the one described in Lubineau et al. (Chem. Eur. J. 2004, 10, 4265-4282) and Noti et al. (Chem. Eur. J. 2006, 12, 8664-8686).

The operating conditions for the processes according to the invention for preparation of the activated peptide and conjugated molecule are well known to the person skilled in the art and can be adapted if necessary.

The examples and figures below illustrate the invention but do not limit its scope in any way.

FIGURES

FIG. 1: Diagram illustrating the biological action of the conjugated molecules of the invention.

FIG. 2: miniCD4 and gp120 interaction

Affinity of synthesized miniCD4 for gp120 was evaluated by Biacore. The results confirm that miniCD4, "designated" by the inventors, with a single lysine is a functional analogue of CD4 protein.

Top: gp 120 binding to mCD4 surface; for the chip preparation, a biotin was attached to the Lys side chain of mCD4.

Middle: gp120 binding to sCD4 surface was inhibited by nM concentration of mCD4

Bottom: In the absence of mCD4, gp120 does not bind to mAb 17b (mAb which interact with CD4i epitope and which is used as a co-receptor surrogate). This experiment shows that mCD4 induced the exposition of the CD4i epitope since mCD4 in complex with gp120 promotes gp120 binding to mAb 17b surface FIG. 3: Diagram for synthesis of maleimide activated miniCD4 peptide via PEO2 linker FIG. 4: Diagram representing the binding of gp120 (YU2 or MN) to CD4. The gp120 were injected over the CD4 surface either alone (light line) or bound to either mCD4 (heavy line, upper panels) or covalently linked mCD4-HS12Lb (25) (heavy line, lower panels)

Figure 5:
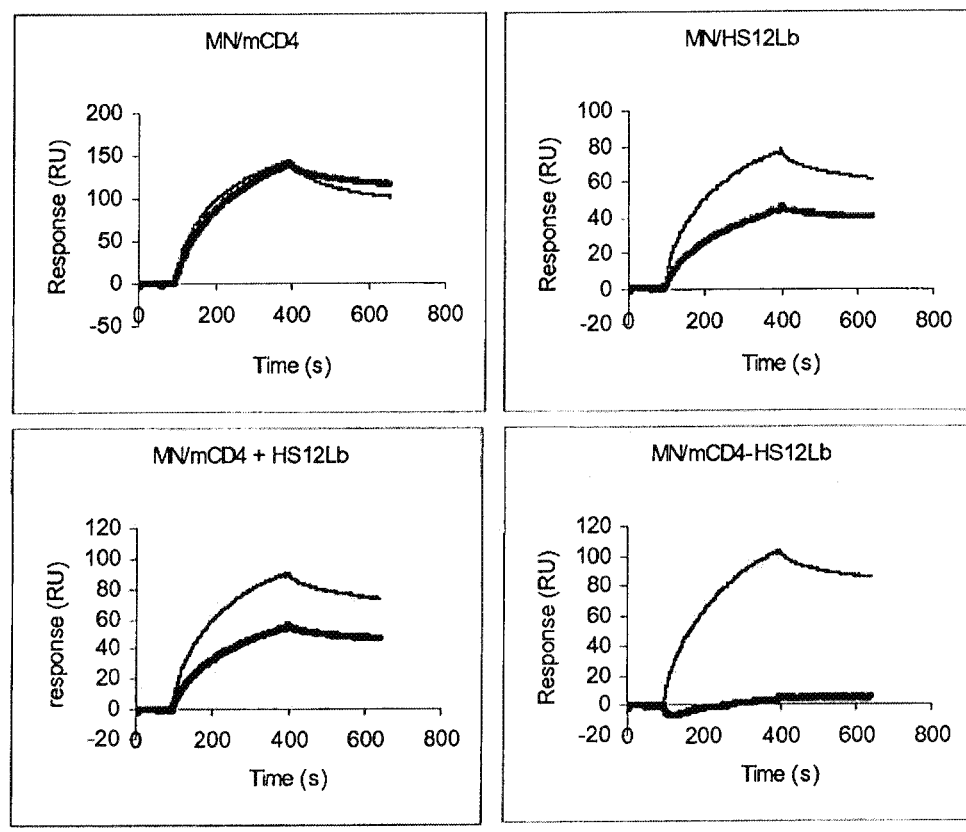

FIG. 5: Diagram representing the binding of gp120 (MN) to HS. The gp120 were injected over the HS surface either alone (light line) or bound to either mCD4 (heavy line, upper left panel), HS12Lb (19) (heavy line, upper right panel), mCD4 and HS12Lb non covalently linked (heavy line, lower left panel) or covalently linked mCD4-HS12Lb (25) (heavy line, lower right panel)

Figure 6:
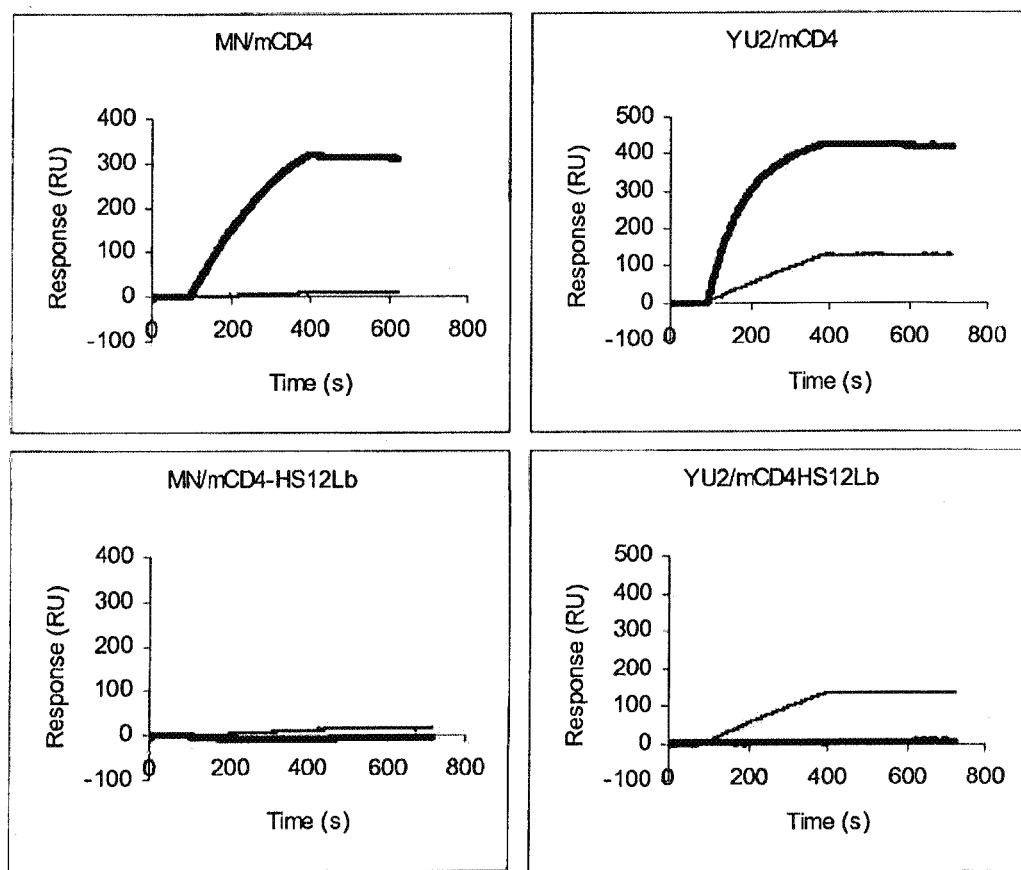

FIG. 6: Diagram representing the binding of gp120 (YU2 or MN) to mAb 17b. The gp120 were injected over the mAb 17b surface either alone (light line) or bound to either mCD4 (heavy line, upper panels), or covalently linked mCD4-HS12Lb (25) (heavy line, lower panels)

Figure 7:
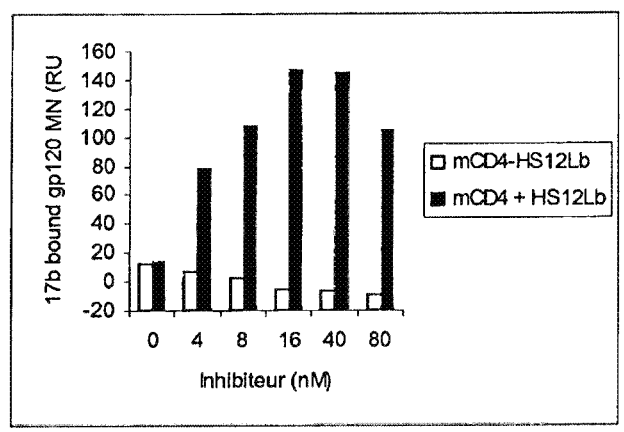
Figure 7:
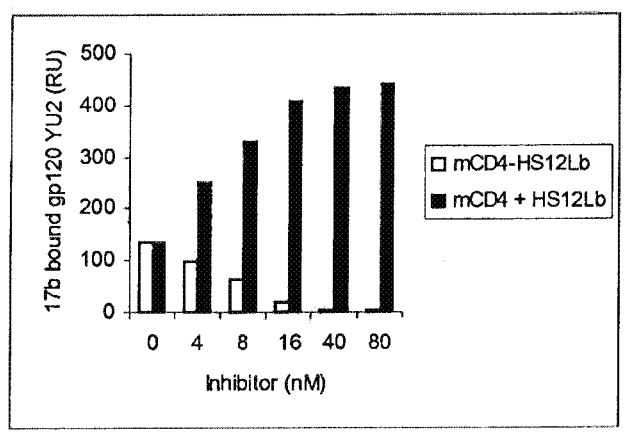

FIG. 7: Diagram representing the binding of gp120 MN (top) or YU2 (bottom) to mAb 17b. The gp120 were injected over the mAb 17b surface with increasing concentration of either non covalently linked mCD4 and HS12Lb (19) (black) or covalently linked mCD4-HS12Lb (25) (white).

Figure 8:
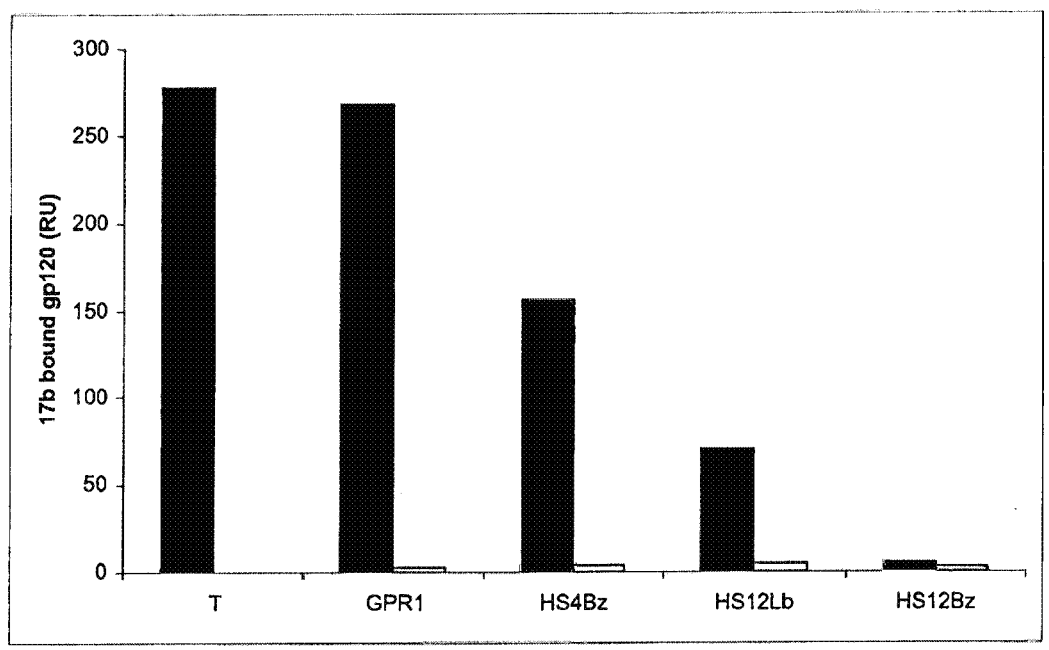

FIG. 8: Diagram representing the binding of gp120 to mAb 17b. The gp120 was injected over the mAb 17b surface with mCD4 (T) or mCD4 and GPR1, HS4Bz (17), HS12Lb (19), HS12Bz (18) either non covalently linked (black) or covalently linked (white).

FIG. 9. The mCD4-$HS_{12}$ (3) binds to gp120 unmasks and blocks the gp120 coreceptor binding site. Overlay of sensorgrams showing the binding of mCD4-$HS_{12}$ (25), at (from top to bottom) 76, 51, 37, 22, 15 and 10 nM, to immobilized YU2 (a) or MN (b) gp120. mCD4 (black) or mCD4-$HS_{12}$ (25) (bold) were injected for 5 mins (100 to 400 s) at 200 nM over a YU2 (c,e) or MN (d,f) activated sensorchip, after which mAb 17b (c,d) or mAb E51 (e,f) were injected for a further 5 mins (400 to 700 s). The binding responses (in RU) were recorded as a function of time (in s).

Figure 10:
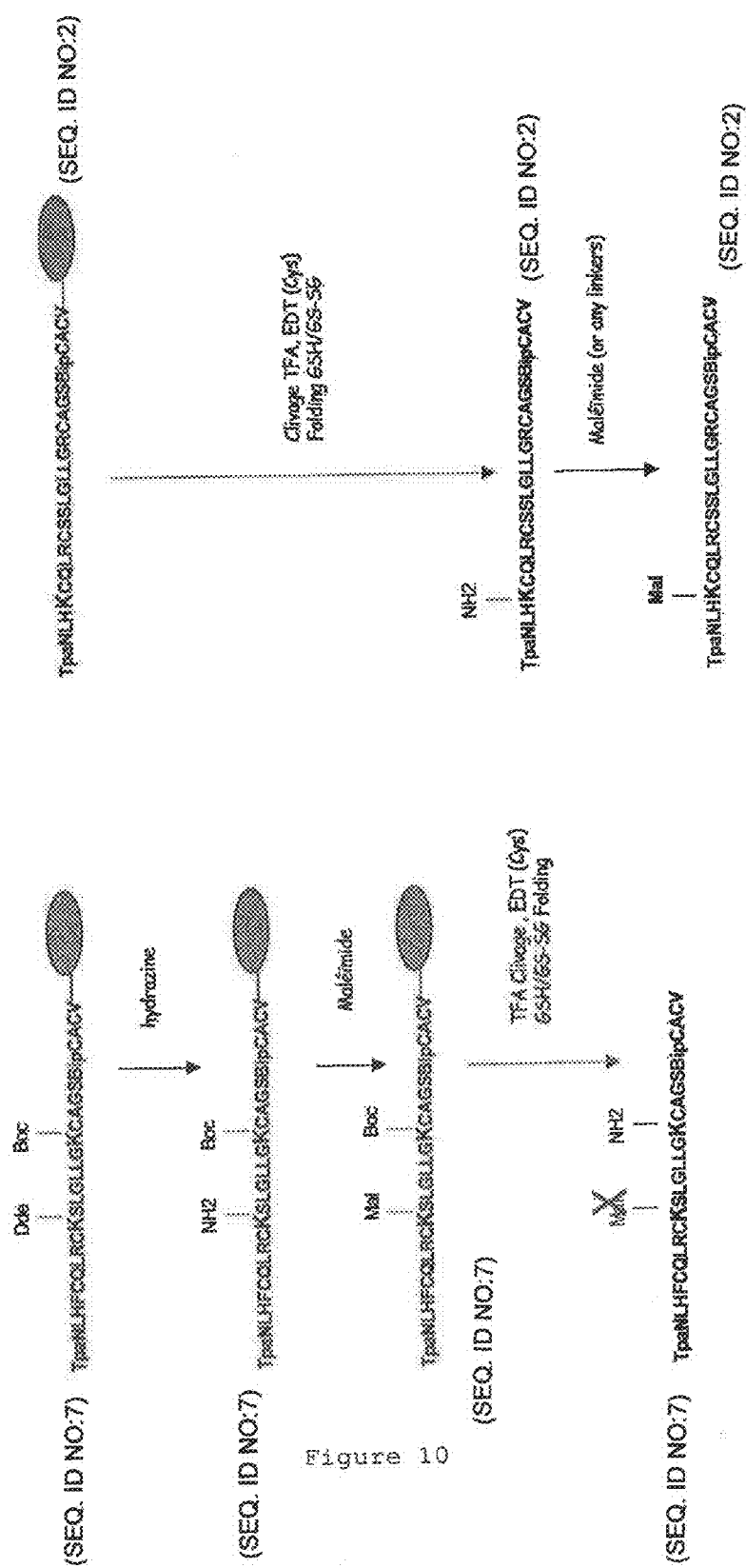

FIG. 10: Strategy of the prior art for maleimide labelling of a lysine in the case of a selected lysine within a multiple containing Lys sequence (bottom) and of a lysine within a single containing Lys sequence (top).

FIG. 11: Structure of YU2 GP120 (light grey) in complex with mCD4 (dark grey), showing that $Lys_5$ is located close to the HS binding site constituted by $R_{419}$, $K_{421}$ and $K_{432}$ and represents thus a more suitable attachment point for producing the HS derived oligosaccharide than $Lys_{11}$.

EXAMPLES

Example I

Synthesis Diagrams

I.1 Synthesis Diagram for the Coupling Method Between a miniCD4 Peptide and a Polyanion Mentioned in Application WO 03/089000 (Najjam S. et al., Cytokine 1997, 9 (12): 1013-1022)

Coupling of an amine group to the reducing end of a sugar

I.2. Synthesis Diagram for the Coupling Method of the Invention (Example with SMPH as Bifunctional Group)

(SEQ ID NO: 1)
TPA-Asn-Leu-His-Lys-cys-Gln-Leu-Arg-Cys-Ser-Ser-Leu-Gly-Leu-Leu-Gly-Arg-Cys-Ala-gly-Ser-Bip-Cys-Ala-Cys-Val-CONH2
        |
        NH2 miniCD4

↓ SMPH (SEQ ID NO: 1)
TPA-Asn-Leu-His-Lys-cys-Gln-Leu-Arg-Cys-Ser-Ser-Leu-Gly-Leu-Leu-Gly-Arg-Cys-Ala-gly-Ser-Bip-Cys-Ala-Cys-Val-CONH2
        |
        NH
        |
        CO—(CH2)5—NH—CO—(CH2)2—N(Maleimide)

miniCD4 activated

↓ HS—X

-continued

TPA-Asn-Leu-His-Lys-cys-Gln-Leu-Arg-Cys-Ser-Ser-Leu-Gly-Leu-Leu-Gly-Arg-Cys-Ala-gly-Ser-Bip-Cys-Ala-Cys-Val-CONH2 (SEQ ID NO: 1)

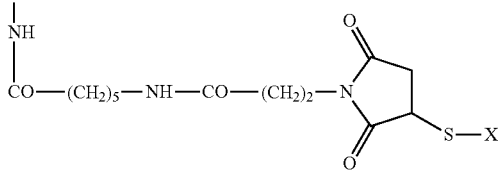

X = radical of the organic compound carrying a thiol group

The miniCD4 activation method via incorporation of the maleimide group allows coupling of any compound with a free thiol group (SH) or masked thiol group (thioacetyl for example). Thus, this activated miniCD4 allows obtaining miniCD4-heparin covalent conjugated molecules insofar as heparin (or any other polysaccharide) will have previously been derivatised by a thiol group.

Example II

Chemical Synthesis of Activated miniCD4 with SMPH or SATP

II.1 Synthesis of miniCD4

A mini-peptide CD4 was synthesized in accordance with the methodology for Fmoc solid phase peptide synthesis ("Fmoc solid phase peptide synthesis, a practical approach", edited by W. C. Chan and P. D. White, Oxford University Press, 2000) using an Applied Biosystems 433 peptide synthesizer. Starting with 0.1 mmole of amide-Fmoc resin, elongation in stages of the peptide chain was carried out by coupling 10 amino acid equivalents protected by Fmoc and activated by a HATU/DIEA mixture. The N-terminus thiopropionyl group was introduced by SPDP coupling (1.6 equivalent in DMF) on peptide-resin.

After cleaving by TFA/H$_2$O/EDT/TIS (94/2.5/2.5/1), the peptide was recovered by precipitation in cold diethyl ether. After freeze drying, the raw peptide (156 mg) was reduced overnight in DTT in a 20% acetic acid solution and purified by reverse phase MPLC on a Nucleoprep C18 column, 20 μm, 100 Å (26×313 mm) using a linear gradient 30 to 90% from B to A, over a period of 60 minutes, at a flow rate of 20 ml/min (B=80% CH$_3$CN/20% aqueous TFA at 0.08%; A=100% aqueous TFA at 0.08%). The pure fractions were collected and freeze dried. The peptide was then folded back using overnight GSH/GSSG treatment. The folded back peptide was purified by MPLC using a 20 to 80% gradient over a period of 60 minutes, giving 8.7 mg of mini-CD4. Purity (93.5%) was verified by analytic reverse phase HPLC on a Nucleosil column C18, 5 μm, 300 Å (4.6×150 mm) using a linear gradient 25 to 35% CH$_3$CN in aqueous TFA at 0.08% over a period of 20 minutes at a flow rate of 1 ml/min (retention time=15.44 minutes).

ES$^+$MS: 2896.32±0.23; expected: 2896.49; yield: 5.5%

II.2 Mini-CD4 Activated with SMPH

The maleimide group was introduced onto the lateral Lys chain of mini-CD4 by reacting 4 SMPH equivalents in phosphate buffer pH=8. The reaction was controlled by HPLC. 100% coupling is achieved after 15 minutes. After purification in a semi preparative Nucleosil C18 column for reverse phase HPLC, 5 μm, 300 Å (10×250 mm) using a linear gradient 25 to 45% CH$_3$CN in aqueous TFA at 0.08%, over a period of 20 minutes, at a flow rate of 6 ml/min, final purity (97.7%) of mini-CD4 activated with SMPH was controlled by analytic RP-HPLC using a linear gradient 25 to 45% (retention time=13.21 minutes).

ES$^+$MS: 3160.83±0.29; expected: 3160.78; yield: 1.9 mg (67%).

Final HPLC Elugram of SMPH Activated miniCD4 Peptide
About 2 mg/ml
Inj 5 μl ds 25-45
Sample name: FBX13082-190
Surface percentage ratios:
Sorted by: signal
Multiplicator: 1.0000
Dilution: 1.0000
Uses multiplicator and dilution factor with internal standard
Signal 1: DAD1 A, Sig=230.4 Ref=off

TABLE 1

| Peak no. | Retention time [min] | Type | Width [min] | Surface area [mAU*s] | Height [mAU] | Surface area % |
|---|---|---|---|---|---|---|
| 1 | 12.674 | BV F | 0.0909 | 6.52587 | 1.07449 | 0.3925 |
| 2 | 12.573 | VV | 0.0714 | 6.31252 | 1.19955 | 0.3797 |
| 3 | 12.832 | VV | 0.0909 | 8.14971 | 1.23625 | 0.4902 |
| 4 | 13.027 | VV F | 0.0859 | 16.22212 | 2.63102 | 0.9758 |
| 5 | 13.212 | VB | 0.2055 | 1625.25330 | 120.40638 | 97.7617 |
| Totals | | | | 1662.46352 | 126.54769 | |

Results obtained with improved integrator.

Mass Spectrum of SMPH Activated miniCD4 Peptide
Copy of the hypermass calculation for +Q1 MCA (10 scans): from FBX13082-190/InfMSpo/c/03/08/05
Criteria used for hypermass calculation
Agent: Mass: 1.0079, Charge: 1, Agent gained
Tolerance for charge estimation: 0.1000
Tolerance between mass estimations: 20.000

TABLE 2

| Peak | Intensity | Charge | Calculated charge | Hypermass estimation |
|---|---|---|---|---|
| 791.29 | 322500.00 | 4 | 4.00218 | 3161.12 |
| 1054.52 | 41316500.00 | 3 | 3.00218 | 3160.54 |
| 1581.43 | 7411500.00 | 2 | 1.99944 | 3160.84 |

Estimated final mass: 3160.83
Standard deviation: 0.29

II.3 Mini-CD4 Activated with SATP

The thioacetyl group was introduced onto the lateral Lys chain of mini-CD4 by reacting 1 SATP equivalent in phosphate buffer pH=8. The reaction was controlled by HPLC. 46% coupling is achieved after 3 minutes. The mini-CD4 activated by SATP was isolated on a Nucleosil C18 column for semi preparative reverse phase HPLC, 5 μm, 300 Å (10× 250 mm) using a linear gradient 20 to 40% $CH_3CN$ in aqueous TFA at 0.08% over a period of 20 minutes, at a flow rate of 6 ml/min. Final purity (100%) of mini-CD4 activated with SATP was controlled by analytic RP-HPLC using a linear gradient 25 to 45% (retention time=13.88 minutes).

$ES^+MS$: 3027.31±0.41; expected: 3027.66. This coupling reaction was carried out once and could be optimized by adding directly 2 equivalents of SATP.
Final HPLC Elugram of SATP Activated miniCD4 Peptide 25-45 in 20 minutes
Sample name: FBX13082-168-2
Surface percentage ratios:
Sorted by: signal
Multiplicator: 1.0000
Dilution: 1.0000
Uses multiplicator and dilution factor with internal standard
  Signal 1: DADI A, Sig=230.4 Ref=off

TABLE 3

| Peak no. | Retention time [min] | Type | Width [min] | Surface area [mAU*s] | Height [mAU] | Surface area % |
|---|---|---|---|---|---|---|
| 1 | 13.883 | VV | 0.1668 | 520.71381 | 46.44330 | 100.0000 |
| | Totals | | | 520.71381 | 46.44330 | |

Results obtained with improved integrator.

Mass Spectrum of SATP Activated miniCD4 Peptide
Copy of the hypermass calculation for +Q1 MCA (10 scans): from FBX13082-186-2/Infpo/c/29/07/05
Criteria used for hypermass calculation
Agent: Mass: 1.0079, Charge: 1, Agent gained
Tolerance for charge estimation: 0.1000
Tolerance between mass estimations: 20.000

TABLE 4

| Peak | Intensity | Charge | Calculated charge | Hypermass estimation |
|---|---|---|---|---|
| 757.72 | 125000.00 | 4 | 3.99687 | 3026.85 |
| 1010.22 | 45016000.00 | 3 | 2.99687 | 3027.64 |
| 1514.73 | 23987000.00 | 2 | 2.00039 | 3027.45 |

Estimated final mass: 3027.31
Standard deviation: 0.41

Example III

Relevance of Choice of General Sequence (I) Including One and Only One Lysine Residue in a Defined Position Relevance of the choice of general sequence (I) including one and only one lysine residue in a defined position was validated by synthesis of a miniCD4 peptide derivatised on Lys by (PEO)4-Biotin using EZ-Link-NHS-(PEO) 4-Biotin PIERCE reagent (Rockford, Ill.).
Introduction of this Biotin derivative in a defined position in general sequence (I) does not modify binding of gp120 to miniCD4 (see Biacore measurement of FIG. 2).
The various synthesis processes were not optimised. It should be possible to achieve better yields.

Example IV

Figure 3:
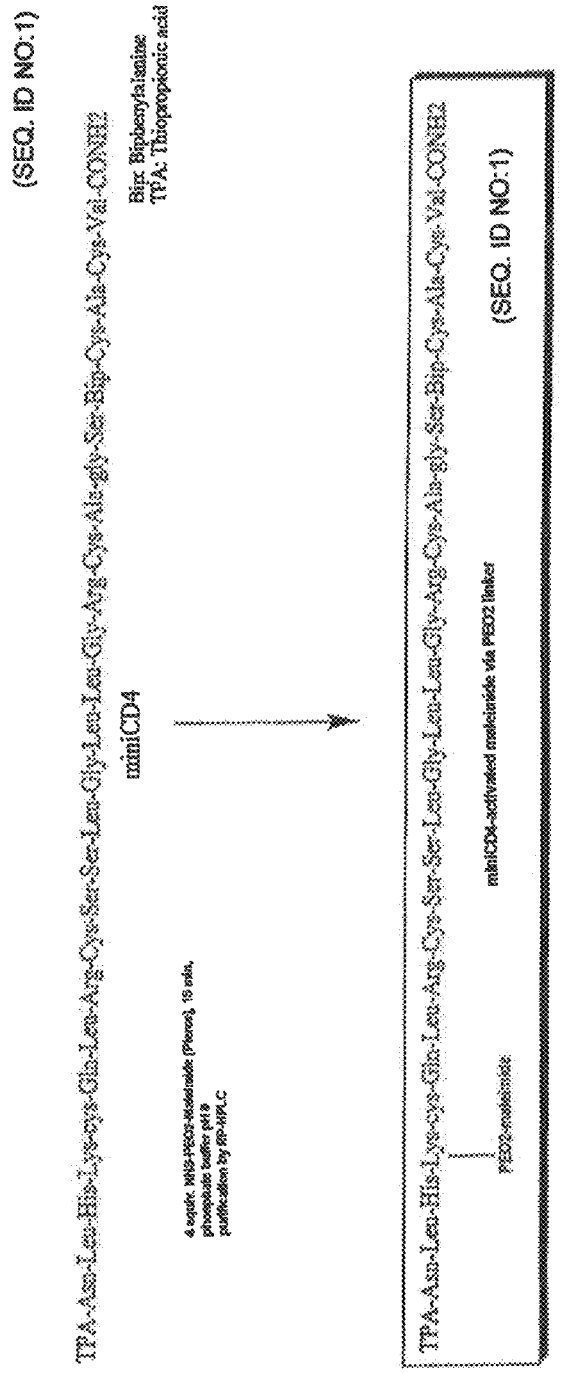
Figure 3:
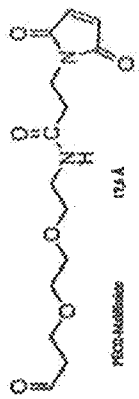
Figure 4:
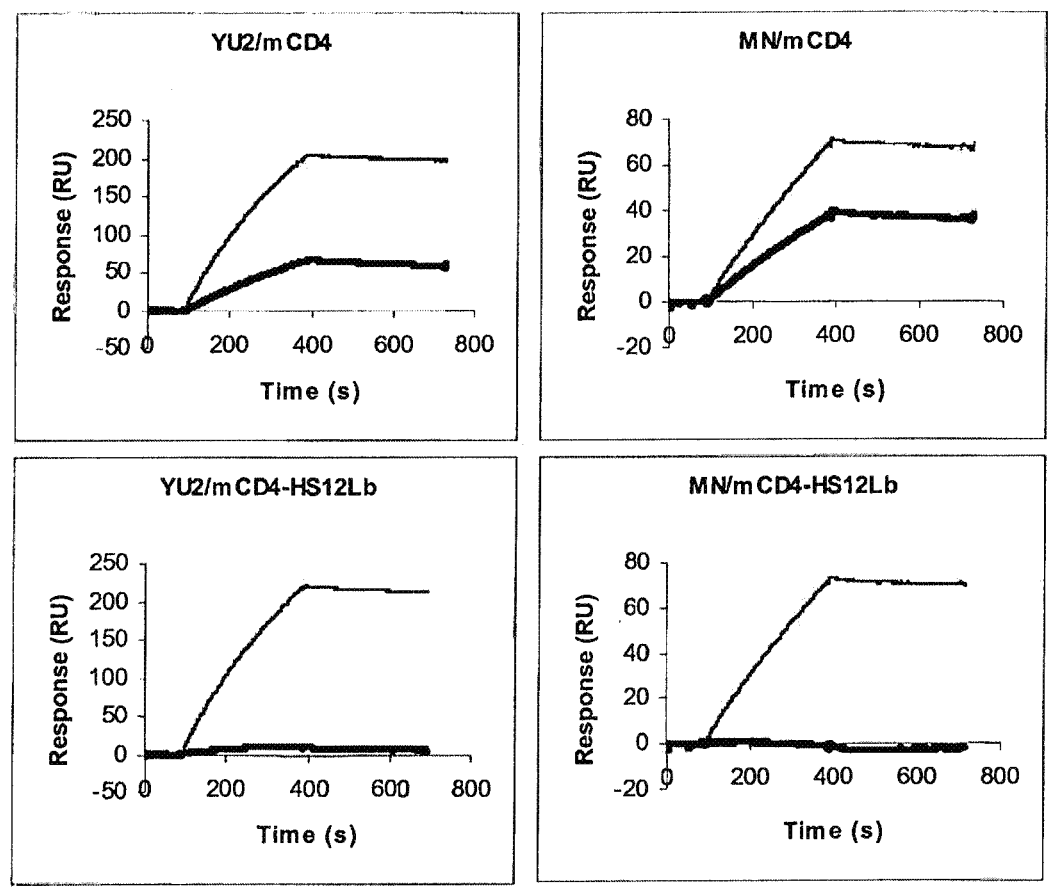

Chemical Synthesis of Maleimide Activated mini-CD4 via a $PEO_2$ Linker (miniCD4-$PEO_2$-mal) (see FIG. 3)

mCD4-$PEO_2$-maleimide differs from the compound mCD4-SMPH in terms of the type of linker. For reasons of solubility, a polyethylene oxide ($PEO_2$) linker which is more hydrophilic was incorporated between miniCD4 and the maleimide group.
Synthesis:
A solution of 10 mg of mCD4 (MW: 2897; 3.4 mmoles) in 1 ml of $H_2O$ was diluted in 1 ml of phosphate buffer 0.1 M pH 8. 4.5 mg of NHS—$PEO_2$-Maleimide (MW: 325; 13.8 mmoles; 4 equiv) were added to this cloudy solution in 20 μl of DMSO with stirring. After 10 minutes, 85% (HPLC) of the starting materials was converted into maleimide derivative. Because of the low stability of the maleimide group at pH 8, the coupling reaction was directly loaded onto a SepaK C18 column calibrated with 10% $CH_3CN$ in aqueous TFA 0.08%. The maleimide derivative was eluted with 50% $CH_3CN$. After freeze drying, the compound was then purified on a semi preparative column. Yield: 5.2 mg (48%), final purity: 77%.
ES+: 3205.3938 (expected monoisotopic M: 3205.4211), QTOF Micro Waters MaxEnt1.
HPLC conditions:
Analytic: Nucleosil 5 C18 300 Å (4.6×150 mm); linear gradient 25 to 45% $CH_3CN$ in 0.08% aqueous TFA in 20 minutes at a flow rate of 1 ml/min. Detection: 230 nm. mCD4 Rt=10.7 minutes; mCD4-PEO2-Mal Rt=12.8 minutes.
Semi preparative: Nucleosil 5 C18 300 Å (10×250 mm); linear gradient 25 to 45% $CH_3CN$ in 0.08% aqueous TFA for 20 minutes at a flow rate of 6 ml/min.
Detection: 230 nm. mCD4-PEO2-Mal Rt=11.4.

Example V

Chemical Synthesis of Conjugated Molecules of the Invention

V.1. Synthesis Diagrams

Scheme 1: Introduction of a protected amino linker on the disaccharide building block 1 (m = 5).

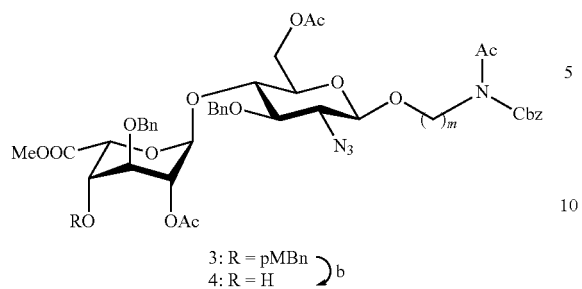
a) TMSOTf, 4 Å, CH$_2$Cl$_2$, -40 to -10° C., 79% (α/β:2/8). b) TFA, CH$_2$Cl$_2$, RT, 93%.
Scheme 2: Synthesis of protected oligosaccharide 5, 8 and 10.
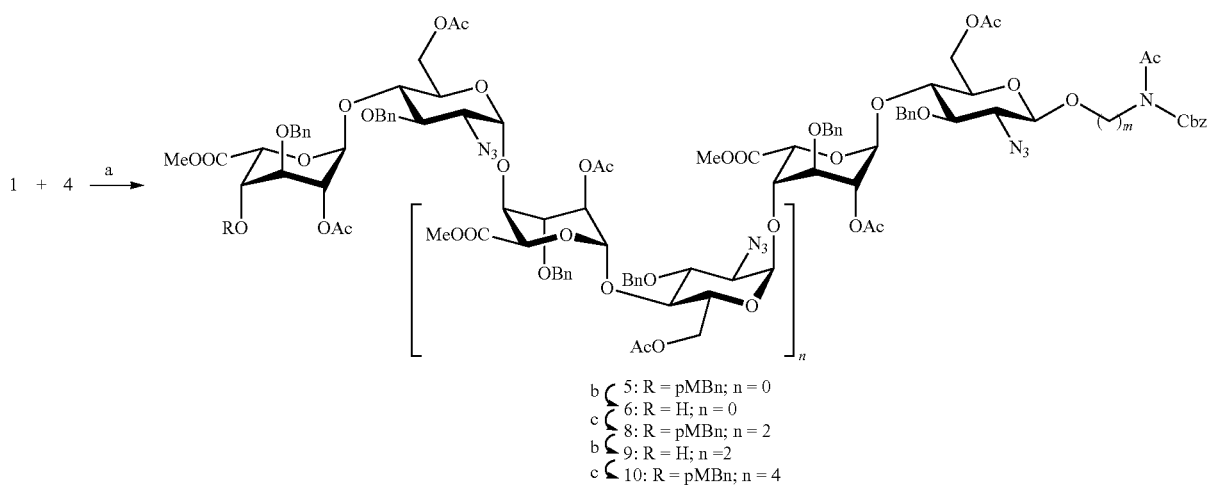
b $\{$ 5: R = pMBn; n = 0
c $\{$ 6: R = H; n = 0
b $\{$ 8: R = pMBn; n = 2
c $\{$ 9: R = H; n = 2
    10: R = pMBn; n = 4
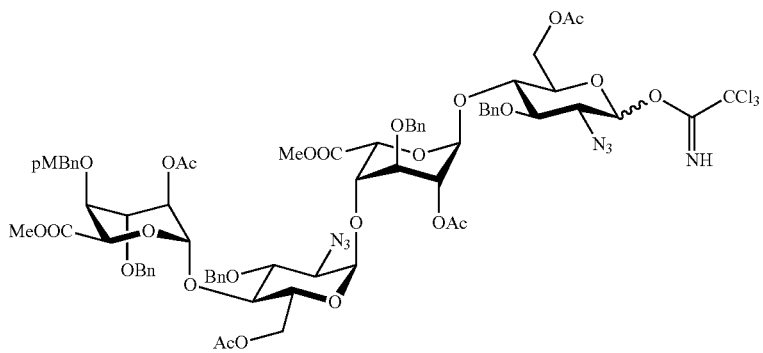
7
a) TMSOTf, 4 Å, CH$_2$Cl$_2$, -40 to -10° C., 80%. b) TFA, CH$_2$Cl$_2$, RT, 93% 6, 91% 9. c) 7 (1.3 eq.), TBDMSOTf, 4 Å, CH$_2$Cl$_2$, -40 to -10° C., 78% 8 along with 10% unreacted 6, 85% 10 along with 6% unreacted 9.

Scheme 3: Preparation of sulfated oligosaccharide 15, 18 and 19.
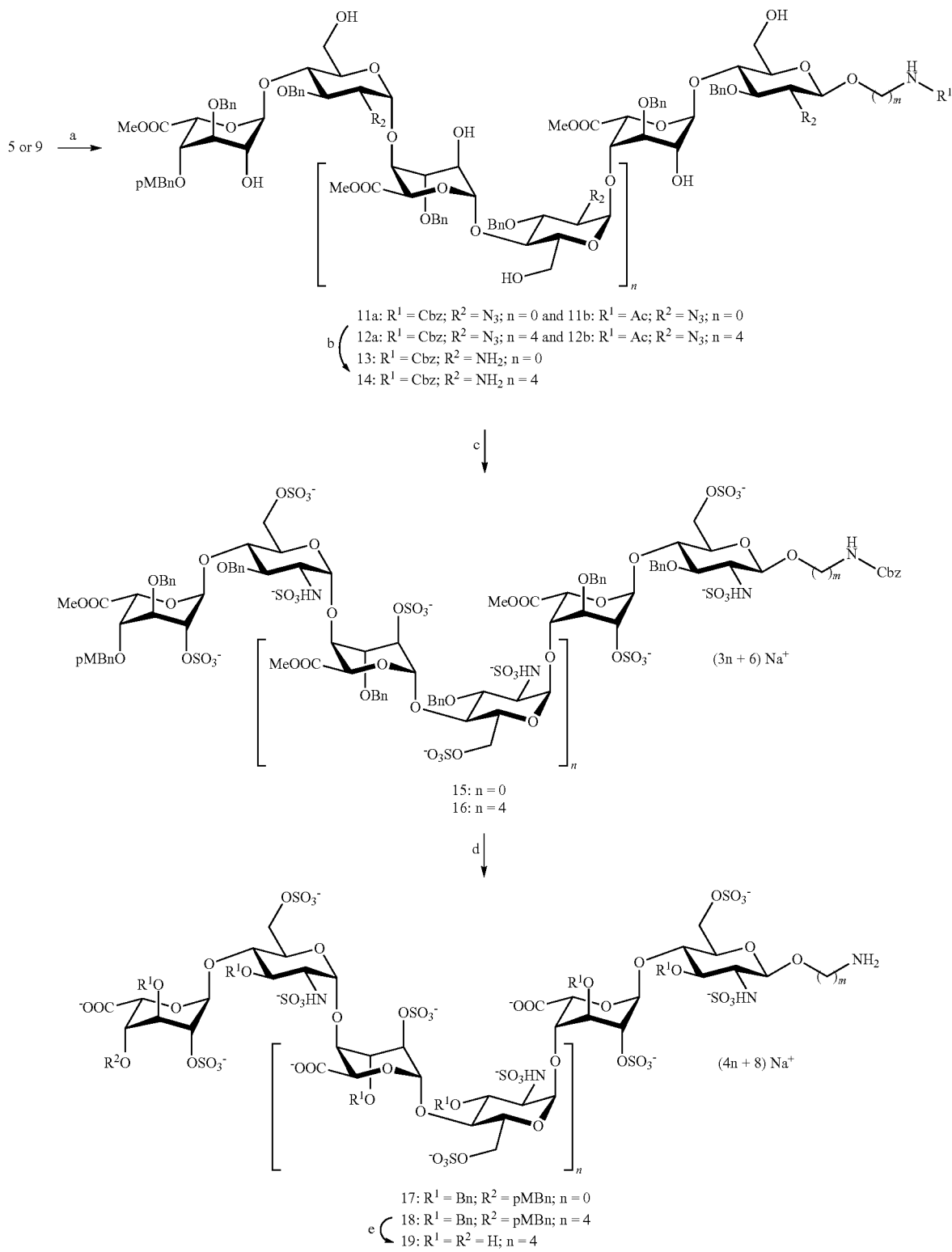
a) K$_2$CO$_3$, MeOH/CH$_2$Cl$_2$ (10/4), 0° C., 71% 11a along with 13% 11b, 80% 12a along with 17% 12b. b) 1,3-propanedithiol, NEt$_3$, MeOH, 75% (12), 86% (13). c) pyridine•SO$_3$, pyridine 16 h RT, 20 h 55° C., 51% (15), 52% (16). d) LiOH, H$_2$O$_2$, 24 h RT, 50% (17); KOH, H$_2$O$_2$, 48 h 37° C., 51% (18). e) Pd(OH)$_2$, aq. phosphate buffer 0, 1M pH 7.0/tBuOH (6/2), quant. (19).

V.2. Chemical Synthesis of the Organic Molecules (Polysaccharides)

Compound 1, 2 and 7 are synthesized according to Lubineau et al. (*Chem. Eur. J.* 2004, 10, 4265-4282) and WO 2004/000887.

Compound 3: 5-(Acetamido-N-benzyloxycarbonyl)pentyl(methyl 2-O-acetyl-3-O-benzyl-4-O-(4-methoxybenzyl)-α-L-idopyranosyluronate)-(1→4)-O-6-O-acetyl-2-azido-3-O-benzyl-2-deoxy-α-D-glucopyranoside

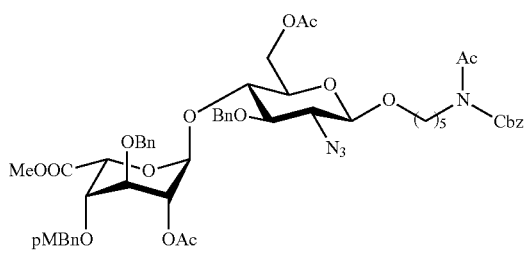

Acceptor 2 (50 mg, 0.18 mmol, 2 eq) and imidate 1 (83 mg, 0.09 mmol) were azeotropically dried with toluene and dissolved in dry $CH_2Cl_2$ (400 μL). Powdered 4 Å molecular sieves (300 mg) was added and the mixture was stirred for 30 min at rt under argon. The solution was cooled to −40° C. and TMSOTf (0.2 M in $CH_2Cl_2$, 90 μL, 0.018 mmol, 0.2 eq) was added. The reaction was stirred at this temperature for 15 min and then raised to −10° C. over 30 min. The reaction was then quenched with a solution of $NEt_3$ (0.2 M in $CH_2Cl_2$, 180 μL, 0.036 mmol, 0.4 eq). The solution was filtered and then purified by silica gel flash chromatography (toluene/AcOEt 6:1 to 1:1) giving separately α and β anomers of the disaccharide 3 (76 mg, 79%) in a ratio of α/β≈2/8.

$^1$H NMR (300 MHz, $CDCl_3$) δ=7.43-7.23 (m, 15H, Ph), 7.13 (d, J=8.5 Hz, 2H, Ph-OMe), 6.83 (d, J=8.5 Hz, 2H, Ph-OMe), 5.25 (d, $J_{1,2}$=4.5 Hz, 1H, H-1$^B$), 5.23 (s, 2H, C$\underline{H}_2$Ph(Cbz)), 4.87 (t, $J_{1,2}$=$J_{2,3}$=4.5 Hz, 1H, H-2$^B$), 4.82 (d, J=11.0 Hz, 1H, C$\underline{H}_2$Ph), 4.73 (d, $J_{6,4}$=4.0 Hz, 1H, H-5$^B$), 4.71 (d, J=11.0 Hz, 1H, C$\underline{H}_2$Ph), 4.70 (d, J=11.5 Hz, 1H, C$\underline{H}_2$Ph), 4.64 (d, J=11.5 Hz, 1H, C$\underline{H}_2$Ph), 4.46 (d, J=11.5 Hz, 1H, C$\underline{H}_2$Ph), 4.42 (dd, $J_{6a,6b}$=11.5 Hz, $J_{6a,5}$=2.0 Hz, 1.5H, H-6$_a^A$), 4.40 (d, J=11.5 Hz, 1H, C$\underline{H}_2$Ph), 4.21 (d, $J_{1,2}$=7.5 Hz, 1H, H-1$^A$), 4.18 (dd, $J_{6a,6b}$=11.5 Hz, $J_{6b,5}$=4.0 Hz, 1H, H-6$_b^A$), 3.93 (t, $J_{4,5}$=$J_{4,3}$=9.5 Hz, 1H, H-4$^A$), 3.85 (dt, $J_{a,a'}$=9.5 Hz, $J_{a,b}$=6.5 Hz, 1H, H-a), 3.81 (t, $J_{3,4}$=$J_{4,5}$=4.0 Hz, 1H, H-4$^B$), 3.80 (s, 1H, PhOMe), 3.76 (dd, $J_{2,3}$=4.5 Hz, $J_{3,4}$=4.0 Hz, 1H, H-3$^B$), 3.80-3.74 (m, 2H, H-e), 3.55 (s, 3H, COOMe), 3.52-3.38 (m, 2H, H-a' and H-5$^A$), 3.35 (dd, $J_{2,3}$=10.0 Hz, $J_{2,1}$=7.5 Hz, 1H, H-2$^A$), 3.31 (t, $J_{3,2}$=$J_{3,4}$=9.5 Hz, 1H, H-3$^A$), 2.50 (s, 3H, C$\underline{H}_3$ NAc), 2.06 (s, 3H, C$\underline{H}_3$ OAc), 2.03 (s, 3H, C$\underline{H}_3$ OAc), 1.68-1.48 (m, 4H, H-b and H-d), 1.43-1.28 (m, 2H, H-c);

$^{13}$C NMR (100.6 MHz, $CDCl_3$) δ=172.8, 170.7, 170.0, 169.8 (C=O), 159.4 (C—OMe, pMBn), 138.1, 137.9, 135.1, 135.0 (C$_{quaternary\ arom}$), 129.6, 129.4, 129.0, 128.9, 128.7, 128.6, 128.4, 128.3, 128.2, 128.1, 127.9, 127.8, 127.4 (C$_{arom}$), 113.7 (C$_m$ pMBn), 102.1 (C-1$^A$), 97.9 (C-1$^B$), 80.9 (C-3$^A$), 75.3 (C-4$^A$), 74.9 (C$\underline{H}_2$Ph), 74.8 (C-4$^B$), 74.4 (C-3$^B$), 73.1 (C-5$^A$), 73.0 (C$\underline{H}_2$Ph), 72.4 (C$\underline{H}_2$Ph), 70.5 (C-5$^B$), 70.1 (C-2$^B$), 70.0 (C$\underline{H}_2$-a), 68.4 (C$\underline{H}_2$Ph Cbz), 66.2 (C-2$^A$), 62.2 (C-6$^A$), 55.2 (C$\underline{H}_3$, COOMe), 51.8 (C$\underline{H}_3$, COOMe), 44.0 (C$\underline{H}_2$-e), 29.0 (C$\underline{H}_2$-b), 28.2 (C$\underline{H}_2$-d), 26.8 (C$\underline{H}_3$, NAc), 23.1 (C$\underline{H}_2$-c), 20.9, 20.8 (C$\underline{H}_3$, OAc);

ESI HR-MS m/z calculated for $C_{54}H_{64}N_4O_{17}Na$ [M+Na]$^+$: 1063.4159, found: 1063.4171.

Compound 4: 5-(Acetamido-N-benzyloxycarbonyl)pentyl(methyl 2-O-acetyl-3-O-benzyl-α-L-idopyranosyluronate)-(1→4)-O-6-O-acetyl-2-azido-3-O-benzyl-2-deoxy-α-D-glucopyranoside

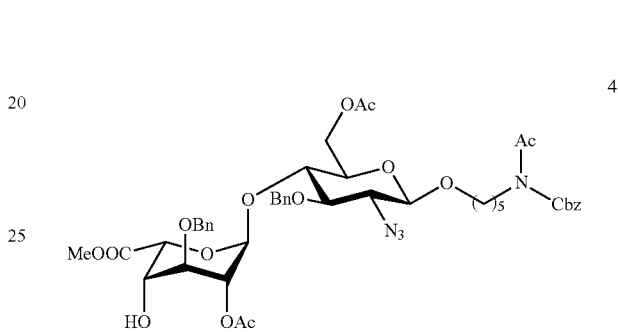

TFA (160 μL, 2.16 mmol, 18 eq) was added slowly to a solution of disaccharide 3 (125 mg, 0.12 mmol) in dry $CH_2Cl_2$ (1.6 mL) and the resulting purple solution was stirred under argon during 1 hour. $NEt_3$ (350 μL) was then added and the resulting solution was concentrated. Flash chromatography of the residue (silica gel, petroleum ether/AcOEt 85:15 to 35:65) gave the desired disaccharide 4 (103 mg, 93%).

$^1$H NMR (360 MHz, $CDCl_3$) δ=7.45-7.22 (m, 15H, Ph), 5.20 (s, 2H, C$\underline{H}_2$Ph(Cbz)), 5.03 (br.s, 1H, H-1$^B$), 4.92 (d, $J_{5,4}$=1.5 Hz, 1H, H-5$^B$), 4.88 (br.s, 1H, H-2$^B$), 4.72 (d, J=11.5 Hz, 1H, C$\underline{H}_2$Ph), 4.71 (d, J=11.5 Hz, 1H, C$\underline{H}_2$Ph), 4.66 (d, J=11.5 Hz, 1H, C$\underline{H}_2$Ph), 4.60 (d, J=11.5 Hz, 1H, C$\underline{H}_2$Ph), 4.42 (d, $J_{6a,6b}$=12.0 Hz, $J_{6a,5}$=2.0 Hz, 1H, H-6$_a^A$), 4.20 (d, $J_{1,2}$=8.0 Hz, 1H, H-1$^A$), 4.15 (d, $J_{6a,6b}$=12.0 Hz, $J_{6b,5}$=4.0 Hz, 1H, H-6$_b^A$), 3.95 (br. d, $J_{4,OH}$=10.5 Hz, 1H, H-4$^B$), 3.90-3.84 (m, 1H, H-a), 3.82 (t, $J_{4,5}$=$J_{4,3}$=10.0 Hz, 1H, H-4$^A$), 3.74-3.66 (m, 3H, H-3$^B$ and H-e), 3.49-3.32 (m, 5H, containing s at δ=3.47, PhOMe, H-a' and H-5$^A$), 3.36 (dd, $J_{2,3}$=10.0 Hz, $J_{2,1}$=8.0 Hz, 1H, H-2$^A$), 3.23 (t, $J_{3,2}$=$J_{3,4}$=10.0 Hz, 1H, H-3$^A$), 2.59 (d, $J_{OH,4}$=10.5 Hz, 1H, OH), 2.46 (s, 3H, C$\underline{H}_3$ NAc), 2.05 (s, 3H, C$\underline{H}_3$ OAc), 2.04 (s, 3H, C$\underline{H}_3$ OAc), 1.65-1.53 (m, 2H, H-b), 1.51 (q, $J_{c,d'}$=$J_{c,d}$=$J_{e,d}$=7.5 Hz, 2H, H-d), 1.41-1.30 (m, 2H, H-c);

$^{13}$C NMR (100.6 MHz, $CDCl_3$) δ=172.8, 170.5, 169.4, 169.1 (C=O), 137.9, 137.2, 135.1 (C$_{quaternary\ arom}$), 128.6, 128.4, 128.2, 128.1, 127.9, 127.4 (C$_{arom}$), 102.2 (C-1$^A$), 98.0 (C-1$^B$), 81.0 (C-3$^A$), 74.8 (C-4$^A$), 74.6 (C$\underline{H}_2$Ph), 74.4 (C-3$^B$), 73.1 (C-5$^A$), 72.3 (C$\underline{H}_2$Ph), 69.9 (C$\underline{H}_2$-a), 68.5 (C-5$^B$), 68.4 (C$\underline{H}_2$Ph Cbz), 67.7 (C-4$^B$), 67.2 (C-2$^B$), 66.4 (C-2$^A$), 62.2 (C-6$^A$), 52.0 (C$\underline{H}_3$, COOMe), 43.9 (C$\underline{H}_2$-e), 29.0 (C$\underline{H}_2$-b), 28.2 (C$\underline{H}_2$-d), 26.8 (C$\underline{H}_3$, NAc), 23.1 (C$\underline{H}_2$-c), 20.9, 20.8 (C$\underline{H}_3$, OAc);

ESI HR-MS m/z calcd for $C_{46}H_{56}N_4O_{16}Na$ [M+Na]$^+$: 943.35890, found: 943.36018.

Compound 5: 5-(Acetamido-N-benzyloxycarbonyl)pentyl[(methyl 2-O-acetyl-3-O-benzyl-4-O-(4-methoxybenzyl)-α-L-idopyranosyluronate)-(1→4)-O-(6-O-acetyl-2-azido-3-O-benzyl-2-deoxy-α-D-glucopyranoside)-(1→4)-O-(methyl 2-O-acetyl-3-O-benzyl-α-L-idopyranosyluronate)]-(1→4)-O-6-O-acetyl-2-azido-3-O-benzyl-2-deoxy-α-D-glucopyranoside

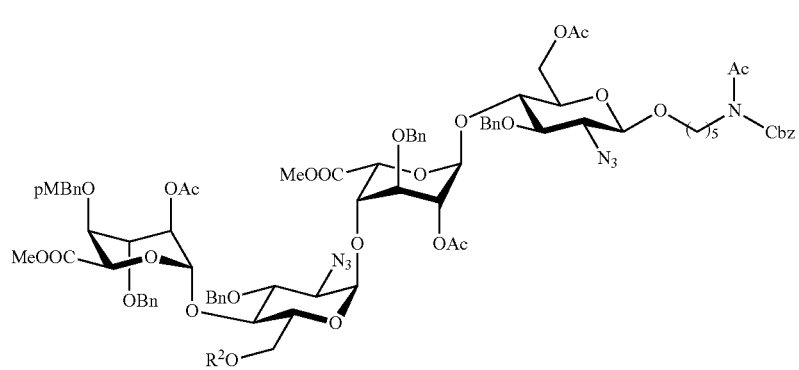

Acceptor 4 (80 mg, 0.087 mmol) and imidate 1 (107 mg, 0.12 mmol, 1.3 eq) were azeotropically dried with toluene and dissolved in dry $CH_2Cl_2$ (360 µL). Powdered 4 Å molecular sieves (280 mg) was added and the mixture was stirred for 30 min at rt under argon. The solution was cooled to −40° C. and TMSOTf (0.2 M in $CH_2Cl_2$, 89 µL, 0.017 mmol, 0.2 eq) was added. The reaction was stirred at this temperature for 15 min and then raised to −10° C. over 30 min. The reaction was then quenched with a solution of $NEt_3$ (0.2 M in $CH_2Cl_2$, 180 µL, 0.035 mmol, 0.4 eq). The solution was filtered and applied to the top of a Sephadex LH-20 chromatography ($CH_2Cl_2$/MeOH, 1:1). The fractions containing tetrasaccharide 5 were pooled, concentrated and purified by silica gel flash chromatography (toluene/AcOEt 85:15 to 35:65) giving tetrasaccharide 5 (116 mg, 80%).

$^1$H NMR (360 MHz, $CDCl_3$) δ=7.37-7.14 (m, 25H, Ph), 7.06 (d, J=8.5 Hz, 2H, P$\underline{h}$-OMe), 6.76 (d, J=8.5 Hz, 2H, P$\underline{h}$-OMe), 5.20 (d, $J_{1,2}$=5.5 Hz, 1H, H-1$^B$), 5.16 (s, 2H, C$\underline{H}_2$Ph(Cbz)), 5.14 (d, $J_{1,2}$=3.5 Hz, 1H, H-1$^D$), 4.83 (d, J=10.0 Hz, 1H, C$\underline{H}_2$Ph), 4.86-4.79 (m, 2H, H-2$^D$ and H-1$^C$), 4.79 (t, $J_{2,3}$=$J_{2,1}$=5.5 Hz, 1H, H-2$^B$), 4.69 (d, J=10.5 Hz, 1H, C$\underline{H}_2$Ph), 4.71-4.62 (m, 4H, H-5$^D$, 2C$\underline{H}_2$Ph), 4.59 (s, 2H, C$\underline{H}_2$Ph), 4.55 (d, J=10.5 Hz, 1H, C$\underline{H}_2$Ph), 4.52 (d, $J_{5,4}$=5.0 Hz, 1H, H-5$^B$), 4.39 (d, J=11.5 Hz, 1H, C$\underline{H}_2$PhOMe), 4.38-4.34 (m, 1H, H-6$_a^A$), 4.35 (d, J=11.5 Hz, 1H, C$\underline{H}_2$PhOMe), 4.28 (d, $J_{6a,6b}$=12.0 Hz, 1H, H-6$_a^C$), 4.14 (d, $J_{1,2}$=7.5 Hz, 1H, H-1$^A$), 4.14-4.10 (m, 1H, H-6$_b^A$), 4.08 (dd, $J_{6b,6a}$=12.0, $J_{6b,5}$=2.5 Hz, 1H, H-6$_b^C$), 3.92 (t, $J_{4,3}$=$J_{4,5}$=4.0 Hz, 1H, H-4$^D$), 3.88 (t, $J_{4,5}$=$J_{4,3}$=9.0 Hz, 1H, H-4$^C$), 3.83 (t, $J_{3,4}$=$J_{3,2}$=4.0 Hz, 1H, H-3$^D$), 3.78 (t, $J_{4,5}$=$J_{4,3}$=10.0 Hz, 1H, H-4$^A$), 3.81-3.62 (m, 9H, containing s at δ=3.73, H-a, H-5$^C$, H-4$^B$, PhO$\underline{Me}$, H-3$^B$ and H-e), 3.58 (dd, $J_{3,2}$=10.0, $J_{3,4}$=9.0 Hz, 1H, H-3$^C$), 3.49 (s, 3H, COO$\underline{Me}$), 3.42 (s, 3H, COO$\underline{Me}$), 3.42-3.31 (m, 2H, H-5$^A$ and H-a'), 3.29 (dd, $J_{2,3}$=9.5, $J_{2,1}$=7.5 Hz, 1H, H-2$^A$), 3.22 (dd, $J_{2,3}$=10.0, $J_{2,1}$=3.5 Hz, 1H, H-2$^C$), 3.21 (dd, $J_{3,4}$=10.0, $J_{3,2}$=9.5 Hz, 1H, H-3$^A$), 2.42 (s, 3H, C$\underline{H}_3$ NAc), 2.03 (s, 3H, C$\underline{H}_3$ OAc), 1.98 (s, 3H, C$\underline{H}_3$ OAc), 1.96 (s, 3H, C$\underline{H}_3$ OAc), 1.95 (s, 3H, C$\underline{H}_3$ OAc), 1.61-1.48 (m, 2H, H-b), 1.47 (q, $J_{c,d}$=$J_{c,d'}$=$J_{e,d}$=7.5 Hz, 2H, H-d), 1.28 (m, 2H, H-c).

$^{13}$C NMR (100.6 MHz, $CDCl_3$) δ=159.5 ($\underline{C}$—OMe, pMBn), 138.0, 137.8, 137.2 ($C_{quaternary\ arom}$), 129.6, 128.7, 128.6, 128.5, 128.4, 128.3, 128.2, 128.0, 127.9, 127.8, 127.5 ($C_{arom}$), 113.8 ($C_m$ pMBn), 102.2 (C-1$^A$), 98.0 (C-1$^D$), 97.9 (C-1$^B$), 97.4 (C-1$^C$), 81.0 (C-3$^A$), 77.9 (C-3$^C$), 75.6 (C-4$^C$), 75.5 (C-3$^B$), 75.3 (C-4$^B$ and C-4$^A$), 75.0 ($\underline{CH}_2$Ph), 74.8 ($\underline{CH}_2$Ph), 73.7 (C-3$^D$), 73.5 ($\underline{CH}_2$Ph), 73.3 ($\underline{CH}_2$Ph), 73.1 (C-5$^A$), 72.9 (C-4$^D$), 72.6 ($\underline{CH}_2$ pMBn), 71.2 (C-5$^B$), 71.0 (C-2$^B$), 70.0 ($\underline{CH}_2$-a), 69.7 (C-5$^C$), 69.3 (C-5$^D$), 68.8 (C-2$^D$), 68.4 ($\underline{CH}_2$Ph Cbz), 66.2 (C-2$^A$), 62.8 (C-2$^C$), 62.2 (C-6$^A$), 61.7 (C-6$^C$), 55.3 ($\underline{CH}_3$, OMe pMBn), 52.0 ($\underline{CH}_3$, COOMe), 51.7 ($\underline{CH}_3$, COOMe), 44.1 ($\underline{CH}_2$-e), 29.1 ($\underline{CH}_2$-b), 28.3 ($\underline{CH}_2$-d), 26.8 ($\underline{CH}_3$, NAc), 23.1 ($\underline{CH}_2$-c), 20.9, 20.7 ($\underline{CH}_3$, OAc);

IR (thin film): ν=3021 ($ν_{C—H\ arom}$), 2948, 2933, 2833 ($ν_{C—H\ aliph}$), 2110 ($ν_{N3}$), 1741 ($ν_{C=O}$), 1618, 1550, 1509, 1452, 1369, 1227;

$[α]_D^{28}$=−8.0833 (c=1.2, in $CH_2Cl_2$);

ESI HR-MS m/z calculated for $C_{85}H_{99}N_7O_{29}Na$ [M+Na]$^+$: 1704.63849, found: 1704.63252.

Compound 8: 5-(Acetamido-N-benzyloxycarbonyl) pentyl[(methyl 2-O-acetyl-3-O-benzyl-4-O-(4-methoxybenzyl)-α-L-idopyranosyluronate)-(1→4)-O-(6-O-acetyl-2-azido-3-O-benzyl-2-deoxy-α-D-glucopyranoside)-(1→4)-O-(methyl 2-O-acetyl-3-O-benzyl-α-L-idopyranosyluronate)-(1→4)-O-(6-O-acetyl-2-azido-3-O-benzyl-2-deoxy-α-D-glucopyranoside)-(1→4)-O-(methyl 2-O-acetyl-3-O-benzyl-α-L-idopyranosyluronate)]-(1→4)-O-6-O-acetyl-2-azido-3-O-benzyl-2-deoxy-α-D-glucopyranoside

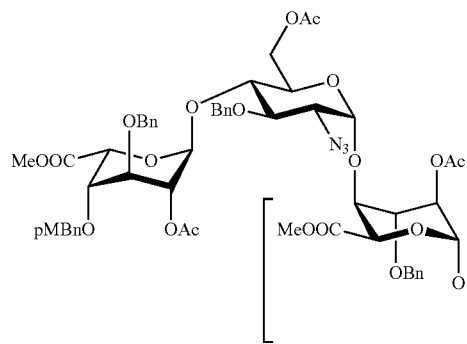
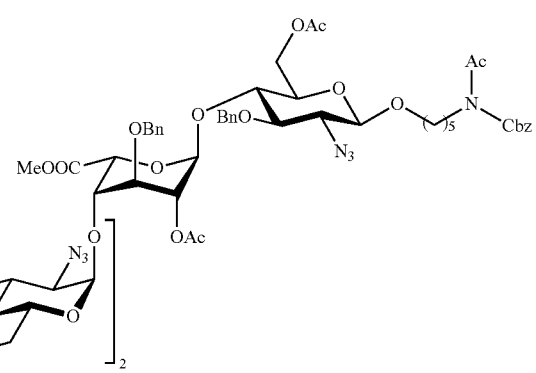

Tetrasaccharide 5 (110 mg, 0.065 mmol) was treated with TFA (87 μL, 1.18 mmol) in CH$_2$Cl$_2$ (850 μL), as described above for disaccharide 3, giving 95 mg of tetrasaccharide 6 (93%). Acceptor 6 (95 mg, 0.061 mmol) and imidate 7 (123.5 mg, 0.079 mmol, 1.3 eq) were azeotropically dried with toluene and dissolved in dry CH$_2$Cl$_2$ (900 μL). Powdered 4 Å molecular sieves (325 mg) was added and the mixture was stirred for 30 min at rt under argon. The solution was cooled to −40° C. and TBDMSOTf (0.2 M in CH$_2$Cl$_2$, 60 μL, 0.012 mmol, 0.2 eq) was added. The reaction was stirred at this temperature for 15 min and then raised to −10° C. over 30 min. The reaction was then quenched with a solution of NEt$_3$ (0.2 M in CH$_2$Cl$_2$, 120 μL, 0.024 mmol, 0.4 eq) and stirred at this temperature during 15 min. The solution was then directly applied to the top of a Sephadex LH-20 chromatography (CH$_2$Cl$_2$/MeOH, 1:1) and purified by silica gel flash chromatography (toluene/AcOEt 85:15 to 35:65) giving octasaccharide 8 (141 mg, 78%) along with 10 mg unreacted acceptor 6 (10%).

$^1$H NMR (400 MHz, CDCl$_3$) δ=7.45-7.10 (m, 47H, Ph), 6.75 (d, J=8.5 Hz, 2H, P$\underline{h}$-OMe), 5.22 (d, J$_{1,2}$=5.5 Hz, 1H, H-1$^B$), 5.21 (d, J$_{1,2}$=5.5 Hz, 2H, H-1$^D$ and H-1$^F$), 5.14 (s, 2H, C$\underline{H}_2$Ph(Cbz)), 5.13 (d, J$_{1,2}$=3.5 Hz, 1H, H-1$^H$), 4.89 (d, J$_{1,2}$=3.0 Hz, 2H, H-1$^C$ or H-1$^E$ or H-1$^G$ and H-1$^E$ or H-1$^G$ or H-1$^C$), 4.86-4.77 (m, 6H, H-1$^G$ or H-1$^C$ or H-1$^E$, H-2$^B$, H-2$^D$, H-2$^F$, H-2$^E$ and C$\underline{H}_2$Ph), 4.78 (d, J=11.0 Hz, 2H, C$\underline{H}_2$Ph), 4.72-4.53 (m, 14H, containing at δ=4.79 H-5$^H$, 13×C$\underline{H}_2$Ph), 4.50 (d, J=5.0 Hz, 2H, H-5$^D$ and H-5$^F$), 4.48 (d, J=5.0 Hz, 1H, H-5$^B$), 4.38 (d, J=11.0 Hz, 1H, C$\underline{H}_2$PhOMe), 4.35 (d, J=11.0 Hz, 1H, C$\underline{H}_2$PhOMe), 4.39-4.26 (m, 3H, H-6$_a{}^A$, H-6$_a{}^C$ and H-6$_a{}^E$), 4.26 (d, J$_{6a,6b}$=11.0 Hz, 1H, H-6$_a{}^G$), 4.13 (d, J$_{1,2}$=8.0 Hz, 1H, H-1$^A$), 4.15-4.03 (m, 4H, H-6$_b{}^A$, H-6$_b{}^C$, H-6$_b{}^E$ and H-6$_b{}^G$), 3.96-3.88 (m, 3H, H-4$^H$, H-4$^F$ and H-4$^D$), 3.90-3.68 (m, 16H, containing s at δ=3.71, H-4$^G$, H-3$^D$, H-3$^F$, H-3$^E$, H-4$^E$, H-4$^C$, H-4$^A$, H-a, H-5$^G$, H-5$^C$, H-5$^E$, H-4$^B$, PhOMe and H-3$^B$), 3.65 (br t, J$_{d,e}$=7.5 Hz, 2H, H-e), 3.61-3.50 (m, 3H, H-3$^G$, H-3$^E$ and H-3$^C$), 3.50 (s, 3H, COOMe), 3.47 (s, 3H, COOMe), 3.45 (s, 3H, COOMe), 3.41 (s, 3H, COOMe), 3.41-3.31 (m, 2H, H-a' and H-5$^A$), 3.28 (dd, J$_{2,3}$=9.5, J$_{2,1}$=8.0 Hz, 1H, H-2$^A$), 3.24-3.15 (m, 4H, containing t at δ=3.20 H-3$^A$, H-2$^C$, H-2$^E$ and H-2$^G$), 2.40 (s, 3H, C$\underline{H}_3$ NAc), 2.01 (s, 6H, C$\underline{H}_3$ OAc), 2.00 (s, 3H, C$\underline{H}_3$ OAc), 1.96 (s, 3H, C$\underline{H}_3$ OAc), 1.94 (2 s, 6H, C$\underline{H}_3$ OAc), 1.93 (s, 6H, C$\underline{H}_3$ OAc), 1.57-1.46 (m, 2H, H-b), 1.46 (q, J$_{c,d}$=J$_{e,d}$=7.5 Hz, 2H, H-d), 1.33-1.22 (m, 2H, H-c);

$^{13}$C NMR (100.6 MHz, CDCl$_3$) δ=170.7, 170.6, 169.9, 169.7, 169.5, 169.3 (C=O), 159.5 ($\underline{C}$—OMe, pMBn), 137.9, 137.8, 137.7, 137.6, 137.4, 137.3 (C$_{quaternary\ arom}$), 129.6, 129.3, 128.6, 128.5, 128.4, 128.2, 127.8, 127.6 (C$_{arom}$), 113.8 (C$_m$ pMBn), 102.1 (C-1$^A$), 98.0 (C-1$^H$), 97.9 (C-1$^B$, C-1$^D$ and C-1$^F$), 97.7 (C-1$^{C\ or\ E\ or\ G}$ and C-1$^{E\ or\ G\ or\ C}$) 97.1 (C-1$^{G\ or\ C\ or\ E}$), 80.9 (C-3$^A$), 77.9, 77.8, 77.7 (C-3$^C$, C-3$^E$ and C-3$^G$), 75.7 (C-3$^B$ and C-4$^G$), 75.6 (C-4$^A$ and C-4$^B$), 75.5 (C-4$^{C\ or\ E}$), 75.4 (C-3$^{D\ or\ F}$ and C-4$^{C\ or\ E}$), 75.2 (C-3$^{D\ or\ F}$), 75.0 (2× $\underline{C}$H$_2$Ph), 74.8 (4× $\underline{C}$H$_2$Ph), 74.1 ($\underline{C}$H$_2$Ph), 74.0 ($\underline{C}$H$_2$Ph), 73.6 (C-3$^E$ and $\underline{C}$H$_2$Ph), 73.5, 73.4 (C-4$^D$ and C-4$^F$), 73.2 ($\underline{C}$H$_2$Ph), 73.1 (C-5$^A$), 72.6 ($\underline{C}$H$_2$ pMBn and C-4$^H$), 71.3 (C-5$^D$ or C-5$^F$), 71.2 (C-2$^D$ or C-2$^F$), 70.6 (C-5$^B$), 70.4 (C-2$^B$ or C-5$^F$), 70.3 (C-5$^D$ or C-2$^B$), 70.1 (C-2$^F$ or C-2$^D$), 70.0 ($\underline{C}$H$_2$-a), 69.7-60.6 (C-5$^C$, C-5$^F$ and C-5$^G$), 69.1 (C-5$^H$), 68.7 (C-2$^H$), 68.4 ($\underline{C}$H$_2$Ph Cbz), 66.2 (C-2$^A$), 63.0 (C-2$^{C\ or\ E}$), 62.8 (C-2$^{C\ or\ E}$ and C-2$^G$), 62.2 (C-6$^A$), 61.6 (C-6$^C$, C-6$^E$ and C-6$^G$), 55.2 ($\underline{C}$H$_3$, OMe pMBn), 52.0 (3× $\underline{C}$H$_3$, COOMe), 51.7 ($\underline{C}$H$_3$, COOMe), 44.0 ($\underline{C}$H$_2$-e), 29.0 ($\underline{C}$H$_2$-b), 28.3 ($\underline{C}$H$_2$-d), 26.8 ($\underline{C}$H$_3$, NAc), 23.1 ($\underline{C}$H$_2$-c), 20.8, 20.7 ($\underline{C}$H$_3$, OAc);

ESI HR-MS m/z calculated for C$_{147}$H$_{169}$N$_{13}$O$_{53}$Na [M+Na]$^+$: 2987.0821, found: 2987.0845.

Compound 10: 5-(Acetamido-N-benzyloxycarbonyl)pentyl[(methyl 2-O-acetyl-3-O-benzyl-4-O-(4-methoxybenzyl)-α-L-idopyranosyluronate)-(1→4)-O-(6-O-acetyl-2-azido-3-O-benzyl-2-deoxy-α-D-glucopyranoside)-(1→4)-O-(methyl 2-O-acetyl-3-O-benzyl-α-L-idopyranosyluronate)-(1→4)-O-(6-O-acetyl-2-azido-3-O-benzyl-2-deoxy-α-D-glucopyranoside)-(1→4)-O-(methyl 2-O-acetyl-3-O-benzyl-α-L-idopyranosyluronate)-(1→4)-O-(6-O-acetyl-2-azido-3-O-benzyl-2-deoxy-α-D-glucopyranoside)-(1→4)-O-(methyl 2-O-acetyl-3-O-benzyl-α-L-idopyranosyluronate)]-(1→4)-O-(6-O-acetyl-2-azido-3-O-benzyl-2-deoxy-α-D-glucopyranoside)-(1→4)-O-(methyl 2-O-acetyl-3-O-benzyl-α-L-idopyranosyluronate)]-(1→4)-O-6-O-acetyl-2-azido-3-O-benzyl-2-deoxy-α-D-glucopyranoside Octasaccharide 8 (136 mg, 0.046 mmol) was treated with TFA (61 μL, 0.825 mmol) in dry $CH_2Cl_2$ (1.2 mL), as described above for 3, giving 119 mg of compound 9 (91%). MALDI-TOF HR-MS m/z calculated for $C_{139}H_{161}N_{13}O_{52}Na$ [M+Na]$^+$: 2867.0246, found: 2867.0226). Acceptor 9 (95 mg, 0.034 mmol) and imidate 7 (65 mg, 0.042 mmol, 1.3 eq) were azeotropically dried with toluene and dissolved in dry $CH_2Cl_2$ (500 μL). Powdered 4 Å molecular sieves (180 mg) was added and the mixture was stirred for 30 min at rt under argon. The solution was cooled to −40° C. and TBDMSOTf (0.2 M in $CH_2Cl_2$, 33 μL, 0.0067 mmol, 0.2 eq) was added. The reaction was stirred at this temperature for 15 min and then raised to −10° C. over 30 min. The reaction was then quenched with a solution of $NEt_3$ (0.2 M in $CH_2Cl_2$, 66 μL, 0.013 mmol, 0.4 eq). The solution was filtered and then directly applied to the top of a Sephadex LH-20 chromatography ($CH_2Cl_2$/MeOH, 1:1). The fractions containing the dodecasaccharide were pooled, concentrated and purified by silica gel flash chromatography (toluene/AcOEt 80:20 to 50:50) giving dodecassaccharide 10 (120 mg, 85%) along with 6 mg unreacted acceptor 9 (6%).

$^1$H NMR (400 MHz, CDCl$_3$) δ=7.36-7.03 (m, 67H, Ph), 6.76 (d, J=8.5 Hz, 2H, Ph-OMe), 5.28-5.18 (m, 5H, H-1$^B$, H-1$^D$, H-1$^F$, H-1$^H$ and H-1$^J$), 5.16 (s, 2H, CH$_2$Ph(Cbz)), 5.14 (d, J$_{1,2}$=3.5 Hz, 1H, H-1$^L$), 4.95-4.89 (m, 4H, 4 of H-1$^C$, H-1$^E$, H-1$^G$, H-1$^I$, H-1$^K$), 4.88-4.75 (m, 10H, 1 of H-1$^C$, H-1$^E$, H-1$^G$, H-1$^I$, H-1$^K$ and H-2$^B$, H-2$^D$, H-2$^F$, H-2$^H$, H-2$^J$, H-2$^L$ and 4×CH$_2$Ph), 4.71 (d, J=11.0 Hz, 2H, CH$_2$Ph), 4.71 (br.s, 1H, H-5$^L$), 4.71-4.58 (m, 19H, 19×CH$_2$Ph), 4.55-4.43 (m, 5H, H-5$^B$, H-5$^D$, H-5$^H$, H-5$^H$ and H-5$^J$), 4.41 (d, J=11.0 Hz, 1H, CH$_2$PhOMe), 4.37 (d, J=11.0 Hz, 2H, CH$_2$PhOMe and H-6$_a^A$), 4.35-4.24 (m, 5H, H-6$_a^C$, H-6$_a^E$, H-6$_a^I$, H-6$_a^K$), 4.14 (d, J$_{1,2}$=8.0 Hz, 1H, H-1$^A$), 4.17-4.15 (m, 6H, H-6$_b^A$, H-6$_b^C$, H-6$_b^E$, H-6$_b^G$, H-6$_b^I$ and H-6$_b^K$), 3.95-3.72 (m, 25H, containing s at δ=3.73, H-4$^A$, H-4$^F$, H-4$^H$, H-4$^J$, H-4$^L$, H-4$^K$, H-4$^D$, H-3$^D$, H-3$^F$, H-3$^H$, H-3$^J$, H-3$^L$, H-4$^C$, H-4$^E$, H-4$^G$, H-4$^I$, H-a, H-5$^C$, H-5$^E$, H-5$^G$, H-5$^I$, H-5$^K$ and PhOMe), 3.72 (br.s, 2H, H-3$^B$ and H-4$^B$), 3.66 (br t, J$_{d,e}$=7.5 Hz, 2H, H-e), 3.63-3.52 (m, 5H, H-3$^C$, H-3$^E$, H-3$^G$, H-3$^I$ and H-3$^K$), 3.51 (s, 3H, COOMe), 3.47 (s, 9H, 3×COOMe), 3.46 (s, 3H, COOMe), 3.41 (s, 3H, COOMe), 3.43-3.32 (m, 2H, H-a' and H-5$^A$), 3.30 (dd, J$_{2,3}$=9.5, J$_2$, J$_{2,1}$=8.0 Hz, 1H, H-2$^A$), 3.26-3.17 (m, 6H, H-3$^A$, H-2$^C$, H-2$^E$, H-2$^G$, H-2$^I$ and H-2$^K$), 2.42 (s, 3H, CH$_3$ NAc), 2.03 (s, 6H, CH$_3$ OAc), 2.03 (s, 9H, CH$_3$ OAc), 1.98 (s, 3H, CH$_3$ OAc), 1.96 (s, 6H, CH$_3$ OAc), 1.95 (s, 12H, CH$_3$ OAc), 1.59-1.48 (m, 2H, H-b), 1.47 (q, J$_{c,d}$=J$_{c,f}$=J$_{e,d}$=7.5 Hz, 2H, H-d), 1.34-1.22 (m, 2H, H-c).

$^{13}$C NMR (100.6 MHz, CDCl$_3$) δ=170.6, 170.0, 169.7, 169.5 (C=O), 137.9, 137.8, 137.6, 137.5, 137.4, 137.3 (C$_{quaternary\ arom}$), 129.6, 129.0, 128.7, 128.6, 128.5, 128.4, 128.3, 128.2, 128.1, 128.0, 127.8, 127.6 (C$_{arom}$), 113.4 (C$_m$ pMBn), 102.1 (C-1$^A$), 98.0 (C-1$^L$), 97.8 (C-1$^B$, C-1$^D$, C-1$^F$, C-1$^H$, C-1$^J$ and C-1$^{C\ or\ E\ or\ G\ or\ I\ or\ K}$, C-1$^{E\ or\ G\ or\ I\ or\ K\ or\ C}$, C-1$^{G\ or\ I\ or\ K\ or\ C\ or\ E}$ and C-1$^{I\ or\ K\ or\ C\ or\ E\ or\ G}$), 97.1 (C-1$^{K\ or\ C\ or\ E\ or\ G\ or\ I}$), 80.9 (C-3$^A$), 77.9, 77.8 (C-3$^C$, C-3$^E$, C-3$^G$, C-3$^I$ and C-3$^K$), 75.7, 75.6, 75.5, 75.3, 75.2 (C-3$^B$, C-4$^B$, C-4$^A$, C-4$^C$, C-4$^E$, C-4$^G$, C-4$^I$, C-3$^D$, C-3$^F$, C-3$^H$, C-3$^J$ and C-4$^K$), 74.9, 74.8 (6×CH$_2$Ph), 74.1 (3×CH$_2$Ph), 74.0 (CH$_2$Ph), 73.7 (CH$_2$Ph), 73.4 (C-3$^L$), 73.1 (C-4$^D$, C-4$^F$, C-4$^H$, C-4$^J$ and C-5$^A$), 72.7 (C-4$^L$), 72.6 (CH$_2$ pMBn), 71.3 (C-5$^J$), 71.2 (C-2$^B$), 70.6, 70.5, 70.4, 70.3, 70.1 (C-5$^B$, C-5$^D$, C-5$^F$, C-5$^H$, C-2$^D$, C-2$^F$, C-2$^H$ and C-2$^J$), 70.0 (CH$_2$-a), 69.7 (C-5$^C$, C-5$^E$, C-5$^G$, C-5$^I$ and C-5$^K$), 69.1 (C-5$^L$), 68.7 (C-2$^L$), 68.4 (CH$_2$Ph Cbz), 66.2 (C-2$^A$), 62.9, 62.8, 62.7 (C-2$^C$, C-2$^E$, C-2$^G$, C-2$^I$ and C-2$^K$), 62.2 (C-6$^A$), 61.6 (C-6$^C$, C-6$^E$, C-6$^G$, C-6$^I$ and C-6$^K$), 55.3 (CH$_3$, OMe pMBn), 52.0 (4× CH$_3$, COOMe), 51.8 (2× CH$_3$, COOMe), 44.0 (CH$_2$-e), 29.0 (CH$_2$-b), 28.3 (CH$_2$-d), 26.9 (CH$_3$, NAc), 23.1 (CH$_2$-c), 20.9, 20.8, 20.7 (12× CH$_3$, OAc);

ESI HR-MS m/z calculated for $C_{209}H_{239}N_{19}O_{77}Na$ [M+Na]$^+$: 4269.5262, found: 4269.5280.

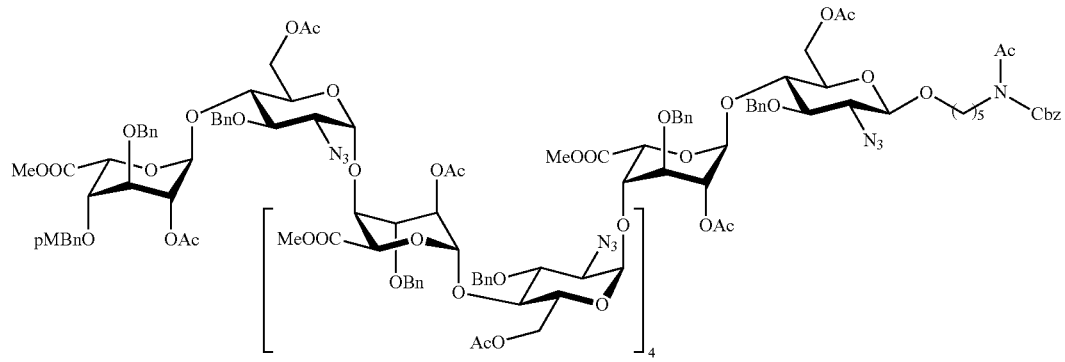

Compound 17: 5-aminopentyl[(3-O-benzyl-4-O-(4-methoxybenzyl)-2-O-sulfonato-α-L-idopyranosyluronate)-(1→4)-O-(3-O-benzyl-2-deoxy-2-sulfoamino-6-O-sulfonato-α-D-glucopyranoside)-(1→4)-O-(3-O-benzyl-2-O-sulfonato-α-L-idopyranosyluronate)]-(1→4)-O-3-O-benzyl-2-deoxy-2-sulfoamino-6-O-sulfonato-α-D-glucopyranoside heptasodium salt. (HS4Bz)

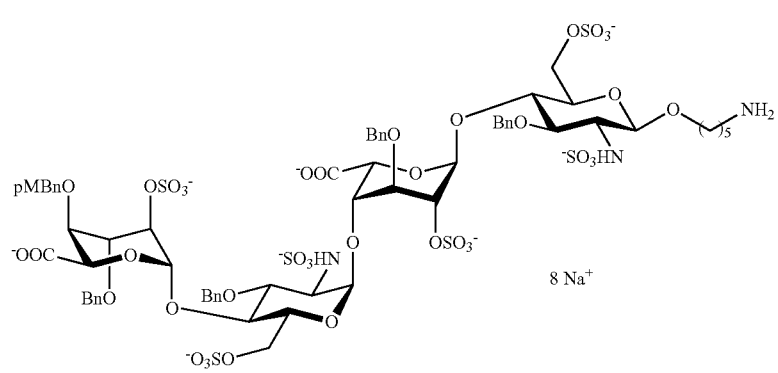

17

8 Na⁺

Tetrasaccharide 5 (29 mg, 0.017 mmol) was stirred at 0° C. for 2 h with $K_2CO_3$ (1.5 mg, 0.011 mmol, 0.625 eq) in a mixture of MeOH/$CH_2Cl_2$ (1 mL/0.4 mL) and then raised room temperature. The mixture was neutralised with BioRad AG 50W-X8 200 (H⁺) resin, filtered and concentrated. Silica gel flash chromatography (toluene/AcOEt 70:30 to 20:80) gave the deacetylated compound 11a (18 mg, 71%) along with 3 mg of compound 11b (13%, ESI HR-MS m/z calculated for $C_{75}H_{89}N_7O_{24}Na$ [M+Na]⁺: 1494.58567, found: 1494.58474).

Compound 11a (18 mg, 0.012 mmol) was then dissolved in MeOH (324 µL) and stirred with propane-1,3-dithiol (24 µL, 0.24 mmol, 20 eq) and triethylamine (33 µL, 0.24 mmol, 20 eq) for 15 hours. The resulting mixture was purified twice by Sephadex LH-20 chromatography ($CH_2Cl_2$/MeOH, 1:1 with 0.1% of $NEt_3$) giving 13 mg 13 (75%, ESI HR-MS m/z calculated for $C_{75}H_{93}N_3O_{24}Na$ [M+Na]⁺: 1442.60467, found: 1442.60248).

Sulfur trioxide pyridine complex (74 mg, 0.46 mmol, 60 eq) was added to a solution of 13 (11 mg, 7.75 µmol) in pyridine (320 µL). This mixture was protected from light, stirred for 24 h at rt and then heated for 20 h at 55° C. MeOH (140 µL, 0.124 mmol) and $NEt_3$ (63 µL, 0.014 mmol) were then added to quench the reaction. The resulting mixture was stirred for 1 h at rt and successively purified by Sephadex LH-20 chromatography ($CH_2Cl_2$/MeOH, 1:1) and RP-18 semi-preparative HPLC (AcOHNEt₃ 100 mM, pH 7.0/ $CH_3CN$ 70/30 to 58/42) followed by ion exchange on BioRad AG50W-X8 200 (Na⁺, 1 mL) after removal of AcOHNEt₃ salts by lyophilisation (2×1 mL $H_2O$). Compound 15 (8 mg, 51%, ESI MS of $C_{75}H_{87}N_3O_{42}S_6Na_6$: m/z (%) 654.1 (100) [M−3Na]³⁻/3, 992.8 (50) [M−2Na]²⁻/2) was thus obtained as an hexasodium salt.

Tetrasaccharide 15 (6 mg, 2.9 µmol) was dissolved in a mixture of LiOH (7 mg, 0.29 mmol, 52 eq), water (40 µL) and $H_2O_2$ (35% in water, 43 µL, 0.49 mmol). After 24 h at 37° C., AcOH (6 M, 36 µL, 0.22 mmol) was added and the mixture was purified by RP-18 semi-preparative HPLC (AcOHNEt₃ 100 mM, pH 7.0/$CH_3CN$ 75/25 to 60/40) followed by ion exchange on BioRad AG50W-X8 200 (Na⁺, 1 mL) after removal of AcOHNEt₃ salts by lyophilisation (2×1 mL $H_2O$). Compound 17 (3 mg, 50%) was thus obtained as an octasodium salt ¹H NMR (400 MHz, $D_2O$) δ=7.60-7.24 (m, 22H, Ph), 6.93 (d, J=8.5 Hz, 2H, Ph-OMe), 5.37 (br. s, 1H, H-1$^B$), 5.29 (br. s, 1H, H-1$^D$), 5.20 (d, $J_{1,2}$=3.0 Hz, 1H, H-1$^C$), 4.77 (d, J=12.0 Hz, 2H, CH₂Ph), 4.75 (d, $J_{1,2}$=6.5 Hz, 1H, H-1$^A$), 4.68 (br. s, 1H, H-5$^D$), 4.64 (d, J=12.0 Hz, 2H, CH₂Ph), 4.63 (d, $J_{4,5}$=2.0 Hz, 1H, H-5$^B$), 4.61 (d, J=12.0 Hz, 2H, CH₂Ph), 4.49 (d, J=12.0 Hz, 2H, CH₂Ph), 4.44 (d, J=11.0 Hz, 1H, CH₂PhOMe), 4.43 (br. s, 1H, H-2$^D$), 4.41 (br. s, 1H H-2$^B$), 4.40 (d, J=11.0 Hz, 1H, CH₂PhOMe), 4.36-4.24 (m, 4H, H-6$_a^A$, H-6$_a^A$, H-6$_a^C$ and H-6$_b^C$), 4.19 (br. s, 1H, H-3$^B$), 4.26 (br. s, 1H, H-4$^B$), 4.22-4.13 (m, 1H, H-5$^C$), 4.05 (t, $J_{4,5}$=$J_{4,3}$=6.5 Hz, 1H, H-4$^A$), 4.00 (m, 1H, H-5$^A$), 3.97-3.75 (m, 9H, containing s at δ=3.82, H-3$^D$, H-a, H-4$^C$, H-4$^D$, H-3$^A$, PhOMe and H-3$^C$), 3.79 (t, $J_{3,2}$=$J_{3,4}$=9.0 Hz, 1H, H-3$^C$), 3.64 (m, 1H, H-a'), 3.41 (dd, $J_{2,3}$=10.0, $J_{2,1}$=3.0 Hz, 1H, H-2$^C$), 3.34 (t, $J_{2,1}$=$J_{2,3}$=6.5 Hz, 1H, H-2$^A$), 2.95 (br. t, $J_{d,e}$=7.0 Hz, 2H, H-e), 1.67 (q, $J_{a,b}$=$J_{b,c}$=7.0 Hz, 2H, H-b), 1.65 (q, $J_{c,d}$=$J_{e,d}$=7.0 Hz, 2H, H-d), 1.47 (m, 2H, H-c);

¹³C NMR from ¹H-¹³C HSQC (100.6 MHz, $D_2O$) δ=101.7 (C-1$^A$), 98.5 (C-1$^C$), 97.8 (C-1$^B$), 97.6 (C-1$^D$), 79.4 (C-3$^A$), 77.5 (C-3$^C$), 75.5 (C-3$^B$), 75.2 (C-4$^B$), 74.2 (C-5$^A$), 73.9 (C-4$^C$), 73.7 (C-4$^D$), 74.6 (C-2$^B$), 73.5 (2× CH₂Ph), 73.0 (C-4$^A$), 72.4 (C-2$^D$), 72.1 (CH₂ pMBn, 2× CH₂Ph), 71.4 (C-3$^D$), 70.2 (CH₂-a), 69.8 (C-5$^C$), 69.2 (C-5$^B$), 69.1 (C-5$^D$), 68.5 (C-6$^A$), 67.3 (C-6$^C$), 58.8 (C-2$^C$), 58.6 (C-2$^A$), 55.9 (CH₃, OMe pMBn), 40.2 (CH₂-e), 28.9 (CH₂-b), 27.2 (CH₂-d), 23.1 (CH₂-c), LC-ESI-TOF-MS of $C_{65}H_{75}N_3O_{40}S_6Na_8$ (1913,1432): m/z (%) 1837.41 (100) [M−8Na+7H+$NEt_3$]⁻, 1736.29 (91) [M−8Na+7H]⁻, 1656.33 (86) [M−8Na+7H−$SO_3$]²⁻, 1576.36 (49) [M−8Na+7H−2$SO_3$]³⁻.

Compound 18: 5-aminopentyl[(3-O-benzyl-4-O-(4-methoxybenzyl)-2-O-sulfonato-α-L-idopyranosyluronate)-(1→4)-O-(3-O-benzyl-2-deoxy-2-sulfoamino-6-O-sulfonato-α-D-glucopyranoside)-(1→4)-O-(3-O-benzyl-2-O-sulfonato-α-L-idopyranosyluronate)-(3-O-benzyl-2-deoxy-2-sulfoamino-6-O-sulfonato-α-D-glucopyranoside)-(1→4)-O-(3-O-benzyl-2-O-sulfonato-α-L-idopyranosyluronate)-(3-O-benzyl-2-deoxy-2-sulfoamino-6-O-sulfonato-α-D-glucopyranoside)-(1→4)-O-(3-O-benzyl-2-O-sulfonato-α-L-idopyranosyluronate)-(3-O-benzyl-2-deoxy-2-sulfoamino-6-O-sulfonato-α-D-glucopyranoside)-(1→4)-O-(3-O-benzyl-2-O-sulfonato-α-L-idopyranosyluronate)-(3-O-benzyl-2-deoxy-2-sulfoamino-6-O-sulfonato-α-D-glucopyranoside)-(1→4)-O-(3-O-benzyl-2-O-sulfonato-α-L-idopyranosyluronate)]-(1→4)-O-3-O-benzyl-2-deoxy-2-sulfoamino-6-O-sulfonato-α-D-glucopyranoside tetracosasodium salt. (HS12Bz)

directly purified using RP-18 flash chromatography (AcOHNEt₃ 100 mM, pH 7.0/CH₃CN 100:0 to 60:40) and RP-C18 semi-prep HPLC (AcOHNEt₃ 100 mM, pH 7.0/CH₃CN) followed by ion exchange on BioRad AG50W-X8 200 (Na⁺, 3 mL) after removal of AcOHNEt₃ salts by lyophilisation (3×2 mL H₂O). Compound 16 (41 mg, 52%, LC-ESI-TOF-MS of $C_{183}H_{207}N_7O_{118}S_{18}Na_{18}$ (Exact mass=5379, 3543): m/z (%): 1830.09 (13) $[M-18Na+15H+5NEt_3]^{3-}/3$, 1768.73 (40) $[M-18Na+15H+4NEt_3-SO_3]^{3-}/3$, 1708.37 (73) $[M-18Na+15H+3NEt_3-2SO_3]^{3-}/3$, 1681.71 (93) $[M-18Na+15H+3NEt_3-3SO_3]^{3-}/3$, 1621.35 (100) $[M-18Na+15H+2NEt_3-4SO_3]^{3-}/3$) was thus obtained as an octadecasodium salt.

Dodecasasaccharide 16 (24 mg, 4.4 μmol) in aq. KOH (6 M, 480 μL, 3 mmol), water (192 μL) and H₂O₂ (35% in water, 768 μL, 9 mmol) was stirred for 24 h at 37° C. After this time, complete saponification of the methyl ester was observed but the Cbz group was only partially hydrolysed. Thus, aq. KOH (6M, 480 μL, 3 mmol) and H₂O₂ (35% in water, 768 μL, 9 mmol) were added and the reaction was stirred for additional 24 h at 37° C., time after which the hydrolysis of the Cbz

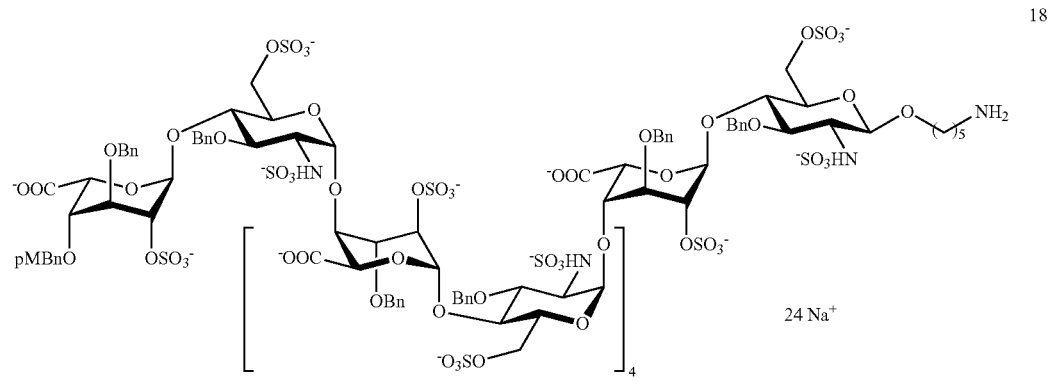

18

24 Na⁺

Dodecasasaccharide 11 (90 mg, 21 mol) was stirred at 0° C. for 2 h with K₂CO₃ (4.6 mg, 0.033 mmol) in a mixture of MeOH/CH₂Cl₂ (6 mL/3 mL) and then raised room temperature. The mixture was neutralised with BioRad AG 50W-X8 200 (H⁺) resin, filtered and concentrated. Silica gel flash chromatography (toluene/AcOEt 70:30 to 20:80) afforded the deacetylated compound 12a (63 mg, 80%) along with 13 mg of compound 12b (17%).

Dodecasasaccharide 12a (63 mg, 17 μmol) was then treated with propane-1,3-dithiol (210 μL, 2.1 mmol, 123 eq) and triethylamine (290 μL, 2.1 mmol, 123 eq) in MeOH (860 μL). This mixture stirred for 42 h at rt and then purified by Sephadex LH-20 chromatography (CH₂Cl₂/MeOH 0.1% NEt₃ 50:50) giving reduced dodecasaccharide 14 (52 mg, 86%).

Sulfur trioxide pyridine complex (208 mg, 1.31 mmol, 89 eq) was added to a solution of 14 (52 mg, 14 μmol) in pyridine (1.8 mL). This mixture was protected from light, stirred for 16 h at rt and then at 55° C. for 20 h. MeOH (800 μL, 20 mmol) and NEt₃ (360 μL, 2.6 mmol) were then added to quench the reaction. The resulting mixture was stirred for 1 h at rt and subsequently purified by Sephadex LH-20 chromatography (CH₂Cl₂/MeOH, 1:1). The dodecasaccharide containing fractions were pooled, concentrated. HPLC analyses showing that a small proportion of de-N-sulfated compounds had formed, re-N-sulfatation was performed in 2 ml water with sulfur trioxide pyridine complex (23 mg, 0.1 mmol) and K₂CO₃ (41 mg, 0.3 mmol) as base. The mixture was then group was complete. Aq. AcOH (6M, 720 μL, 4 mmol) was added and the mixture was purified using RP-C18 semi-preparative HPLC (AcOHNEt₃ 100 mM, pH 7.0/CH₃CN), followed by ion exchange on BioRad AG50W-X8 200 (Na⁺, 1 mL) after removal of AcOHNEt₃ salts by lyophilisation (3×2 mL H₂O). Compound 18 (12 mg, 51%) was thus obtained as a tetracosasodium salt.

$^1$H NMR (400 MHz, D₂O, 50° C., ref CH₃CN) only a part of the signals were attributed δ=7.55-7.25 (m, 62H, Ph), 7.93 (d, J=8.0 Hz, 2H, Ph-OMe), 6.94 (d, J=8.5 Hz, 2H, Ph-OMe), 5.60-5.32 (m of br. s, 6H, $H-1^B$, $H-1^D$, $H-1^F$, $H-1^H$, $H-1^J$ and $H-1^L$), 5.32-5.18 (m of br. s, 5H, $H-1^C$, $H-1^E$, $H-1^G$, $H-1^I$ and $H-1^K$), 4.90-4.81 (m, CH₂Ph), 4.81-4.71 (m, containing d at δ=4.77 (J=6.0 Hz, $H-1^A$) CH₂Ph and H-5$^{B\ or\ D\ or\ F\ or\ H\ or\ J\ or\ L}$), 4.71-4.65 (m, CH₂Ph and 5× H-5$^{B\ or\ D\ or\ F\ or\ H\ or\ J\ or\ L}$), 4.46-4.36 (m, 6H, $H-2^B$, $H-2^D$, $H-2^F$, $H-2^H$, $H-2^J$ and $H-2^L$), 4.35-4.27 (m, 6H, 6×H-6), 4.27-4.16 (m, 12H, $H-3^B$, $H-3^D$, $H-3^F$, $H-3^H$, $H-3^J$, $H-3^L$, $H-4^B$, $H-4^D$, $H-4^F$, $H-4^H$, $H-4^J$ and $H-4^L$), 3.87 (dt, $J_{gem}$=10.0 Hz, J=6.0 Hz, Ha), 3.82 (s, 3H, PhOMe), 3.61 (dt, $J_{gem}$=10.0 Hz, J=6.0 Hz, Ha'), 3.48-3.33 (m, 6H, $H-2^A$, $H-2^C$, $H-2^E$, $H-2^G$, $H-2^I$, $H-2^K$), 3.94 (t, J=7.5 Hz, 2H, H-e), 1.73-1.57 (m, 4H, H-d and H-b), 1.46 (q, J=7.5 Hz, 2H, H-c).

$^{13}$C NMR from $^1$H-$^{13}$C HSQC (100.6 MHz, D₂O, 50° C., ref CH₃CN) δ=114.8 ($C_m$ pMBn), 101.6 ($C-1^A$), 99.2-98.1 ($C-1^B$, $C-1^C$, $C-1^D$, $C-1^E$, $C-1^F$, $C-1^G$, $C-1^H$, $C-1^I$, $C-1^J$, $C-1^K$, $C-1^L$), 73.9 ($C-2^{Idurony\ moieties}$), 69.9 (C-a), 68.7 (C-6), 58.7

($C-2^C$, $C-2^E$, $C-2^G$, $C-2^I$, $C-2^K$), 55.2 ($\underline{C}H_3$ OMe pMBn), 40.2 (C-e), 28.5 (C-b), 26.9 (C-d), 23.0 (C-c).

ESI MS of $C_{169}H_{183}N_7O_{116}S_{18}Na_{24}$ (Exact mass=5293, 1153): m/z (%) 1756.03 (14) $[M-24Na+21H+5NEt_3]^{3-}/3$, 1722.32 (33) $[M-24Na+21H+4NEt_3]^{3-}/3$, 1695.67 (51) $[M-24Na+21H+3NEt_3-SO_3]^{3-}/3$, 1635.3 (100) $[M-24Na+21H+3NEt_3-2SO_3]^{3-}/3$.

Compound 19: 5-aminopentyl[(2-O-sulfonato-α-L-idopyranosyluronate)-(1→4)-O-(2-deoxy-2-sulfoamino-6-O-sulfonato-α-D-glucopyranoside)-(1→4)-O-(2-O-sulfonato-α-L-idopyranosyluronate)-(2-deoxy-2-sulfonato-6-O-sulfonato-α-D-glucopyranoside)-(1→4)-O-(2-O-sulfonato-α-L-idopyranosyluronate)-(2-deoxy-2-sulfoamino-6-O-sulfonato-α-D-glucopyranoside)-(1→4)-O-(2-O-sulfonato-α-L-idopyranosyluronate)-(2-deoxy-2-sulfoamino-6-O-sulfonato-α-D-glucopyranoside)-(1→4)-O-(2-O-sulfonato-α-L-idopyranosyluronate)-(2-deoxy-2-sulfoamino-6-O-sulfonato-α-D-glucopyranoside)-(1→4)-O-(2-O-sulfonato-α-L-idopyranosyluronate)]-(1→4)-O-2-deoxy-2-sulfoamino-6-O-sulfonato-α-D-glucopyranoside tetracosasodium salt. (HS12Lb)

$J_{2,3}=10.0$ Hz, $J_{2,1}=3.0$ Hz, 5H, $H-1^C$, $H-1^E$, $H-1^G$, $H-1^I$, $H-1^K$), 3.05 (t, $J_{2,1}=J_{2,3}=8.0$ Hz, $H-2^A$), 3.05 (t, J=7.5 Hz, H-e), 1.76-1.56 (m, 4H, H-d and H-b), 1.53-1.43 (m, 2H, H-c).

$^{13}$C NMR from $^1$H-$^{13}$C HSQC (100.6 MHz, $D_2O$, 50° C., ref $CH_3CN$) δ=114.8 ($C_m$ pMBn), 101.7 ($C-1^A$), 100.3-98.0 ($C-1^B$, $C-1^D$, $C-1^F$, $C-1^H$, $C-1^J$, $C-1^L$), 98.0-95.5 ($C-1^C$, $C-1^E$, $C-1^G$, $C-1^I$, $C-1^K$), 77.5-75.4 ($C-4^{Glucosaminyl\ moieties}$), 77.5-75.0 ($C-3^{Idurony\ moieties}$ and $C-4^{Idurony\ moieties}$), 73.0 ($C-3^A$) 70.9-68.5 ($C-2^{Idurony\ moieties}$, $C-5^{Idurony\ moieties}$, $C-5^{Glucosaminyl\ moieties}$, $C-3^{Glucosaminyl\ moieties}$), 69.9 (C-a), 67.8-65.3 ($C-6^{Glucosaminyl\ moieties}$), 60.2 ($C-2^A$), 58.1 ($C-2^C$, $C-2^E$, $C-2^G$, $C-2^I$, $C-2^K$), 39.7 (C-e), 28.1 (C-b), 26.2 (C-d).

ESI MS of $C_{77}H_{127}N_7O_{115}S_{18}$ calculated for $[M-H]^-$: 3563.9204, found: 3563.7568; 3483.9287 (−1SO3); 3403.9897 (−2SO3); 3324.0291 (−3SO3).

V.3. Chemical Synthesis of Conjugated Molecules of the Invention

HPLC and LCMS Conditions:
Monitoring of the coupling reactions and purity measurements were performed on an Agilent 1100 HPLC equipped with a Waters Symmetry 3.5 μm C18 300 Å (2.1×100 mm) column using linear gradients of $CH_3CN$ in 10 mM aqueous ammonium acetate buffer over 20 min at 1 ml/min flow rate. Detection: 215/230 nm.

LCMS analyses were performed on a Waters Q-TOF micro mass spectrometer coupled to an Alliance HPLC using the same column and solvents. In order to avoid phosphate ions injections, LCMS apparatus was only used to assess the product identity after a purification step. The data were acquired using the negative mode (ES−). Cone voltage was set to low values (10-20V) in order to minimize sulfate losses (SO3, 80 mass units).

Oligosaccharides were more prone to MS sulfate loss than their mCD4 conjugates.

Compounds Quantification
The starting oligosaccharides and final mCD4 conjugates quantities were quantified by amino acid analysis (AAA) on an HitachiL8800. For oligosaccharides, a 16 h, 95° C., HCl 6N, 2% phenol hydrolysis was used instead of the standard 20 h, 110° C., HCl 6N, 2% phenol conditions used for peptides/proteins hydrolysis. The glucosamine generated upon hydrolysis eluted after Phe.

Introduction of the Thiol Group on Oligosaccharide via SATP Bzl-Tetrasaccharide-SATP 20

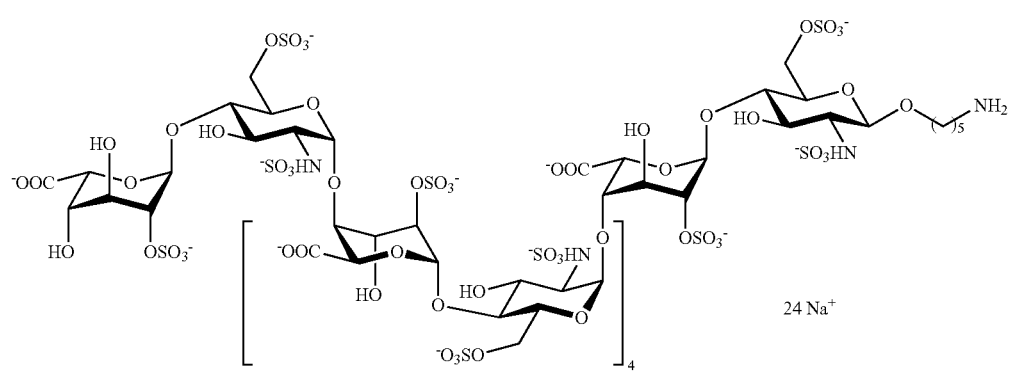

19

$Pd(OH)_2$ (20% on charcoal, 30 mg) was added to a solution of dodecasaccharide 18 (5.5 mg, 9.4 mol) in phosphate buffer (100 mM, pH 7.0, 400 μL) and tert-butanol (200 μL). The mixture was degased and stirred for 24 h under dihydrogen (1 atm). After 24 h at rt an additional portion of $Pd(OH)_2$ (20% on charcoal, 20 mg) was added, the mixture was degased and stirred for additional 24 h under hydrogen (1 atm). The suspension was filtered over ultrafree-MC filters (Amicon) and the catalyst was washed twice with phosphate buffer (33 mM, pH 7.0)/tert-butanol (3/1, 400 μL) then twice $CH_3CN/H_2O$ (1/1, 400 μL) in order to desorb compound 19 from the charcoal. After lyophilisation, the resulting solution was desalted on a PD-10 column (Pharmacia) and lyophilised giving 4 mg 19 (98%).

$^1$H NMR (400 MHz, $D_2O$, 50° C. ref $CH_3CN$) δ=5.37 (br. s, 5H, $H-1^C$, $H-1^E$, $H-1^G$, $H-1^I$, $H-1^K$), 5.20 (br. s, 5H, $H-1^B$, $H-1^D$, $H-1^F$, $H-1^H$, $H-1^J$), 5.17 (br. s, 1H, $H-1^L$), 4.80, 4.78 and 4.72 (3×br. s, $H-5^{Idurony\ moieties}$), 4.55 (d, $J_{1,2}=8.0$ Hz, $H-1^A$), 4.34-4.30 (m, $H-2^{Idurony\ moieties}$), 4.30-4.28 (m, $H-2^{Idurony\ moieties}$), 4.28-4.22 (m), 4.22-4.14 (m, $H-6_b$), 4.14-3.94 (m, 11H, $H-4^{Idurony\ moieties}$, $H-5^{Glucosaminyl\ moieties}$, $H-6_b$), 3.90-3.82 (m, 1H, H-a), 3.80-3.59 (m, 13H, $H-4^{Glucosaminyl\ moieties}$, $H-3^{Glucosaminyl\ moieties}$, H-a'), 3.27 (dd, To 0.5 mg of Bzl-tetrasaccharide 17 (MW: 1914, 8Na+; 0.25 µmole) in 660 µl of 50 mM sodium phosphate buffer pH8 were added 4×6 µl of SATP/DMSO solution (40 mg/ml; MW: 245; 4×0.5 µmole) over 15 min. Quantitative coupling was observed on the HPLC trace after 20 min. Bzl-tetrasaccharide 17 Rt=6.6 min; S-Acetylthiopropionate Bzl-tetrasaccharide 20 Rt=8.8 (12-32% gradient). The mixture was loaded on a C18 Sepak cartridge and the S-Acetylthiopropionate Bzl-tetrasaccharide 20 was eluted by 6 ml of 20% $CH_3CN/H_2O$. After lyophilization, the product was controlled by LCMS analysis.

Calculated monoisotopic mass for $C_{70}H_{89}N_3O_{42}S_7$ [M–H]⁻: 1866.2892.

Found: 1866.4692; 1786.5131 (–1$SO_3$); 1706.5300 (–2$SO_3$).

Bzl-dodecasaccharide-SATP 21

To 1.5 mg of Bzl-dodecasaccharide 18 (MW: 5293, 24Na+; 0.29 µmole) in 530 µl of 50 mM sodium phosphate buffer pH8 were added 4×6 µl of the SATP/DMSO solution over 15 min. Quantitative coupling was observed on the HPLC trace after 20 min. Bzl-dodecasaccharide 18 Rt=10.7 min; S-Acetylthiopropionate Bzl-dodecasaccharide 21 Rt=12.5 (5-25% gradient). The product was purified on a PD10 gel filtration column with water elution. First eluting fractions containing the S-Acetylthiopropionate Bzl-dodecasaccharide 21 (checked by MS infusion) were pooled and lyophilized. The product was controlled by LCMS analysis. Calculated monoisotopic mass for $C_{174}H_{213}N_7O_{118}S_{19}$ [M–H]⁻: 4894.5501. Found: 4894.6836; 4815.6084 (–1$SO_3$); 4734.5625 (–2$SO_3$); 4654.6660 (–3$SO_3$); 4575.6226 (–4$SO_3$).

Dodecasaccharide-SATP 22

To 0.5 mg of dodecasaccharide 19 (MW: 4092, 24Na+; 0.12 µmole) in 600 µl of 15 mM sodium phosphate buffer pH8 were added 4×6 µl of the SATP/DMSO solution over 15 min. Because of the very low 215/230 UV-absorption and the absence of retention on the C18 column of 19, the coupling reaction was not monitored by HPLC. After 20 min, the mixture was directly loaded on the PD10 column. The same purification protocol as above was performed. The product was controlled by LCMS analysis. The entirely sulfated ($C_{82}H_{133}N_7O_{117}S_{19}$) was not detected. Only –1$SO_3$, –2$SO_3$, –3$SO_3$ and –4 $SO_3$ and –5 $SO_3$ forms were detected. Calculated monoisotopic mass for $C_{82}H_{133}N_7O_{114}S_{18}$ [M–H–1$SO_3$]⁻: 3613.9724. Found: 3613.9536; 3533.9170 (–2$SO_3$); 3454.0190 (–3$SO_3$); 3374.0474 (–4$SO_3$); 3294.1528 (–5$SO_3$).

Coupling to mCD4-PEO2-Maleimide mCD4-$PEO_2$-Bzl-tetrasaccharide 23 (or mCD4-HS4Bz)

In order to follow tetrasaccharide-SATP 20 thiol deprotection by hydroxylamine and coupling onto mCD4-PEO2-Maleimide, a 12-22% (10 min)-82% (10 min) linear gradient of $CH_3CN$ in 10 mM ammonium acetate was used.

To Bzl-tetrasaccharide SATP 20 in 500 µl of 50 mM sodium phosphate buffer pH7.2, 100 µl of 0.5 M $NH_2OH$, HCl in 100 mM sodium phosphate buffer (pH adjusted to 7.2 by 4N NaOH) was added. Deprotection of the thiol function was monitored by HPLC. After 10 min, only 11% of Bzl-tetrasaccharide SATP 20 remained (Rt=8.7 min) while a new pick corresponding to the SH tetrasaccharide appeared at 7.4 min.

After 10 min, mCD4-PEO2-Mal (MW: 3207; 0.1 µmole) in 50 µl of $H_2O$ was added followed by a second same addition 5 min later.

After 20 min, the free thiol tetrasaccharide has totally disappeared. A new compound appeared at 16 min, corresponding to the mCD4-$PEO_2$-Bzl-tetrasaccharide 23. The conjugate was purified on a semi-preparative RP-HPLC column (Macherey Nagel 5 µm C18 300 A, 10×250 mm), using the same gradient but at a 6 ml/min flow rate. The purified product was controlled by LCMS analysis. Calculated average mass for $C_{204}H_{299}N_{43}O_{79}S_{13}$: 5034.7185. Found: 5034.7002.

The final purity (87%) of the mCD4-$PEO_2$-Bzl-tetrasaccharide 23 was assessed on the Symmetry column using a 20-50 linear gradient (Rt=11.06 min).

Yield: 276 µg quantified by AAA (24% from 17).

mCD4-$PEO_2$-Bzl-dodecasaccharide 24 (or mCD4-HS12Bz)

To Bzl-dodecasaccharide-SATP 21 in 500 µl of 50 mM sodium phosphate buffer pH7.2, 100 µl of the same hydroxylamine solution was added. A 5-25% (20 min)-85% (10 min) gradient was used to follow the deprotection and coupling reaction. After 20 min, the Bzl-dodecasaccharide-SATP 21 (Rt=12.7 min) disappeared generating the free thiol Bzl-dodecasaccharide (Rt=11.9). Three consecutive additions of mCD4-PEO-Mal solution (3×0.1 mm) were necessary to get the mCD4-$PEO_2$-Bzl-dodecasaccharide 24 conjugate quantitatively (Rt=24.8). The conjugate was purified by semi-preparative RP-HPLC using a 5-25% (10 min)-85% (20 min) gradient.

The purified product was controlled by LCMS analysis. Calculated average mass for $C_{308}H_{423}N_{47}O_{155}S_{25}$: 8065.6204. Found: 8065.1006; 7985.6000 (–1$SO_3$); 7905.2002 (–2$SO_3$).

The final purity (63%) of the mCD4-$PEO_2$-Bzl-dodecasaccharide 24 conjugate was assessed on the Symmetry column using a 20-50 linear gradient (Rt=9.37 min).

Yield: 643 µg quantified by AAA (28% from 18).

mCD4-$PEO_2$-dodecasaccharide 25 (or mCD4-HS12Lb or mCD4-$HS_{12}$)

Because of the very low UV absorbance and absence of retention on the C18 column of the dodecasaccharide-SATP 22, the deprotection step could not be followed by HPLC. To the dodecasaccharide-SATP 22 in 500 µl of 50 mM sodium phosphate buffer pH7.2, 150 µl of the same hydroxylamine solution was added. After 20 min, positive Ellmann test performed on the reaction mixture indicated thiol deprotection. mCD4-$PEO_2$-Mal solution was added (3×0.1 µmole). Injection of an aliquot of the coupling reaction (10 min) showed a new product (Rt=8.4) in conjunction with some remaining mCD4-$PEO_2$-Mal (Rt=11.8) in the 20-50% gradient.

The conjugate was purified by semi-preparative RP-HPLC using the conditions as for the mCD4-$PEO_2$-Bzl-dodecasaccharide 24 conjugate.

The purified product was controlled by LCMS analysis. Calculated average mass for $C_{216}H_{343}N_{47}O_{154}S_{25}$ 6863.9738. Found: 6863.1001; 6763.2000 (–1$SO_3$); 6703.5005 (–2$SO_3$).

The final purity (100%) of the mCD4-$PEO_2$-dodecasaccharide 25 conjugate was assessed on the Symmetry column using a 20-50 linear gradient (Rt=8.37 min)

Yield: 321 µg quantified by AAA (39% from 19).

Example VI

Biological Activity

In this part mCD4 refers to miniCD4.

VI.1. Methods

Two different gp120 were used, originating from a type X4 isolate (gp120 MN) and a type R5 isolate (gp120 YU2). The capacity of different molecules to inhibit gp120 interactions with various receptors or co-receptors is measured by surface plasmonic resonance (Biacore). To do this, three compounds are immobilized on the surface of a biosensor (Sensorchip CM 4 Biacore) in accordance with the described procedure (Vives et al. *J. Biol. Chem.* 279, 54327-54333, 2005). These are CD4, HS (or heparin) and a monoclonal antibody (mAb 17b). This antibody recognizes the epitope induced by CD4 and mimics co-receptor CCR5 or CXCR4. These three surfaces represent the three main molecules on the cell surface recognized by gp120 (CD4, co-receptors and HS).

In the set of experiments described below, gp120 (light lines on FIGS. 4 to 6) alone or pre-incubated with the compound to be tested (heavy lines on FIGS. 4 to 6) is injected onto these surfaces, and the interaction signal is measured as a function of time for five minutes. The difference between the light line and the heavy line shows the inhibitory capacity of the tested compound vis-à-vis interactions between gp120 and the molecule immobilized on the biosensor.

VI.2. Results

Analysis of mCD4, HS12Lb (molecule 19) and mCD4-HS12Lb (molecule 25) molecules.
Onto the CD4 surface (gp120 and inhibitors at 100 nM):
The compound HS12Lb alone has no effect on the gp120/CD4 interaction and the results are not shown here.
It is to be noted that the compound mCD4-HS12Lb inhibits the gp120/CD4 interaction more strongly than mCD4, and this for gp120 X4 and R5 (see FIG. 4).
Onto the HS surface (gp120 and inhibitors at 40 nM)
gp120 YU2 binds only very weakly to HS (as for the set of type R5 gp120). The results obtained on this surface are therefore not shown.
mCD4 has no effect on the gp120/HS interaction. Compound HS12Lb partially inhibits interaction with the concentration conditions used. A mixture of mCD4 and HL12Lb (mCD4+HS12Lb) not bound to each other has the same activity. On the other hand, mCD4-HS12Lb conjugates totally inhibit the interaction, demonstrating a powerful cooperative effect linked to conjugation (see FIG. 5).
Onto the mAb 17b surface (gp120 and inhibitors at 40 nM):
gp120 bind only very slightly (YU2) or not at all (MN) to antibody 17b in the absence of mCD4 (light lines in FIG. 6). The presence of mCD4 greatly enhances this reaction (heavy lines of upper diagrams in FIG. 6). On the other hand, mCD4-HS12Lb compounds totally inhibit the interaction (heavy lines of lower diagrams in FIG. 6), validating the mechanism described in FIG. 1 (exposure of the CD4i epitope by mCD4 and blockage of this by the HS12Lb molecule).

The following experiment was carried out in order to demonstrate the potentializing effect of covalent binding between mCD4 and HS12Lb:

40 nM of gp120 (MN or YU2) was co-incubated with increasing concentrations (from 0 to 80 nM) of covalently linked mCD4-HS12Lb (in white in FIG. 7) or not linked mCD4+HS12Lb (in black in FIG. 7), then injected onto a 17b surface. The quantity of gp120 bound to the antibody is measured at the end of the injection. It should be remembered that gp120 only binds to 17b when CD4i is unmasked, i.e. in the presence of mCD4 or sCD4.

It is found that the covalent molecule (mCD4-HS12Lb) strongly inhibits the gp120-17b interaction while the mixture of the two molecules (mCD4+HS121B) has the opposite effect: the effect of mCD4 is predominant (unmasking of the CD4i site and therefore binding of gp120 to 17b), and inhibition by HS12Lb only starts to appear at a high concentration for gp120 of type MN. For gp120 of type YU2, HS12Lb is not an inhibitor, in agreement with the observation that YU2 alone does not bind at all or only very slightly to HS (see FIG. 7).

Analysis of peptide GPR1, HS4Bz (17), HS12Bz (18), HS12Lb (19) molecules mixed with mCD4 versus mCD4-GPR1, mCD4-HS4Bz (23), mCD4-HS12Bz (24) and mCD4-HS12Lb (25) conjugates The comparison of the inhibitory capacity of molecules linked or not linked to mCD4, as described above, has been done for molecules other than HS12Lb. This was performed for the following molecules:
1. Peptide GPR1, (SEQ ID No 4)
2. Oligosaccharide HS4Bz (17),
3. Oligosaccharide HS12Lb (18),
4. Oligosaccharide HS12Bz (19),
mixed with mCD4, or:
A. mCD4-GPR1,
B. mCD4-HS4Bz (23),
C. mCD4-HS12Bz (24),
D. mCD4-HS12Lb (25),
conjugates Peptide GPR1 is a synthetic peptide derived from the extracellular N-terminus region of the receptor coupled to protein G, GPR1 (Jinno-Oue et al., J Biol chem. 2005 Sep. 2; 280 (35):30924-34. Epub 2005 May 26). It is used as an organic molecule, in comparison to the polyanionic polysaccharide according to the present invention. The peptide GPR1 may have the sequence SEQ ID No 3 or SEQ ID No 4.

In the following experiment, 40 nM of gp120 was co-incubated with 80 nM of mCD4 and 80 nM of the various molecules mentioned above, or 80 nM of corresponding covalent conjugates. The interaction with 17b is measured. T represents measurement of gp120 binding to mCD4 alone.

It is noted that the molecules tested, when not bound to mCD4, have varying degrees of inhibitory ability (in black in FIG. 8) whereas when they are covalently bound to mCD4 (in white in FIG. 8), all these molecules inhibit the interaction very strongly.

VI.3. Conclusion

The work described above demonstrates the inhibitory activity of a hybrid molecule consisting of mCD4 (or any other molecule that binds to gp120 and is capable of exposing the co-receptor recognition site) covalently bound to a molecule capable of recognizing the co-receptor recognition site.

The role of this hybrid molecule is to bind to gp120 and expose the CD4i site (via mCD4) and to block the interaction site with the co-receptors (via the conjugate).

The particularly significant points are:
Simultaneous inhibition of interaction between gp120 with CD4, co-receptors and HS, in the nM concentration ranges,
Very high cooperative action induced by conjugation of two molecules, and
Inhibitory activity for type X4 and R5 isolates.

Example VII

Biological Activity—Supplemental Experiments

VII.1. Affinity

The method describes in the following articles has been used for this study:

Vivès R. R. et al. *Journal of Biological Chemistry* 2005, 280, 21353-21357 (see Materials and methods—Surface Plasmon resonance-based binding assays), and Crublet E. et al. *Journal of Biological Chemistry* 2008, 283, 15193-15200 (see Materials and methods—Surface Plasmon resonance-based binding assays).

TABLE 5

Association and dissociation rate constants of mCD4-$HS_{12}$ for MN and YU2 gp120

| Model | gp120 | $k_{on}1$ (1/Ms) | $k_{off}1$ (1/s) | Kd = $k_{off}1/k_{on}1$ (nM) | $k_{on}2$ (1/RUs) | $k_{off}2$ (1/s) | $\chi^2$ |
|---|---|---|---|---|---|---|---|
| Langmuir | MN (X4) | $10.6 \; 10^5$ | $3.9 \; 10^{-3}$ | 3.7 | * | * | 2.7 |
| Langmuir | YU2 (R5) | $12.7 \; 10^5$ | $3.4 \; 10^{-3}$ | 2.7 | * | * | 1.6 |
| Bivalent | MN (X4) | $5.5 \; 10^5$ | $5.5 \; 10^{-3}$ | 10 | $6.0 \; 10^{-3}$ | $3.4 \; 10^{-2}$ | 0.8 |
| Bivalent | YU2 (R5) | $6.4 \; 10^5$ | $4.6 \; 10^{-3}$ | 7.2 | $7.2 \; 10^{-3}$ | $2.3 \; 10^{-2}$ | 0.4 |

* Not available for the 1:1 langmuir binding model.

Figure 9A:
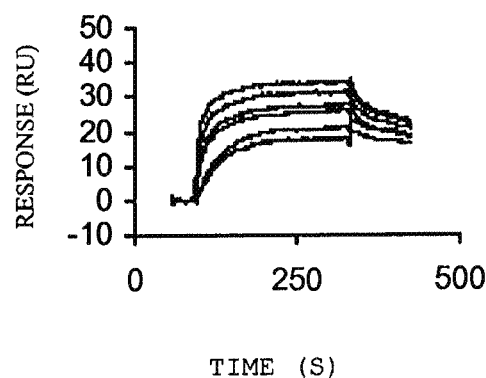
Figure 9B:
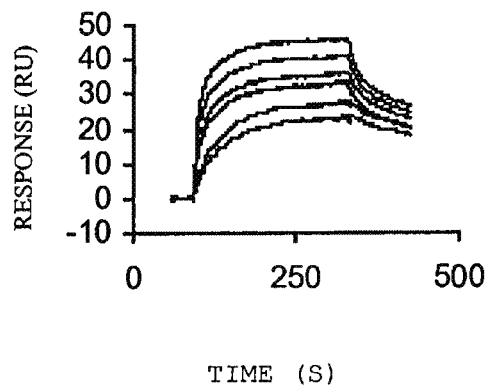
Figure 9C:
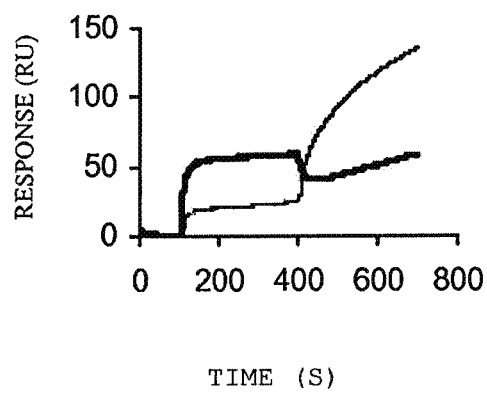
Figure 9D:
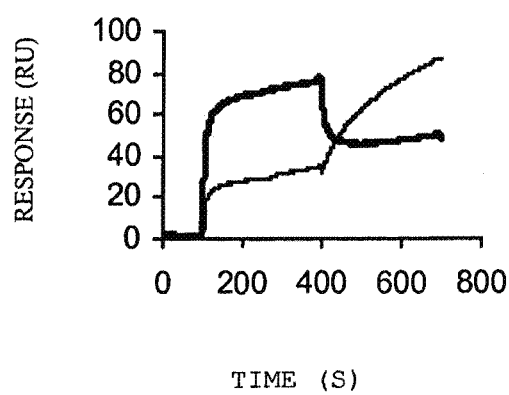
Figure 9E:
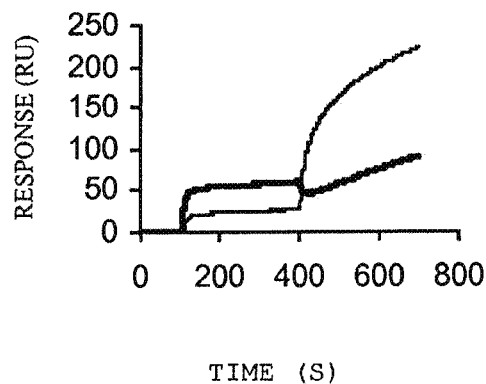
Figure 9F:
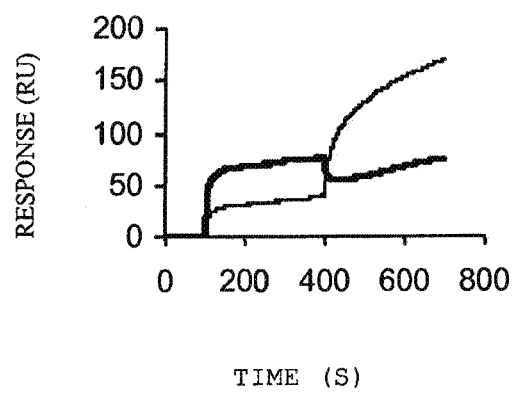

Association ($k_{on}$) and dissociation ($k_{off}$) rate constants (the mean of two independent analyses) of mCD4-$HS_{12}$ (25) for MN and YU2 gp120 were determined by fitting the primary data of FIGS. 9a,b using the Biaeval 3.1 software. Evaluation of the sensorgrams using a simple "1:1 langmuir" binding model returned affinity values (Kd=$k_{off}/k_{on}$) of 3.7 and 2.7 nM for MN and YU2 gp120, respectively. However, some deviations of the data from this model were observed, as measured by the $\chi^2$ parameter (which describes the closeness of the fit). Consistent with the bivalent nature of mCD4-$HS_{12}$, the fit was improved using a "bivalent binding" model ($\chi^2$ parameters were now 0.8 and 0.4 instead of 2.7 and 1.6 for the previous model). According to this model, the initial binding step is thus characterized by the indicated association ($k_{on}1$) and dissociation ($k_{off}1$) rate constants, which gave rise to a dissociation equilibrium constant of 10 nM for MN and 7.2 nM for YU2 gp120. These affinities should be further increased by the second binding step. However this cannot be quantified here because, for the bivalent binding model, the association rate constant for the second binding site is in $RU^{-}s^{-1}$ (the reaction involves the complex (in RU) binding to ligand (also in RU)), and not in $M^{-1}s^{-1}$. Nevertheless these data indicate that mCD4-$HS_{12}$ binds to both X4 and R5 gp120 with affinities in the low nM range and suggest a bivalent binding mechanism (see FIG. 9c-d).

VII. 2. Antiviral Activity

VII.2.1. Infection of Peripheral Blood Mononuclear Cells with HIV-1-LAI and BaL Strains and Inhibition Assay The X4-tropic HIV-1-LAI (Barre-Sinoussi, Science 220, 868-71, 1983) or the R5-tropic HIV-1/Ba-L (Gartner et al, Science 233, 215-9, 1986) strains were amplified and titrated in vitro on Phytohemaglutinin-P (PHA-P)-activated peripheral blood mononuclear cells (PBMC). Tissue culture infectious doses were calculated using Kärber's formula (Kärber, Arch. Exp. Path. Pharmak. 162, 480-483, 1931). For the antiviral assay, PHA-P-activated PBMC were pre-treated for 30 minutes with six concentrations of each drug (1:5 dilutions between 1 μM and 320 μM) and infected with one hundred 50% tissue culture infectious doses (TCID50) of either the X4-tropic LAI or R5-tropic Ba-L strain. Drugs were maintained throughout the culture, and cell supernatants were collected at day 7 post-infection and stored at −20° C. Azidothymidine (AZT) was used in these experiments as an internal control. Viral replication was measured by quantifying reverse transcriptase (RT) activity in cell culture supernatants using the RetroSys HIV RT kit (Innovagen).

In parallel, cytotoxicity of the samples was evaluated in uninfected PHA-P-activated PBMC by a methyltetrazolium salt (MTT) assay on day 7. Experiments were performed in triplicate and 50, 70 and 90% effective doses and cytotoxic doses were calculated using SoftMaxPro software.

TABLE 6

Anti viral activity of mCD4, $HS_{12}$ and mCD4-$HS_{12}$

| | LAI (X4) | | | /Ba-L (R5) | | |
|---|---|---|---|---|---|---|
| | $ED_{50}$ | $ED_{70}$ | $ED_{90}$ | $ED_{50}$ | $ED_{70}$ | $ED_{90}$ |
| mCD4 | 244 ± 18 | 377 ± 169 | 560 ± 222 | >500 | >500 | >500 |
| $HS_{12}$ (19) | >500 | >500 | >500 | >500 | >500 | >500 |
| mCD4-$HS_{12}$ (25) | 1.4 ± 0.9 | 2.05 ± 0.55 | 3.0 ± 0.65 | 2.4 ± 1.9 | 4.9 ± 0.3 | 11.1 ± 7.6 |
| AZT | 1.8 ± 0.85 | 2.75 ± 1.3 | 5.6 ± 2.5 | 6.6 ± 0.8 | 14 ± 8.1 | 45 ± 44 |

PHA-P-activated PBMC were treated with each of the drug under investigation (1:5 dilutions between 1 μM and 320 μM) and infected with 100 $TCID_{50}$ of either HIV-1-LAI (X4 tropic) or /Ba-L (R5 tropic) strain. Molecules and viruses were maintained throughout the culture, and cell supernatants were collected at day 7 post-infection from which reverse transcriptase activity was quantified. Experiments were performed in triplicate and 50, 70 and 90% effective doses (ED), in nM (±S.D.) were calculated using SoftMaxPro software.

None of these molecules showed cytotoxicity up to 1 µM.

TABLE 7

Anti viral activity of mCD4-GPR1, mCD4-HS4Bzl, mCD4-HS12Bzl

| | VIH-1-LAI | | | Cytotoxicity | | | VIH-1/Ba-L | | |
|---|---|---|---|---|---|---|---|---|---|
| | ED50 | ED70 nM | ED90 | CT50 | CT70 nM | CT90 | ED50 | ED70 nM | ED90 |
| mCD4_GPR1 | 66 | 67 | 67.5 | >1000 | >1000 | >1000 | 205 | 231 | 309 |
| mCD4_HS4Bzl | 83 | 84 | 86 | >1000 | >1000 | >1000 | 184 | 195 | 211 |
| mCD4_HS12Bzl | >1000 | >1000 | >1000 | >1000 | >1000 | >1000 | >1000 | >1000 | >1000 |
| HS12Bzl | 343 | 388 | 471 | >1000 | >1000 | >1000 | 200 | 212 | 234 |
| HS4Bzl | >1000 | >1000 | >1000 | >1000 | >1000 | >1000 | Non tested: Insufficient quantity | | |
| GPR1 | >1000 | >1000 | >1000 | >1000 | >1000 | >1000 | >1000 | >1000 | >1000 |
| mCD4 | 387 | >1000 | >1000 | >1000 | >1000 | >1000 | >1000 | >1000 | >1000 |
| AZT | 8 | 15 | 41 | >200 | >200 | >200 | 10 | 28 | 111 |

VII.2.2. Negative Control on VSV—Infection of Peripheral Blood Mononuclear Cells with HIV Pseudotyped Reporter Viruses VSV-G pseudotyped viral particles were generated by a single infectious cycle in HEK293T cells, and co-transfected with the plasmid pNL4-3 env-Luc and a plasmid permitting expression of the envelop G protein from Vesicular Stomatitis Virus (VSV-G). The pNL4-3 env-Luc plasmid derives from the infectious proviral clone HIV-1 NL4-3 and carries a frameshift in the env gene that renders it noninfectious. The firefly luciferase (Luc) reporter gene replaces the NL4-3 nef gene. The infectious HIV-1 proviral clones pNL4-3 Luc (a gift from Dr. J. Alcami, Madrid Spain) were generated by replacing the corresponding HIV nef by the Luc genes. Infectious viral preparations were generated by transfecting the constructs in HEK293T cells. PBMC were isolated from healthy blood donors and blasted with phytohemagglutinin and IL-2 for 48 hours. Viral preparations were titrated in HeLaCD4+ CXCR4+ CCR5+ cells and the amount of virus used for PBMC infection was normalised with respect to the Luc enzymatic activity measured in cell lysates. After 2 hours of infection (in the presence or absence of mCD4-HS$_{12}$, cells were exhaustively washed and seeded in microplate wells ($2\times10^5$ cells/well) for an additional 48 hours, after which Luc enzymatic activities were measured in the PBMC lysates using a LB 940 Berthold Mithras luminometer apparatus (Berthold Technologies, Germany).

TABLE 8

Anti viral activity of mCD4-HS$_{12}$ towards NL4-3 HIV-1 and Δenv + VSVg-HIV-1

| | mCD4-HS$_{12}$ (nM) | | | |
|---|---|---|---|---|
| Virus | 0 | 5 | 20 | 100 |
| NL4-3-renilla | 4.38 ± 0.49 | 0.142 ± 0.64 | 0.047 ± 0.06 | 0.035 ± 0.05 |
| Δenv + VSVg-luc | 6.15 ± 0.36 | 8.97 ± 0.26 | 6.70 ± 2.9 | 6.50 ± 1.13 |

Luciferase activity (RLU×10$^{-5}$) was measured at day 2 following infection of PBMC with 10$^6$ RLU of NL4-3 renilla or Δenv+VSVg-luc viruses, treated with the indicated concentrations of mCD4-HS$_{12}$.

VII.3. Conclusion

Our study thus shows that relatively small synthetic molecules, comprising a 3 kDa CD4 mimetic linked to small heparin fragments or more generally polyanionic compounds, can efficiently mimic several large gp120 ligands, including CD4 and coreceptor binding site recognizing mAbs. Based on the ability of the CD4 mimetic to render the coreceptor binding site accessible to HS-mediated blockade, these molecules simultaneously target two critical and highly conserved structures on gp120, and consequently display a strong antiviral activity. Remarkably, the conjugates described in the present invention neutralize both R5- and X4-tropic HIV-1, a significant advantage since the efficacy of CCR5-specific antagonists could be jeopardized by the emergence of viral strains that utilize CXCR4, for which no inhibitors are yet available.

The design of a miniCD4 bearing a single site of derivatisation judiciously located within the miniCD4 sequence brings a great improvement for the synthesis and biological activity of the mCD4 based conjugates.

ABBREVIATIONS

Fmoc: 9-fluorenylmethyloxycarbonyl
DMF: Dimethylformamide
HATU: hexafluorophosphate N-oxide of N[(dimethylamino)-1H-1,2,3-triazolo[4,5-b]pyridin-1-ylmethylene]-N-methylmethanaminium
DIEA: diisopropylethylamine
SPDP: N-succinimidyl-3(2-pyridyldithio)propionate
TFA: trifluoroacetic acid
EDT: ethanedithiol
TIS: triisopropylsilane
DTT: 1,4-dithiothreitol
MPLC: medium pressure liquid chromatography
ES$^+$MS: electrospray mass spectrometry, positive mode
GSH: reduced glutathion
GSSG: oxidised glutathion
HPLC: high-performance liquid chromatography
RP-HPLC: reverse phase high-performance liquid chromatography
SMPH: succinimidyl-6-[β-maleimidopropionamido]hexanoate
SATP: N-succinimidyl-S-acetylthioproprionate
RT: room temperature
Rt: retention time
TMSOTf: trimethylsilyl triflate
TBDMSOTf: tert-butyl-dimethyl-silyl triflate
Cbz: benzyloxycarbonyl
pMBn: p-methoxybenzyl
Bn: benzyl Ac: acetyl
Me: methyl
Et: ethyl
eq: equivalent
NMR: Nuclear Magnetic Resonance
IR: infrared
HSQC: Heteronuclear Single Quantum Coherence
HRMS: high resolution mass spectrum ESI: electrospray ionisation
MALDI-TOF: Matrix Assisted Laser Desorption/Ionization Time-of-Flight
LC-ESI-TOF-MS: Liquid chromatography/electrospray ionization Time-of-Flight mass spectrometry
LCMS: Liquid chromatography/Mass spectrometry
DMSO: Dimethylsulfoxide

The invention claimed is:

1. A conjugated molecule comprising a peptide derived from the CD4 receptor, said peptide being coupled to an organic molecule by means of a linker, wherein:

the peptide derived from the CD4 receptor comprises the following general sequence (I):

(SEQ ID NO: 5)
$\text{Xaa}^f\text{-P1-Lys-Cys-P2-Cys-P3-Cys-Xaa}^g\text{-Xaa}^h\text{-Xaa}^i\text{-}$
$\text{Xaa}^j\text{-Cys-Xaa}^k\text{-Cys-Xaa}^l\text{-Xaa}^m$, (I)

in which:

P1 represents 3 to 6 amino acid residues,

P2 represents 2 to 4 amino acid residues,

P3 represents 6 to 10 amino acid residues, $\text{Xaa}^f$ represents N-acetylcysteine (Ac-Cys) or thiopropionic acid (TPA), $\text{Xaa}^g$ represents Ala or Gln, $\text{Xaa}^h$ represents Gly or (D)Asp or Ser, $\text{Xaa}^i$ represents Ser or His or Asn, $\text{Xaa}^j$ represents biphenylalanine (Bip), phenylalanine or [beta]-naphthylalanine, $\text{Xaa}^k$ represents Thr or Ala, $\text{Xaa}^l$ represents Gly, Val or Leu, and $\text{Xaa}^m$ represents —NH₂ or —OH, the amino acid residues in P1, P2 and P3 being natural or non-natural, identical or different, said residues of P1, P2 and P3 being all different from the Lys residue and P1, P2 and P3 having a sequence in common or not, and the organic molecule has the following general structure (II):

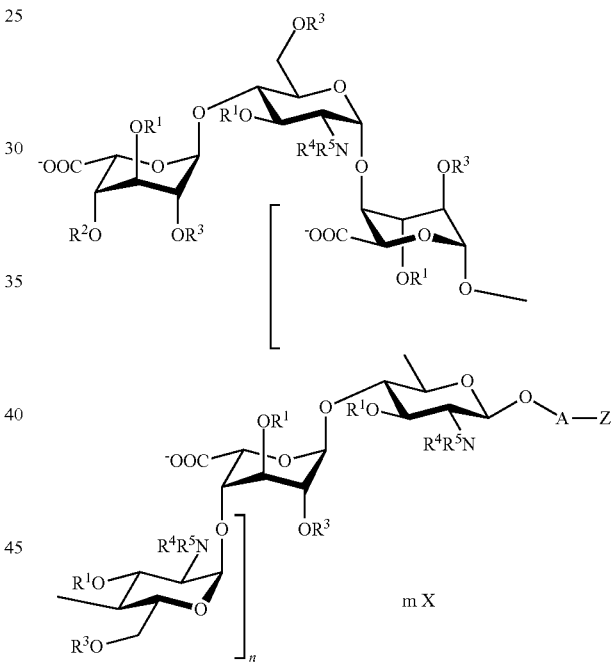

in which:

n represents 0, 1, 2, 3, 4, 5, 6, 7, 8, 9 or 10,

X represents an inorganic couterion or an organic counterion, m represents the number of negative charges of the molecule, each $R^1$ is an identical radical or a different radical represented by a hydrogen atom or an O-Protecting group GP, $R^2$ represents a hydrogen atom or an O-Protecting group GP', wherein GP and GP' are identical or different, each $R^3$ is an identical radical or a different radical represented by a hydrogen atom, a sulphate, a phosphate or any anionic group, each $R^4$ is an identical radical or a different radical represented by a hydrogen atom, a sulfate, an alkyl or an acyl group, each $R^5$ is an identical radical or a different radical represented by a hydrogen atom, an alkyl or an acyl group, A represents a group chosen from those of formula:
—$(CH_2)_p$—NH—CO—$(CH_2)_q$—, —$(CH_2$—$CH_2)$—$(O$—$CH_2$—$CH_2)_p$—NH—CO—$(CH_2)_q$—, —$(CH_2)_p$—NH—CO—$(CH_2$—$CH_2$—$O)_q$—$(CH_2$—$CH_2)$—, and —$(CH_2$—$CH_2)$—$(O$—$CH_2$—$CH_2)_p$—NH—CO—$(CH_2$—$CH_2$—$O)_q$—$(CH_2$—$CH_2)$—, wherein p represents an integer from 1 to 10 and q represents an integer from 1 to 10, and Z represents a thiol group or a maleimide group, the linker resulting from the coupling of a bifunctional compound, respectively, with the peptide derived from the CD4 receptor and the organic molecule, the said bifunctional compound incorporating two active groups, wherein one of the two active groups is capable of forming a covalent bond with the free amino group (—$NH_2$) of the residue of the amino acid Lys present in general sequence (I), and the other active group is capable of forming a covalent bond with the Z functional group of the organic molecule, wherein the sequence of the peptide derived from the CD4 receptor of general sequence (I) is selected from the group consisting of SEQ ID NO: 1 and SEQ ID NO: 2.

2. The conjugated molecule according to claim 1, wherein each $R^1$ radical is identical.

3. The conjugated molecule according to claim 1, wherein each $R^1$ radical is selected from the group consisting of: a hydrogen atom, a methyl group, and a benzyl group.

4. The conjugated molecule according to claim 1, wherein $R^2$ is selected from the group consisting of: a hydrogen atom and a p-methoxybenzyl group.

5. The conjugated molecule according to claim 1, wherein the conjugated molecule is selected from the group consisting of:

(SEQ ID NO: 1)

TPA-Asn-Leu-His-Lys-cyc-Gln-Leu-Arg-Cys-Ser-Ser-Leu-Gly-Leu-Leu-Gly-Arg-Cys-Ala-gly-Ser-Bip-Cys-Ala-Cys-Val-$CONH_2$, -continued
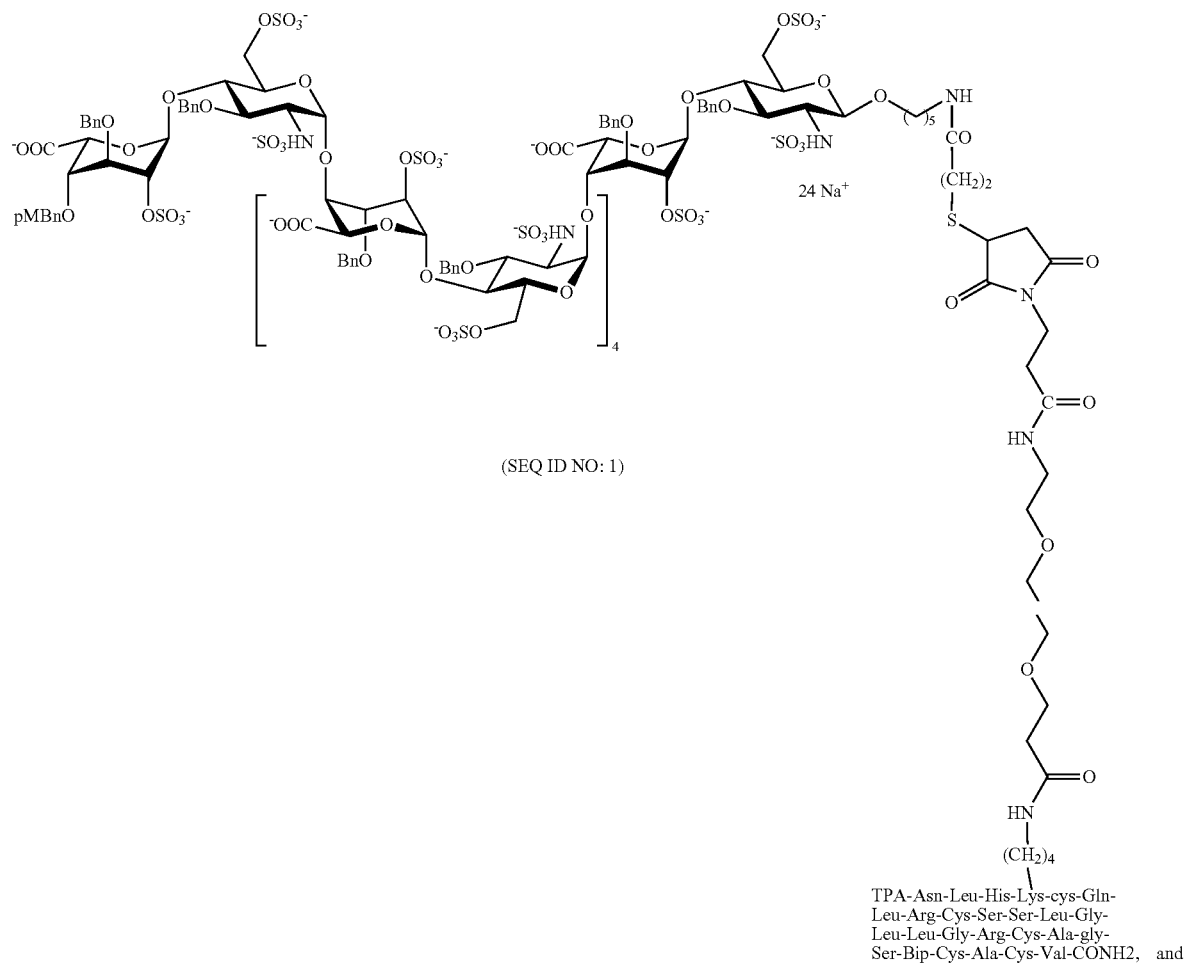
(SEQ ID NO: 1)
TPA-Asn-Leu-His-Lys-cys-Gln-
Leu-Arg-Cys-Ser-Ser-Leu-Gly-
Leu-Leu-Gly-Arg-Cys-Ala-gly-
Ser-Bip-Cys-Ala-Cys-Val-CONH2, and
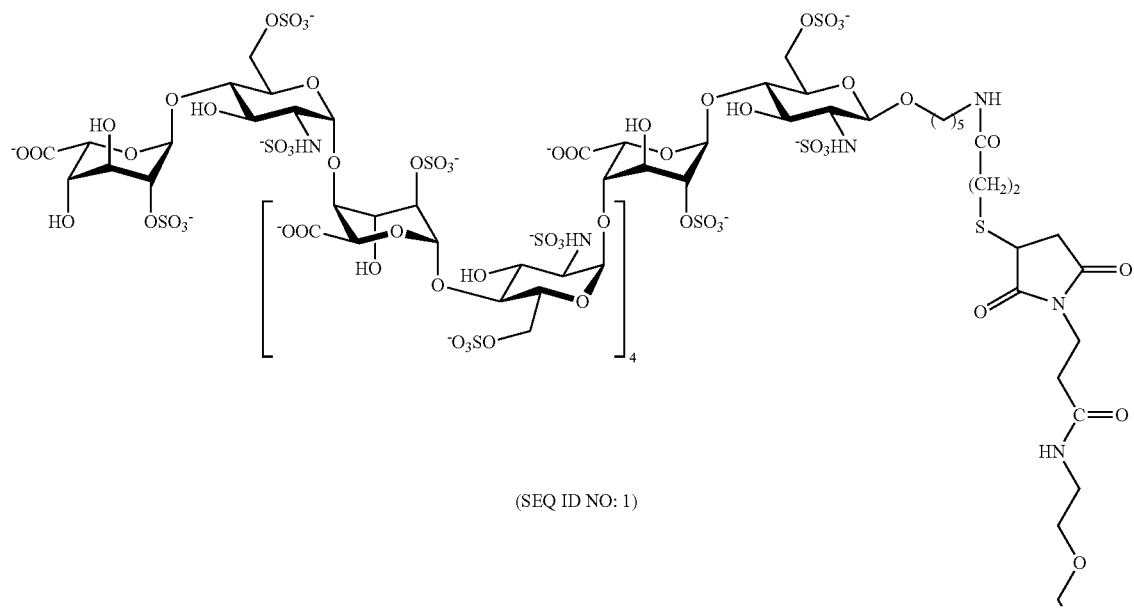
(SEQ ID NO: 1)

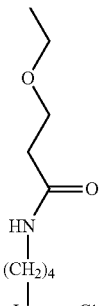

TPA-Asn-Leu-His-Lys-cys-Gln-
Leu-Arg-Cys-Ser-Ser-Leu-Gly-
Leu-Leu-Gly-Arg-Cys-Ala-gly-
Ser-Bip-Cys-Ala-Cys-Val-CONH2.

6. The conjugated molecule according to claim 1, wherein n represents 0, 1, 2, 3, 4, or 5.

7. The conjugated molecule according to claim 1, wherein X represents an inorganic counterion selected from the group consisting of $Na^+$, $K^+$, $Li^+$, and $Mg^{2+}$; or an organic counterion selected from the group consisting of $R_3NH^+$ and $R_4N^+$, with each R representing, independently from each other, an alkyl group.

8. The conjugated molecule according to claim 1, wherein A represents a group of formula $-(CH_2)_5-NH-CO-(CH_2)_2-$.

9. The conjugated molecule according to claim 1, wherein the bifunctional group is selected from the group consisting of:

NHS-$PEO_n$-Maleimide where n is between 2 and 24, Sulfo-KMUS (N-[k-maleimidoundecanoyloxy]sulfosuccinimide ester), LC-SMCC (succinimidyl-4-[N-maleimidomethyl]cyclohexane-1-carboxy-[6-amidocaproate]), KMUA (N-k-maleimidoundecanoic acid), SMPB (succinimidyl 4-[p-maleimidophenyl]butyrate), Sulfo-SMPB (sulfosuccinimidyl 4-[p-maleimidophenyl]butyrate), Sulfo-SIAB (N-sulfosuccinimidyl[4-iodoacetyl]aminobenzoate), SIAB (N-succinimidyl[4-iodoacetyl]aminobenzoate), Sulfo-EMCS ([N-e-maleimidocaproyloxy]sulfosuccinimide ester), EMCA (N-e-maleimidocaproic acid), EMCS ([N-e-maleimidocaproyloxy]succinimide ester), SMCC (succinimidyl 4-[N-maleimidomethyl]cyclohexane-1-carboxylate), Sulfo-SMCC (sulfosuccinimidyl 4-[N-maleimidomethyl]cyclohexane-1-carboxylate), MBS (m-maleimidobenzoyl-N-hydroxy succinimide ester), Sulfo-MBS (m-maleimidobenzoyl-N-hydroxysulfosuccinimide ester), GMBS (N-[g-maleimidobutyryloxy]succinimide ester), Sulfo-GMBS (N-[g-maleimidobutyryloxy]sulfosuccinimide ester), SPDP (N-succinimidyl-3-(2-pyridyldithio)propionate), SBAP (succinimidyl 3-[bromoacetamido]propionate), BMPS (N-[[beta]-maleimidopropyloxy]succinimide ester), BMPA (N-[beta]-maleimidopropionic acid), AMAS N-(a-maleimidoacetoxy)succinimide ester), SIA (N-succinimidyl iodoacetate), SMPH (succinimidyl-6-[betamaleimidopropionamido]hexanoate), SATA (N-succinimidyl-S-acetylthioacetate) and SATP (N-succinimidyl-S-acetylthiopropionate).

10. A pharmaceutical composition comprising a conjugated molecule according to claim 1 and a pharmaceutically acceptable vehicle.

11. A method for the treatment of Acquired Immunodeficiency Syndrome (AIDS) comprising the administration of an effective amount of a conjugated molecule according to claim 1 to a person in need thereof.

* * * * *

```
                        SEQUENCE LISTING

<160> NUMBER OF SEQ ID NOS: 7

<210> SEQ ID NO 1
<211> LENGTH: 26
<212> TYPE: PRT
<213> ORGANISM: Artificial Sequence
<220> FEATURE:
<223> OTHER INFORMATION: Description of Artificial Sequence: Synthetic
      CD4 derived peptide
<220> FEATURE:
<221> NAME/KEY: MOD_RES
<222> LOCATION: (1)..(1)
<223> OTHER INFORMATION: TPA-Asn
<220> FEATURE:
<221> NAME/KEY: MOD_RES
<222> LOCATION: (22)..(22)
<223> OTHER INFORMATION: Bip
<220> FEATURE:
<221> NAME/KEY: MOD_RES
<222> LOCATION: (26)..(26)
<223> OTHER INFORMATION: Val-NH2

<400> SEQUENCE: 1

Asn Leu His Lys Cys Gln Leu Arg Cys Ser Ser Leu Gly Leu Leu Gly
1               5                   10                  15

Arg Cys Ala Gly Ser Xaa Cys Ala Cys Val
            20                  25

<210> SEQ ID NO 2
<211> LENGTH: 26
<212> TYPE: PRT
<213> ORGANISM: Artificial Sequence
<220> FEATURE:
<223> OTHER INFORMATION: Description of Artificial Sequence: Synthetic
      CD4 derived peptide
<220> FEATURE:
<221> NAME/KEY: MOD_RES
<222> LOCATION: (1)..(1)
<223> OTHER INFORMATION: TPA-Asn
<220> FEATURE:
<221> NAME/KEY: MOD_RES
<222> LOCATION: (22)..(22)
<223> OTHER INFORMATION: Bip

<400> SEQUENCE: 2

Asn Leu His Lys Cys Gln Leu Arg Cys Ser Ser Leu Gly Leu Leu Gly
1               5                   10                  15

Arg Cys Ala Gly Ser Xaa Cys Ala Cys Val
            20                  25

<210> SEQ ID NO 3
<211> LENGTH: 27
<212> TYPE: PRT
<213> ORGANISM: Artificial Sequence
<220> FEATURE:
<223> OTHER INFORMATION: Description of Artificial Sequence: Synthetic
      GPR1 peptide
<220> FEATURE:
<221> NAME/KEY: MOD_RES
<222> LOCATION: (27)..(27)
<223> OTHER INFORMATION: Cys-NH2
```

```
<400> SEQUENCE: 3

Met Glu Asp Leu Glu Glu Thr Leu Phe Glu Glu Phe Glu Asn Tyr Ser
1               5                   10                  15

Tyr Asp Leu Asp Tyr Tyr Ser Leu Glu Ser Cys
            20                  25

<210> SEQ ID NO 4
<211> LENGTH: 27
<212> TYPE: PRT
<213> ORGANISM: Artificial Sequence
<220> FEATURE:
<223> OTHER INFORMATION: Description of Artificial Sequence: Synthetic
      GPR1 peptide

<400> SEQUENCE: 4

Met Glu Asp Leu Glu Glu Thr Leu Phe Glu Phe Glu Asn Tyr Ser
1               5                   10                  15

Tyr Asp Leu Asp Tyr Tyr Ser Leu Glu Ser Cys
            20                  25

<210> SEQ ID NO 5
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Ac-Cys or not present
<220> FEATURE:
<221> NAME/KEY: MOD_RES
<222> LOCATION: (2)..(7)
<223> OTHER INFORMATION: Any amino acid except Lys and this region may
      encompass 3 to 6 residues wherein some positions may be absent
<220> FEATURE:
<221> NAME/KEY: MOD_RES
<222> LOCATION: (10)..(13)
<223> OTHER INFORMATION: Any amino acid except Lys and this region may
      encompass 2 to 4 residues wherein some positions may be absent
<220> FEATURE:
<221> NAME/KEY: MOD_RES
<222> LOCATION: (15)..(24)
<223> OTHER INFORMATION: Any amino acid except Lys and this region may
      encompass 6 to 10 residues wherein some positions may be absent
<220> FEATURE:
<221> NAME/KEY: MOD_RES
<222> LOCATION: (26)..(26)
<223> OTHER INFORMATION: Ala or Gln
<220> FEATURE:
<221> NAME/KEY: MOD_RES
<222> LOCATION: (27)..(27)
<223> OTHER INFORMATION: Gly, D-Asp or Ser
<220> FEATURE:
<221> NAME/KEY: MOD_RES
<222> LOCATION: (28)..(28)
<223> OTHER INFORMATION: Ser, His or Asn
<220> FEATURE:
<221> NAME/KEY: MOD_RES
<222> LOCATION: (29)..(29)
<223> OTHER INFORMATION: Bip, Phe, or beta-naphthylAla
<220> FEATURE:
<221> NAME/KEY: MOD_RES
<222> LOCATION: (31)..(31)
<223> OTHER INFORMATION: Thr or Ala
<220> FEATURE:
<221> NAME/KEY: MOD_RES
<222> LOCATION: (33)..(33)
<223> OTHER INFORMATION: Gly, Val or Leu
<220> FEATURE:
<223> OTHER INFORMATION: C-term may be NH2 or OH
```

```
<220> FEATURE:
<223> OTHER INFORMATION: See specification as filed for detailed
      description of substitutions and preferred embodiments

<400> SEQUENCE: 5

Cys Xaa Xaa Xaa Xaa Xaa Xaa Lys Cys Xaa Xaa Xaa Xaa Cys Xaa Xaa
1               5                   10                  15

Xaa Xaa Xaa Xaa Xaa Xaa Xaa Xaa Cys Xaa Xaa Xaa Xaa Cys Xaa Cys
            20                  25                  30

Xaa

<210> SEQ ID NO 6
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(6)
<223> OTHER INFORMATION: Any amino acid except Lys and this region may
      encompass 3 to 6 residues wherein some positions may be absent
<220> FEATURE:
<221> NAME/KEY: MOD_RES
<222> LOCATION: (9)..(12)
<223> OTHER INFORMATION: Any amino acid except Lys and this region may
      encompass 2 to 4 residues wherein some positions may be absent
<220> FEATURE:
<221> NAME/KEY: MOD_RES
<222> LOCATION: (14)..(23)
<223> OTHER INFORMATION: Any amino acid except Lys and this region may
      encompass 6 to 10 residues wherein some positions may be absent
<220> FEATURE:
<221> NAME/KEY: MOD_RES
<222> LOCATION: (25)..(25)
<223> OTHER INFORMATION: Ala or Gln
<220> FEATURE:
<221> NAME/KEY: MOD_RES
<222> LOCATION: (26)..(26)
<223> OTHER INFORMATION: Gly, D-Asp or Ser
<220> FEATURE:
<221> NAME/KEY: MOD_RES
<222> LOCATION: (27)..(27)
<223> OTHER INFORMATION: Ser, His or Asn
<220> FEATURE:
<221> NAME/KEY: MOD_RES
<222> LOCATION: (28)..(28)
<223> OTHER INFORMATION: Bip, Phe, or beta-naphthylAla
<220> FEATURE:
<221> NAME/KEY: MOD_RES
<222> LOCATION: (30)..(30)
<223> OTHER INFORMATION: Thr or Ala
<220> FEATURE:
<221> NAME/KEY: MOD_RES
<222> LOCATION: (32)..(32)
<223> OTHER INFORMATION: Gly, Val or Leu
<220> FEATURE:
<223> OTHER INFORMATION: C-term may be NH2 or OH
<220> FEATURE:
<223> OTHER INFORMATION: See specification as filed for detailed
      description of substitutions and preferred embodiments

<400> SEQUENCE: 6

Xaa Xaa Xaa Xaa Xaa Xaa Lys Cys Xaa Xaa Xaa Xaa Cys Xaa Xaa Xaa
1               5                   10                  15

Xaa Xaa Xaa Xaa Xaa Xaa Cys Xaa Xaa Xaa Xaa Cys Xaa Cys Xaa
            20                  25                  30

<210> SEQ ID NO 7
<211> LENGTH: 26
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: TPA-Asn
<220> FEATURE:
<221> NAME/KEY: MOD_RES
<222> LOCATION: (22)..(22)
<223> OTHER INFORMATION: Bip

<400> SEQUENCE: 7

Asn Leu His Phe Cys Gln Leu Arg Cys Lys Ser Leu Gly Leu Leu Gly
1               5                   10                  15

Lys Cys Ala Gly Ser Xaa Cys Ala Cys Val
            20                  25
```